US012577557B2

(12) United States Patent
Salit et al.

(10) Patent No.: US 12,577,557 B2
(45) Date of Patent: Mar. 17, 2026

(54) PRODUCTION AND TRACKING OF ENGINEERED CELLS WITH COMBINATORIAL GENETIC MODIFICATIONS

(71) Applicants: THE BOARD OF TRUSTEES OF THE LELAND STANFORD JUNIOR UNIVERSITY, Stanford, CA (US); GOVERNMENT OF THE UNITED STATES OF AMERICA, AS REPRESENTED BY THE SECRETARY OF COMMERCE, Gaithersburg, MD (US)

(72) Inventors: Marc Salit, Gaithersburg, MD (US); Lars M. Steinmetz, Stanford, CA (US); Robert St. Onge, Stanford, CA (US); Justin D. Smith, Stanford, CA (US); Kevin R. Roy, Gaithersburg, MD (US)

(73) Assignees: THE BOARD OF TRUSTEES OF THE LELAND STANFORD JUNIOR UNIVERSITY, Stanford, CA (US); GOVERNMENT OF THE UNITED STATES OF AMERICA, AS REPRESENTED BY THE SECRETARY OF COMMERCE, Gaithersburg, MD (US)

( * ) Notice: Subject to any disclaimer, the term of this patent is extended or adjusted under 35 U.S.C. 154(b) by 898 days.

(21) Appl. No.: 17/429,250

(22) PCT Filed: Feb. 7, 2020

(86) PCT No.: PCT/US2020/017315
§ 371 (c)(1),
(2) Date: Aug. 6, 2021

(87) PCT Pub. No.: WO2020/163779
PCT Pub. Date: Aug. 13, 2020

(65) Prior Publication Data
US 2022/0389415 A1     Dec. 8, 2022

Related U.S. Application Data

(60) Provisional application No. 62/803,242, filed on Feb. 8, 2019.

(51) Int. Cl.
*C12N 15/11* (2006.01)
*C12N 15/10* (2006.01)

(52) U.S. Cl.
CPC ....... *C12N 15/1093* (2013.01); *C12N 15/102* (2013.01); *C12N 15/1065* (2013.01);
(Continued)

(58) Field of Classification Search
None
See application file for complete search history.

(56) References Cited

U.S. PATENT DOCUMENTS 4,415,732 A     11/1983   Caruthers et al.
4,458,066 A     7/1984    Caruthers et al.
(Continued)

FOREIGN PATENT DOCUMENTS

WO     2017075529 A1     5/2017
WO     2018154027 A1     8/2018
(Continued)

OTHER PUBLICATIONS (Whole-organism lineage tracing by combinatorial and cumulative genome editing; Cell Lineage Tracing 2016) (Year: 2016).*
(Continued)

*Primary Examiner* — Heather Calamita
*Assistant Examiner* — Elizabeth Rose Lafave
(74) *Attorney, Agent, or Firm* — Mintz, Levin, Cohn, Ferris, Glovsky and Popeo, P.C.

(57)     ABSTRACT

Described herein are methods for making genetically modified cells by introducing combinations of genetic variants (designed or random) or constructs (genes or otherwise arbitrary DNA) into a population of cells, and for tracking each variant combination by sequentially building an array of barcodes at a common locus (chromosomal or plasmid), termed the barcode locus. Also described are the cells made by such methods.

19 Claims, 37 Drawing Sheets

Specification includes a Sequence Listing.

(52) U.S. Cl.
    CPC .......... *C12N 15/11* (2013.01); *C12N 2310/20*
        (2017.05); *C12Q 2521/301* (2013.01); *C12Q*
                        *2563/179* (2013.01)

(56) References Cited

U.S. PATENT DOCUMENTS

| | | |
|---|---|---|
| 5,831,005 A | 11/1998 | Zuckerman et al. |
| 5,877,278 A | 3/1999 | Zuckermann et al. |
| 5,977,301 A | 11/1999 | Zuckerman et al. |
| 2005/0147981 A1 | 7/2005 | Yamakawa et al. |
| 2016/0122748 A1 | 5/2016 | St et al. |
| 2018/0230461 A1 | 8/2018 | Gill et al. |

FOREIGN PATENT DOCUMENTS

| | | | | |
|---|---|---|---|---|
| WO | WO-2018152197 A1 * | 8/2018 | ..... | C12Y 305/04005 |
| WO | 2020163779 A1 | 8/2020 | | |

OTHER PUBLICATIONS (Polylox barcoding reveals haematopoietic stem cell fates realized in vivo; Nature, 2017) (Year: 2017).*
(Multiplexed precision genome editing with trackable genomic barcodes in yeast; Nature 2018) (Year: 2018).*
Guernet et al. (2016) "CRISPR-Barcoding for Intratumor Genetic Heterogeneity Modeling and Functional Analysis of Oncogenic Driver Mutations", Molecular cell, 63(3):526-538.
Branda et al. (Jan. 2004) "Talking about a Revolution: The Impact of Site-Specific Recombinases on Genetic Analyses in Mice", Developmental Cell, 6(1):7-28.
Chu et al. (Mar. 1981) "SV40 DNA Transfection of Cells in Suspension: Analysis of Efficiency of Transcription and Translation ofT-Antigen.", Gene, 13(2):197-202.
Chylinski et al. (Jun. 2014) "Classification and Evolution of Type II CRISPR-Cas Systems", Nucleic Acids Research, 42(10):6091-105.
Cleary et al. (Dec. 2004) "Production of complex nucleic acid libraries using highly parallel in situ bligonucleotide synthesis", Nature Methods, 1(3):241-248.
Elayadi et al. (Apr. 2001) "Application of PNA and LNA Oligomers to Chemotherapy", Current Opinion in Investigational Drugs, 2(4):558-561.
Fonfara et al. (Feb. 2014) "Phylogeny of Cas9 Determines Functional Exchangeability of Dual-RNA and Cas9 Among Orthologous Type II CRISPR-Cas Systems", Nucleic Acids Research, 42(4):2577-2590.
Gaj et al. (Jan. 2014) "Expanding the Scope of Site-Specific Recombinases for Genetic and Metabolic Engineering", Biotechnology and Bioengineering, 111(1):30 pages.
Garcia-Otin et al. (Jan. 1, 2006) "Mammalian Genome Targeting Using Site-Specific Recombinases", Frontiers in Bioscience, 11:1108-1136.
Graham et al. (Apr. 1973) "A New Technique for the Assay of Infectivity of Human Adenovirus 5 Dna", Virology, 52 (2):456-467.
Kapitonov et al. (Mar. 2016) "ISC, a Novel Group of Bacterial and Archaeal DNA Transposons That Encode Cas9 Homologs", Journal of Bacteriology, 198(5):797-807.
Koshkin et al. (Apr. 2, 1998) "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition", Tetrahedron, 54(14):3607-3630.
Kurreck et al. (2002) "Design of Antisense Oligonucleotides Stabilized by Locked Nucleic Acids", Nucleic Acids Research, 30(9):1911-1918.
Ledford Heidi. (Oct. 1, 2015) "Bacteria Yield New Gene Cutter", Nature, 526(7571):17(1 page).
Lin et al. (Oct. 2016) "Increasing the Efficiency of CRISPR/Cas9-mediated Precise Genome Editing of HSV-1 Virus in Human Cells", Scientific Reports, 6:34531(13 pages).

Maruyama et al. (May 2015) "Increasing the efficiency of precise genome editing with CRISPR-Cas9 by inhibition of honhomologous end joining", National Biotechnology, 33(5):9 pages.
Mckenna et al. (Jul. 29, 2016) "Whole-organism Lineage Tracing by Combinatorial and Cumulative Genome Editing", Science, 353(6298):27 Pages.
Murovec et al. (Aug. 2017) "New Variants of CRISPR RNA-Guided Genome Editing Enzymes", Plant Biotechnology Journal, 15(8):917-926.
NCBI (May 4, 2021) "Belliella Baltica Dsm 15883, Complete Sequence", NCBI Accession No. NC_018010.1, 2 pages.
NCBI (Jan. 31, 2021) "Corynebacterium Diphtheriae 241, Complete Sequence", NCBI Accession No. NC_016782.1, 2 pages.
NCBI (Feb. 7, 2021) "Corynebacterium Diphtheriae Hc01, Complete Sequence", NCBI Accession No. NC_016786.1, 2 pages.
NCBI (Jan. 17, 2021) "Corynebacterium Ulcerans 809, Complete Sequence", NCBI Accession No. NC_017317.1, 2 pages.
NCBI (Jan. 17, 2021) "Corynebacterium Ulcerans Br-ad22, Complete Sequence", NCBI Accession No. NC_015683.1, 2 pages.
NCBI, (Aug. 3, 2016) "Crispr-Associated Protein [*Campylobacter jejuni* Subsp. *jejuni* Nctc 11168 = Atcc 700819]", NCBI Accession No. YP_002344900.1, 2 pages.
NCBI (Dec. 16, 2014) "Crispr-System-like Protein [*Streptococcus thermophilus* Lmd-9]", NCBI Accession No. YP_820832.1, 2 pages.
NCBI (Oct. 29, 2018) "Hypothetical Protein [campylobacter Fetus]", NCBI Accession No. WP_059434633.1, 1 page.
NCBI (Dec. 17, 2014) "Hypothetical Protein Lin2744 [listeria Innocua Clip11262]", NCBI Accession No. NP_472073.1, 2 pages.
NCBI (Dec. 16, 2014) "Hypothetical Protein Nma0631 [neisseria Meningitidis 72491]", NCBI Accession No. YP_002342100.1, 2 pages.
NCBI (Oct. 9, 2019) "Multispecies: Type II Crispr Rna-guided Endonuclease Cas9 [campylobacter]", NCBI Accession No. WP_022552435.1, 2 pages.
NCBI (Nov. 28, 2020) "Prevotella Intermedia 17 Chromosome II, Complete Sequence", NCBI Accession No. NC_017861.1, 2 pages.
NCBI (May 4, 2021) "Psychroflexus Torquis Atcc 700755, Complete Sequence", NCBI Accession No. NC_018721.1, 2 pages.
NCBI (Jan. 24, 2021) "Spiroplasma Syrphidicola Ea-1, Complete Sequence", NCBI Accession No. NC_021284.1, 2 pages.
NCBI (Jan. 24, 2021) "Spiroplasma Taiwanense Ct-1, Complete Sequence", NCBI Accession No. NC_021846.1, 2 pages.
NCBI (Dec. 18, 2014) "Streptococcus Iniae Sf1, Complete Genome", NCBI Accession No. NC_021314.1, 1 page.
NCBI (Oct. 9, 2019) "Type II Crispr Rna-guided Endonuclease Cas9 [campylobacter Coli]", NCBI Accession No. WP_060786116.1, 2 pages.
NCBI (Oct. 9, 2019) "Type II Crispr Rna-guided Endonuclease Cas9 [enterococcus Faecalis]", NCBI Accession No. WP_033919308.1, 2 pages.
Ncbi, (Oct. 9, 2019) "Type Il Crispr Rna-Guided Endonuclease Cas9 [lacticaseibacillus Rhamnosus]", NCBI Accession No. WP_032965177.1, 2 pages.
NCBI (Oct. 9, 2019) "Type II Crispr Rna-Guided Endonuclease Cas9 [lactobacillus Rhamnosus]", NCBI Accession No. WP_048482595.1, 2 pages.
NCBI (Oct. 9, 2019) "Type II Crispr Rna-guided Endonuclease Cas9 [listeria Monocytogenes]", NCBI Accession No. WP_061665472.1, 2 pages.
NCBI (Oct. 9, 2019) "Type II Crispr Rna-Guided Endonuclease Cas9 [neisseria Meningitidis]", NCBI Accession No. WP_061704949.1, 2 pages.
NCBI (Oct. 9, 2019) "Type II Crispr Rna-guided Endonuclease Cas9 [staphylococcus Aureus]", NCBI Accession No. WP_001573634.1, 1 page.
NCBI (Oct. 9, 2019) "Type II Crispr Rna-guided Endonuclease Cas9 [streptococcus Mutans]", NCBI Accession No. WP_024786433.1, 2 pages.
NCBI (Oct. 9, 2019) "Type II Crispr Rna-guided Endonuclease Cas9 [streptococcus Mutans]", NCBI Accession No. WP_061046374.1, 2 pages.

(56) References Cited

OTHER PUBLICATIONS

NCBI (Oct. 9, 2019) "Type II Crispr Rna-guided Endonuclease Cas9 [streptococcus Pyogenes]", NCBI Accession No. WP_002989955. 1, 2 pages.

NCBI (Oct. 9, 2019) "Type II Crispr Rna-guided Endonuclease Cas9 [streptococcus Pyogenes]", NCBI Accession No. WP_011528583. 1, 2 pages.

NCBI (Oct. 9, 2019) "Type II Crispr Rna-guided Endonuclease Cas9 [streptococcus Pyogenes]", NCBI Accession No. WP_038434062. 1, 2 pages.

NCBI (Jun. 20, 2019) "Type II-B CRISPR-Associated RNA-Guided Endonuclease Cas9/Csx12 [Francisella hispaniensis]", NCBI Accession No. WP_014548420.1, 2 pages.

NCBI (Jun. 20, 2019) "Type II-B Crispr-Associated Rna-Guided Endonuclease Cas9/csx12 [francisella Tularensis]", NCBI Accession No. WP_032729892.1, 2 pages.

NCBI (Jun. 19, 2019) "Type II-B Crispr-associated Rna-Guided Endonuclease Cas9/csx12 [legionella Pneumophila]", NCBI Accession No. WP_062726656.1, 2 pages.

Nern et al. (Aug. 23, 2011) "Multiple new site-specific recombinases for use in manipulating animal genomes", Proceedings of the National Academy of Sciences of the United States of America, 108(34):14198-14203.

Nguyen et al. (Jul. 1, 2000) "Improving SH3 Domain Ligand Selectivity Using a Non-Natural Scaffold", Chemistry & Biology, 7(7):463-473.

Obika et al. (Jul. 23, 1998) "Stability and Structural Features of the Duplexes Containing Nucleoside Analogues with a Fixed N-type Conformation, 2'-0,4'-c-methyleneribonucleosides", Tetrahedron Letters, 39(30):5401-5404.

Pan et al. (Oct. 2016) "CRISPR RNA-Guided Fokl Nucleases Repair a PAH Variant in a Phenylketonuria Model", Scientific Reports, 6(1):35794(7 pages).

Roy et al. (Jul. 2018) "Multiplexed Precision Genome Editing with Trackable Genomic Barcodes in Yeast", Nature Biotechnology, 36(6):512-520(30 Pages).

Shmakov et al. (Nov. 5, 2015) "Discovery and Functional Characterization of Diverse Class 2 CRISPR-Cas Systems", Molecular Cell, 60(3):385-397.

Simon et al. (Oct. 15, 1992) "Peptoids: a Modular Approach to Drug Discovery", Proceedings of the National Academy of Sciences of the United States of America, 89(20):9367-9371.

Song et al. (Jan. 28, 2016) "RS-1 Enhances CRISPR/Cas9- and TALEN-mediated Knock-in Efficiency", Nature Communication, 7:10548(7 pages).

Svensen et al. (Sep. 23, 2011) "Microarray Generation of Thousand-Member Oligonucleotide Libraries", PLoS One, 6(9):e24906(8 pages).

Tsai et al. (Jun. 2014) "Dimeric CRISPR RNA-Guided Fokl Nucleases for Highly Specific Genome Editing", Nature Biotechnology, 32(6):22 pages.

Turan et al. (Sep. 2, 2011) "Site-specific recombinases: from tag-and-target- to tag-and-exchange-based genomic modifications", The Faseb Journal, 25(12):4088-4107.

Zetsche et al. (Oct. 22, 2015) "Cpf1 Is a Single RNA-Guided Endonuclease of a Class 2 CRISPR-Cas System", Cell, 163(3):26 pages.

Zhang et al. (Feb. 14, 2017) "Progress in Genome Editing Technology and Its Application in Plants", Frontiers in Plant Science, 8:177(17 pages).

* cited by examiner a) associate barcodes 1-5 with bc1:5 with paired-end sequencing
b) subsequent HTS-based phenotyping and strain identification
   with bc1:5

BspQI site n+1 gRNA scaffold · site n · KanR · HIS3, LEU2, or LYS2 · site n+1 · guide n · RH(n+1)

barcode 1 (bc1)

RH(n)

BspQI

AscI     BspQI     donor guide     TruSeq read 1 reverse primer 18 bp  15 bp  45 bp  12 bp

*  bc0 insert barcode          guide donor barcode

P7
i7     bc(n)     BspQI          donor          bc0     TruSeq read 1

RH(n+1)     RH(n)     * i5

P5 right homology length

-RH1 homology test performed with pKR529-based series
-cut site is present proximally downstream of editing guide SEQ ID NO:6    -TttccaTTACCCTGTTATCCCTaggAAA-
SEQ ID NO:7    AaaggtAATAATGGGACAATAGGGAtccTTT- GTTTcctAGGGATAACAGGGTAAtggaaA    SEQ ID NO:4
CAAAggaTCCCTATTGTCCCATTaccttT    SEQ ID NO:5

PRODUCTION AND TRACKING OF ENGINEERED CELLS WITH COMBINATORIAL GENETIC MODIFICATIONS

CROSS-REFERENCE TO RELATED APPLICATIONS

This application is a national stage application filed under 35 U.S.C. § 371 of International Application No. PCT/US2020/017315 filed on Feb. 7, 2020, which claims priority to U.S. provisional application No. 62/803,242, filed on Feb. 8, 2019, the contents of which are incorporated herein by reference in their entireties.

STATEMENT REGARDING FEDERALLY SPONSORED RESEARCH OR DEVELOPMENT

This invention was made with Government support under contract 70NANB15H268 awarded by the National Institute of Standards & Technology and under contracts GM110706, GM121932, and HG000205 awarded by the National Institutes of Health. The government has certain rights in the invention.

INCORPORATION BY REFERENCE OF SEQUENCE LISTING

This application contains a Sequence Listing which has been submitted in .txt format via EFS-WEB and is hereby incorporated by reference in its entirety. Said .txt copy, created Mar. 20, 2020 is named 041243-536001WO_SequenceListing_ST25.txt and is 4,096 bytes in size.

BACKGROUND

Uncovering the genetic basis of complex phenotypes and engineering biological systems with desirable properties are central challenges in quantitative genetics and synthetic biology. In order to achieve these goals, technologies are needed that enable testing the functional output of many different genetic variants and pathways in parallel. Recent advances in DNA synthesis have enabled the facile construction of CRISPR guide libraries, paired guide RNA-donor DNA libraries, and gene variant libraries, enabling large pools of genetic variants to be generated. While methods exist to track such individual variants in multiplexed assays where each cell harbors a single perturbation, there are currently few scalable methods available for producing and tracking higher order combinations of genetic variants in a pooled format. Such technologies would be critical for understanding how variants interact to modulate phenotype.

Thus, there remains a need for more efficient, flexible, and scalable methods of producing and tracking an arbitrary number of genetic changes in a single cell.

SUMMARY

The present disclosure relates to a method for introducing combinations of genetic variants (designed or random) or constructs (genes or otherwise arbitrary DNA) into a population of cells, and for tracking each variant combination by sequentially building an array of barcodes at a common locus (chromosomal or plasmid), termed the barcode locus. Each variant, genetic construct, or genetic modification is represented by a unique barcode within the array, such that DNA sequencing of the barcode array enables tracking the abundance of each variant combination within a population by sequencing-based counts. Importantly, the methods described herein are not restricted to associations with CRISPR-mediated genome editing and have broader applications for any genetic modification process that yields designed or random genetic changes, or for storage and compression of arbitrary digital information in DNA.

In one aspect, this disclosure relates to a method for producing a plurality of genetically engineered cells. In embodiments, the method includes (a) contacting a plurality of cells with a first gene editing agent and a first plurality of recombinant polynucleotides, each recombinant polynucleotide containing a unique polynucleotide barcode sequence, thereby forming a first plurality of gene edited and barcoded cells, each gene edited and barcoded cell having the first unique polynucleotide barcode inserted into a barcode locus and a first unique genetic modification; and (b) contacting the first plurality of gene edited and barcoded cells with a second gene editing agent and a second plurality of recombinant polynucleotides, each recombinant polynucleotide containing a unique polynucleotide barcode sequence, thereby forming a second plurality of gene edited and barcoded cells, each gene edited and barcoded cell having the second unique polynucleotide barcode inserted into a barcode locus and a second unique genetic modification; thereby producing a plurality of genetically engineered cells. In embodiments, the method includes repeating step (b) one or more times, wherein each repeat of step (b) employs a plurality of recombinant polynucleotides, such that the barcode locus includes a barcode array with a unique combination of recombinant polynucleotide barcodes.

In one aspect is provided a method for producing a plurality of genetically engineered cells by (a) contacting a plurality of cells with a first gene editing agent thereby producing a first plurality of gene edited cells each having a first unique genetic modification; (b) transfecting into the first plurality of gene edited cells a first plurality of recombinant polynucleotides, each recombinant polynucleotide containing a first unique polynucleotide barcode sequence, thereby forming a first plurality of gene edited and barcoded cells, each gene edited and barcoded cell having the first unique polynucleotide barcode inserted into a barcode locus and the first unique genetic modification; (c) contacting said first plurality of gene edited and barcoded cells with a second gene editing agent thereby producing a second plurality of gene edited cells each having a second unique genetic modification; and (d) transfecting into the second plurality of gene edited cells a second plurality of recombinant polynucleotides, each recombinant polynucleotide containing a second unique polynucleotide barcode sequence, thereby forming a second plurality of gene edited and barcoded cells, such that a second unique polynucleotide barcode is inserted into a barcode locus of each of said second plurality of gene edited and barcoded cells, each gene edited and barcoded cell having the second unique polynucleotide barcode inserted into a barcode locus and the second unique genetic modification; thereby producing a plurality of genetically engineered cells. In embodiments, the method includes repeating steps (c) and (d) one or more times, wherein each repeat of steps (c) and (d) employs a plurality of recombinant polynucleotides, such that the barcode locus includes a barcode array containing a unique combination of recombinant polynucleotide barcodes.

In embodiments, the first unique polynucleotide barcode is associated with the first unique genetic modification in each of said first plurality of gene edited and barcoded cells. In embodiments, the barcode locus and at least a portion of the genome of each of said first plurality of gene edited and barcoded cells are sequenced, such that the first unique polynucleotide barcode is associated with the first unique genetic modification in a database.

In embodiments, the second unique polynucleotide barcode is associated with the second unique genetic modification in each of said second plurality of gene edited and barcoded cells. In embodiments, the barcode locus and at least a portion of the genome of each of said second plurality of gene edited and barcoded cells are sequenced, such that the second unique polynucleotide barcode is associated with the second unique genetic modification in a database.

In embodiments, the method includes identifying the gene mutations in each of the plurality of genetically engineered cells by sequencing the barcode locus.

In one aspect is provided a method for producing a plurality of barcoded cells. In embodiments, the method includes (a) contacting a plurality of cells with a first plurality of recombinant polynucleotides, each recombinant polynucleotide containing a unique polynucleotide barcode sequence, such that a first unique polynucleotide barcode is inserted into a barcode locus of each of said first plurality of cells, thereby forming a first plurality of barcoded cells. In embodiments, the method further includes (b) contacting the first plurality of barcoded cells with a second plurality of recombinant polynucleotides, each recombinant polynucleotide containing a unique polynucleotide barcode sequence, such that a second unique polynucleotide barcode is inserted into the barcode locus of each of said first plurality of gene edited and barcoded cells, thereby forming a second plurality of gene edited and barcoded cells.

In one aspect is provided a method for compressing polynucleotide information into a single barcode in a cell. In embodiments, the method includes obtaining a cell having at least two unique polynucleotide barcodes in a barcode locus (a barcode array); inserting a new unique polynucleotide barcode in the barcode locus of the cell; and sequencing the barcode locus such that the new unique polynucleotide barcode (compressor barcode) is associated with the at least two unique polynucleotide barcodes. In embodiments, the method further includes removing the at least two unique polynucleotide barcodes from the barcode locus of the cell with the compressor barcode remaining in the barcode locus. This process can be referred to as "barcode compression."

In one aspect a plurality of gene edited and barcoded cells that were made by a method described herein is provided.

In one aspect a gene edited and barcoded cell that was made by a method described herein is provided.

In embodiments, each unique polynucleotide barcode is added adjacent to the previous unique polynucleotide barcode in the barcode locus. In embodiments, each unique polynucleotide barcode is added upstream of the previous unique polynucleotide barcode in the barcode locus. In embodiments, each unique polynucleotide barcode is added downstream of the previous unique polynucleotide barcode in the barcode locus.

In embodiments, each unique polynucleotide barcode is flanked on the recombinant polynucleotide by a right homology arm and/or a left homology arm. That is, a right homology arm may be on one side of the unique polynucleotide barcode, and a left homology arm on the other side. See, for example, FIGS. 1A-1D. In embodiments, each first unique polynucleotide barcode is flanked on each recombinant polynucleotide of the first plurality of polynucleotides by a first right homology arm, a second right homology arm, and a left homology arm, such that the first right homology arm and the left homology arm are homologous to a sequence at the barcode locus. In embodiments, each second unique polynucleotide barcode is flanked on each recombinant polynucleotide of the second plurality of polynucleotides by the second right homology arm, the left homology arm, and optionally a third right homology arm, such that the second right homology arm and the left homology arm are homologous to a sequence at the barcode locus after integration of the first unique polynucleotide barcode into the barcode locus.

In embodiments, each recombinant polynucleotide of the first plurality of polynucleotides includes a first marker polynucleotide between the left homology arm and the second right homology arm. In embodiments, each recombinant polynucleotide of the second plurality of polynucleotides includes a second marker polynucleotide between the left homology arm and the third right homology arm. In embodiments, the marker polynucleotide is incorporated into the barcode locus with the unique polynucleotide barcode. In embodiments, each recombinant polynucleotide further includes a marker polynucleotide. In embodiments, the marker polynucleotide is incorporated into the barcode locus with the unique polynucleotide barcode. In embodiments, the method includes selecting cells for presence of the marker polynucleotide integrating into the barcode locus. In embodiments, the method includes selecting cells for absence of the marker polynucleotide being removed from the barcode locus. In embodiments, the marker polynucleotide in the first plurality of recombinant polynucleotides is different from the marker polynucleotide in the second plurality of recombinant polynucleotides.

In embodiments, each unique polynucleotide is inserted in the barcode locus by homologous recombination. In embodiments, each unique polynucleotide is inserted in the barcode locus by non-homologous end joining. In embodiments, each unique polynucleotide is inserted in the barcode locus using an integrase or transposase.

In embodiments, the first gene editing agent is a meganuclease, zinc finger nuclease (ZFN), transcription activator-like effector-based nuclease (TALEN), RNA-guided nuclease, a chemical agent, a recombinase, an integrase, or a transposase. In embodiments, the second gene editing agent is a meganuclease, zinc finger nuclease (ZFN), transcription activator-like effector-based nuclease (TALEN), clustered regularly interspaced short palindromic repeats (CRISPR) system, a chemical agent, a recombinase, an integrase, or a transposase. In embodiments, the first and/or second gene editing agent is an RNA-guided nuclease. In embodiments, the first gene editing agent is a CRISPR system. In embodiments, the first gene editing agent is a CRISPR/Cas9 system. In embodiments, the second gene editing agent is a CRISPR system. In embodiments, the second gene editing agent is a CRISPR/Cas9 system. In embodiments, the first gene editing agent and the second gene editing agent are the same. In embodiments, the first gene editing agent and the second gene editing agent are different.

In embodiments, the method includes sequencing at least a portion of the chromosome of a cell from the first plurality of gene edited and barcoded cells. In embodiments, the method includes sequencing at least a portion of the chromosome of a cell from the second plurality of gene edited and barcoded cells. In embodiments, the barcode locus is sequenced. In embodiments, at least one genetic modification is determined by sequencing.

In embodiments, the method includes identifying at least one genetic modification with a unique polynucleotide barcode.

In embodiments, the method includes (i) inserting a new unique polynucleotide barcode in the barcode locus of each cell, wherein the barcode locus contains at least two unique polynucleotide barcodes prior to insertion of the new unique polynucleotide barcode. In embodiments, the method includes (ii) sequencing the barcode locus such that the new unique polynucleotide barcode is associated with the at least two prior unique polynucleotide barcodes. In embodiments, the method includes (iii) removing the at least two prior unique polynucleotide barcodes from the barcode locus of each cell. In embodiments, the method includes repeating steps (a), (b), (c), and/or (d), thereby producing a plurality of genetically engineered cells. In embodiments, the method includes repeating steps (i), (ii), and/or (iii), thereby producing a plurality of genetically engineered cells.

In embodiments, each recombinant polynucleotide further includes a third polynucleotide encoding a RNA-guided nuclease (or nickase). In embodiments, each recombinant polynucleotide further includes a donor polynucleotide. In embodiments, the RNA-guided nuclease is provided by a vector or a second nucleic acid sequence integrated into the genome of the cells. In embodiments, the RNA-guided nuclease is a Cas nuclease or an engineered RNA-guided FokI-nuclease. In embodiments, the Cas nuclease is Cas9 or Cas12a. In embodiments, the RNA-guided nuclease is SpCas9, SaCas9, NmCas9, St1Cas9, FnCas9, Cas12a (e.g., FnCpf1, AsCpf1, LbCpf1), Mad7, CasX, CasY, Cas13a, C2c1, C2c2, C2c3, LshC2c2, Cas14, dSpCas9-FokI, Split-SpCas9, SpCas9-nickase.

In embodiments, any or each recombinant polynucleotide is provided by a vector. In embodiments, the vector is a plasmid vector or a viral vector. In embodiments, the vector is a high copy number vector. In embodiments, any or each recombinant polynucleotide is expressed and reverse transcribed, e.g., through a retron system.

In embodiments, each recombinant polynucleotide further includes a second nucleic acid sequence encoding a guide RNA (e.g., guide X) capable of hybridizing with the recombinant polynucleotide. In embodiments, the guide RNA forms a complex with a nuclease in each cell such that the guide RNA-nuclease complex cleaves the recombinant polynucleotide. In embodiments, the recombinant polynucleotide is a plasmid vector and a nuclease complex (e.g., the guide RNA-nuclease complex) linearizes the plasmid vector.

In embodiments, the vector (e.g., plasmid) is removed from the cell (e.g., after the insertion step). In embodiments, the vector is cleaved by a nuclease in the cell. In embodiments, the vector is passively lost from the cell, e.g. by growth of the cell in a medium that does not select for retention of the vector.

In embodiments, each recombinant polynucleotide further includes a second nucleic acid sequence encoding a guide RNA (e.g., guide X) capable of hybridizing with the recombinant polynucleotide, wherein the guide RNA forms a complex with a nuclease in each cell such that the guide RNA-nuclease complex cleaves the barcode locus. In embodiments, the nucleic acid sequence encoding guide RNA is on a different polynucleotide than the donor DNA and/or the barcode polynucleotide. In embodiments, the cells are contacted with the nucleic acid sequence encoding guide RNA in a separate step from the polynucleotide containing the barcode polynucleotide.

In embodiments, the barcode locus is a chromosomal barcode locus. In embodiments, the barcode locus is a plasmid barcode locus.

In embodiments, the genetic modification is a designed genetic modification.

These and other embodiments of the subject disclosure will readily occur to those of skill in the art in view of the disclosure herein.

BRIEF DESCRIPTION OF THE DRAWINGS

FIG. 1A shows example uses of the barcoding methodology. FIGS. 1B-1D show an example operation of recursive barcoding. Shown are two versions of barcode recursion defined by whether they are assisted by selectable markers (left) or do not include a selectable marker (right). Barcoding is enabled by host-cell homologous recombination (HR), which utilizes two homology arms, termed left homology (LH) and right homology (RH).

FIG. 2A represents a barcode array that is integrated into a plurality of cells, each of which already contains a number of barcodes in the barcode locus. FIG. 2B shows the insertion of the compressor barcode ($bc_{1 \ldots 4}$) into the barcode locus which already contains multiple barcodes (bc4, bc3, bc2, bc1), followed by sequencing of the barcode locus to "compress" bc4, bc3, bc2, and bc1 into $bc_{1 \ldots 4}$. As shown in FIG. 2C, additional recursive barcode linkage can be performed, without needing to sequence the compressed barcodes in subsequent reads.

FIG. 3A shows the insertion of the compressor barcode ($bc_{1 \ldots 4}$) into the barcode locus which already contains multiple barcodes (bc4, bc3, bc2, bc1), followed by sequencing of the barcode locus to "compress" bc4, bc3, bc2, and bc1 into $bc_{1 \ldots 4}$. FIG. 3B shows a next round of barcoding that enables the removal of the linked barcodes which are no longer needed. In this example, bc5 is inserted adjacent to the left of $bc_{1 \ldots 4}$ and in the process removes bc1, bc2, bc3, and bc4, as well as RH1, RH2, RH3, RH4, and RH5 and their associated cleavage sites. This allows the recycling of these elements in the next series of barcoding rounds.

FIG. 4A shows a second round of barcode compression, which may be structurally identical to the first round (e.g., as shown in FIGS. 3A-3B), involving the use of the same RH element but different homologies and cleavage sites for further barcode linkage to the left and barcode compression to the right. In this example round of barcode compression, the incoming barcode $bc_{1 \ldots 7}$ compresses both the linked barcodes bc5, bc6, and bc7 and the previously compressed $bc_{1 \ldots 4}$. As shown in FIG. 4B, the next round of barcode linkage to the left removes bc5, bc6, and bc7 and the previously compressed bc1 . . . 4 enabling the recycling of previously used insertion elements in the next series of barcoding rounds.

FIG. 28A: An illustration shows guide-donor oligonucleotides which are cloned into the plasmid backbone with the addition of a barcode sequence, labeled bc0, adjacent to the donor. FIG. 28B: The illustration shows that round 1 plasmids can be parsed first in yeast or bacteria to create a library where each guide-donor is sequence perfect and present at equal abundance, and then the MARVEL round 1 insert removed by in vitro SceI enzyme treatment, leaving a left homology (CYCIt) and a right homology (msd). FIG. 28C: The illustration shows the linearized backbone generated by SceI cleavage can be transformed directly into yeast along with the appropriate round of MARVEL insert. Yeast homology directed repair assembles the plasmid via the left homology (CYCIt) and a right homology (msd) which are present on both the guide-donor backbone and the barcoded MARVEL inserts.

DETAILED DESCRIPTION

Figure 1A:
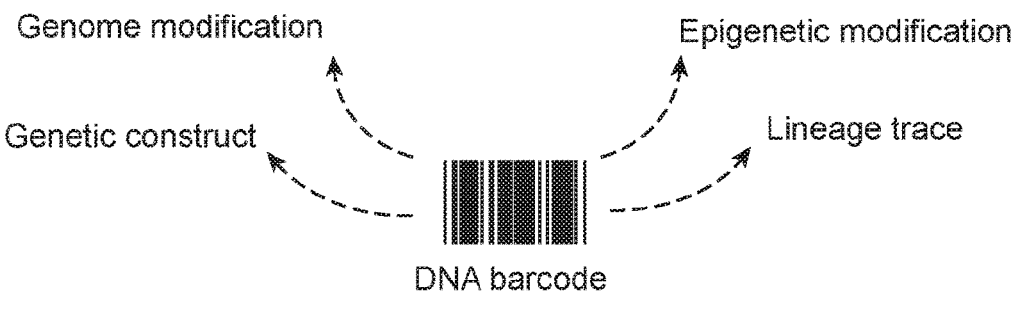
FIGS. 1A-1D show elements of recursive barcode linkage.

After reading this description it will become apparent to one skilled in the art how to implement the technology described herein in various alternative embodiments and alternative applications. However, all the various embodiments will not be described herein. It will be understood that the embodiments presented here are presented by way of an example only, and not limitation. As such, this detailed description of various alternative embodiments should not be construed to limit the scope or breadth of the present disclosure as set forth herein.

It is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description is divided into various sections only for the reader's convenience and disclosure found in any section may be combined with that in another section. Titles or subtitles may be used in the specification for the convenience of a reader, which are not intended to influence the scope of the present disclosure.

Definitions

Unless defined otherwise, all technical and scientific terms used herein have the same meaning as commonly understood by one of ordinary skill in the art to which this technology belongs. In this specification and in the claims that follow, reference will be made to a number of terms that shall be defined to have the following meanings:

The terminology used herein is for the purpose of describing particular embodiments only and is not intended to be limiting. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to an amount means that the amount may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claims. "Consisting of" shall mean excluding more than trace elements of other ingredients and substantial method steps. Embodiments defined by each of these transition terms are within the scope of this disclosure.

A "barcode" refers to one or more polynucleotide sequences that are used to identify a nucleic acid or cell with which the barcode is associated. Barcodes can be 3-1000 or more nucleotides in length. In embodiments, the length is preferably 10-250 nucleotides. In embodiments, the length is 10-30 nucleotides. In embodiments, the length is 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, or 1000 nucleotides. Barcodes may be used, for example, to identify a single cell, subpopulation of cells, colony, or sample from which a nucleic acid originated. Barcodes may also be used to identify the position (i.e., positional barcode) of a cell, colony, or sample from which a nucleic acid originated, such as the position of a colony in a cellular array, the position of a well in a multi-well plate, or the position of a tube, flask, or other container in a rack. In particular, a barcode may be used to identify a genetically modified cell from which a nucleic acid originated. In some embodiments, a barcode is used to identify a particular type of genome edit. For example, a guide RNA-donor polynucleotide cassette itself can be used as a barcode to identify a genetically modified cell from which a nucleic acid originated. Alternatively, a unique barcode may be used to identify each guide-RNA-donor polynucleotide cassette used in multiplex genome editing. Furthermore, multiple barcodes can be used in combination to identify different features of a nucleic acid. For example, positional barcoding (e.g., to identify the position of a cell, colony, culture, or sample in an array, multi-well plate, or rack) can be combined with barcodes identifying guide-RNA-donor polynucleotide cassettes used in genome editing. In some embodiments, barcodes are inserted into a nucleic acid (e.g., at a "barcode locus") at each round of genome editing to identify the guide-RNAs and/or donor polynucleotides used in genetic modification of a cell.

The terms "polypeptide" and "protein" refer to a polymer of amino acid residues and are not limited to a minimum length. Thus, peptides, oligopeptides, dimers, multimers, and the like, are included within the definition. Both full length proteins and fragments thereof are encompassed by the definition. The terms also include post expression modifications of the polypeptide, for example, glycosylation, acetylation, phosphorylation, hydroxylation, and the like. Furthermore, for purposes of the present disclosure, a "polypeptide" refers to a protein which includes modifications, such as deletions, additions and substitutions to the native sequence, so long as the protein exhibits desired activity. These modifications may be deliberate, as through site directed mutagenesis, or may be accidental, such as through mutations of hosts which produce the proteins or errors due to PCR amplification.

The term "gene modification" refers to any change within the genome (chromosomal or extra-chromosomal, e.g., plasmid, mitochondrial) of a cell. A gene modification may include, without limitation, a mutation, deletion, insertion, or substitution of one or more nucleotides in a polynucleotide sequence; insertion of a polynucleotide sequence; deletion of a polynucleotide sequence, e.g., a gene or part of a gene; translocation or reciprocal translocation of a polynucleotide sequence; chromosome fusion; and/or epigenetic modification to a polynucleotide sequence.

The term "Cas9" as used herein encompasses type II clustered regularly interspaced short palindromic repeats (CRISPR) system Cas9 endonucleases from any species, and also includes biologically active fragments, variants, analogs, and derivatives thereof that retain Cas9 endonuclease activity (i.e., catalyze site-directed cleavage of DNA to generate double-strand breaks). A Cas9 endonuclease binds to and cleaves DNA at a site comprising a sequence complementary to its bound guide RNA (gRNA).

A Cas9 polynucleotide, nucleic acid, oligonucleotide, protein, polypeptide, or peptide refers to a molecule derived from any source. The molecule need not be physically derived from an organism, but may be synthetically or recombinantly produced. Cas9 sequences from a number of bacterial species are well known in the art and listed in the National Center for Biotechnology Information (NCBI) database. See, for example, NCBI entries for Cas9 from: *Streptococcus pyogenes* (WP_002989955, WP_038434062, WP_011528583); *Campylobacter jejuni* (WP_022552435, YP_002344900), *Campylobacter coli* (WP_060786116); *Campylobacter fetus* (WP_059434633); *Corynebacterium ulcerans* (NC_015683, NC_017317); *Corynebacterium diphtheria* (NC_016782, NC_016786); *Enterococcus faecalis* (WP_033919308); *Spiroplasma syrphidicola* (NC_021284); *Prevotella intermedia* (NC_017861); *Spiroplasma taiwanense* (NC_021846); *Streptococcus iniae* (NC_021314); *Belliella baltica* (NC_018010); *Psychroflexus torquisI* (NC_018721); *Streptococcus thermophilus* (YP_820832), *Streptococcus mutans* (WP_061046374, WP_024786433); *Listeria innocua* (NP_472073); *Listeria monocytogenes* (WP_061665472); *Legionella pneumophila* (WP_062726656); *Staphylococcus aureus* (WP_001573634); *Francisella tularensis* (WP_032729892, WP_014548420), *Enterococcus faecalis* (WP_033919308); *Lactobacillus rhamnosus* (WP_048482595, WP_032965177); and *Neisseria meningitidis* (WP_061704949, YP_002342100); all of which sequences (as entered by the date of filing of this application) are herein incorporated by reference. Any of these sequences or a variant thereof comprising a sequence having at least about 70-100% sequence identity thereto, including any percent identity within this range, such as 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity thereto, can be used for genome editing, as described herein, wherein the variant retains biological activity, such as Cas9 site-directed endonuclease activity. An amino acid sequence made from any of these sequences, or a variant thereof comprising an amino acid sequence having at least about 70-100% sequence identity thereto, including any percent identity within this range, such as 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity thereto, can be used for genome editing, as described herein, wherein the variant retains biological activity, such as Cas9 site-directed endonuclease activity. See also Fonfara et al. (2014) Nucleic Acids Res. 42(4):2577-90; Kapitonov et al. (2015) J. Bacteriol. 198(5):797-807, Shmakov et al. (2015) Mol. Cell. 60(3):385-397, and Chylinski et al. (2014) Nucleic Acids Res. 42(10):6091-6105); for sequence comparisons and a discussion of genetic diversity and phylogenetic analysis of Cas9.

A RNA-guided nuclease as described herein may be a nickase. CRISPR/Cas nickase mutants introduce gRNA-targeted single-strand breaks in DNA instead of the double-strand breaks created by wild type Cas enzymes.

By "derivative" is intended any suitable modification of the native polypeptide of interest, of a fragment of the native polypeptide, or of their respective analogs, such as glycosylation, phosphorylation, polymer conjugation (such as with polyethylene glycol), or other addition of foreign moieties, as long as the desired biological activity of the native polypeptide is retained. Methods for making polypeptide fragments, analogs, and derivatives are generally available in the art.

By "fragment" is intended a molecule consisting of only a part of the intact full-length sequence and structure. The fragment can include a C-terminal deletion an N-terminal deletion, and/or an internal deletion of the polypeptide. Active fragments of a particular protein or polypeptide will generally include at least about 5-10 contiguous amino acid residues of the full length molecule, preferably at least about 15-25 contiguous amino acid residues of the full length molecule, and most preferably at least about 20-50 or more contiguous amino acid residues of the full length molecule, or any integer between 5 amino acids and the full length sequence, provided that the fragment in question retains biological activity, such as Cas9 site-directed endonuclease activity.

"Substantially purified" generally refers to isolation of a substance (compound, polynucleotide, nucleic acid, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

As used herein, the phrase "heterogeneous population of cells" refers to a mixture of at least two types of cells, one type being the cells of interest (e.g., having a genomic modification of interest). The heterogeneous population of cells may be derived from any organism.

The terms "isolating" and "isolation," as used herein in the context of selecting a cell or population of cells having a genomic modification of interest, refer to separating a cell or population of cells having the genomic modification of interest from a heterogeneous population of cells, such as by positive or negative selection, or such as by clonal isolation from a complex colony array.

The term "selection marker" or "marker" refers to a marker which can be used for identification or enrichment of a cell population from a heterogeneous population of cells, either by positive selection (selecting cells expressing the marker) or by negative selection (excluding cells expressing the marker).

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, microRNA, DNA:RNA hybrids, and hybrids between PNAs and DNA or RNA, and also include known types of modifications, for example, labels which are known in the art, methylation, "caps," substitution of one or more of the naturally occurring nucleotides with an analog (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, 0(6)-methylguanine, and 2-thiocytidine), intemucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. The term also includes locked nucleic acids (e.g., comprising a ribonucleotide that has a methylene bridge between the 2'-oxygen atom and the 4'-carbon atom). See, for example, Kurreck et al. (2002) Nucleic Acids Res. 30: 1911-1918; Elayadi et al. (2001) Curr. Opinion Invest. Drugs 2: 558-561; Orum et al. (2001) Curr. Opinion Mol. Ther. 3: 239-243; Koshkin et al. (1998) Tetrahedron 54: 3607-3630; Obika et al. (1998) Tetrahedron Lett. 39: 5401-5404.

The terms "hybridize" and "hybridization" refer to the formation of complexes between nucleotide sequences which are sufficiently complementary to form complexes via Watson-Crick base pairing.

The term "homologous region" refers to a region of a nucleic acid with homology to another nucleic acid region. Thus, whether a "homologous region" is present in a nucleic acid molecule is determined with reference to another nucleic acid region in the same or a different molecule. Further, since a nucleic acid is often double-stranded, the term "homologous region," as used herein, refers to the ability of nucleic acid molecules to hybridize to each other. For example, a single-stranded nucleic acid molecule can have two homologous regions which are capable of hybridizing to each other. Thus, the term "homologous region" includes nucleic acid segments with complementary sequences. Homologous regions may vary in length, but will typically be between 4 and 500 nucleotides (e.g., from about 4 to about 40, from about 40 to about 80, from about 80 to about 120, from about 120 to about 160, from about 160 to about 200, from about 200 to about 240, from about 240 to about 280, from about 280 to about 320, from about 320 to about 360, from about 360 to about 400, from about 400 to about 440, etc.).

As used herein, the terms "complementary" or "complementarity" refers to polynucleotides that are able to form base pairs with one another. Base pairs are typically formed by hydrogen bonds between nucleotide units in an anti-parallel orientation between polynucleotide strands. Complementary polynucleotide strands can base pair in a Watson-Crick manner (e.g., A to T, A to U, C to G), or in any other manner that allows for the formation of duplexes. As persons skilled in the art are aware, when using RNA as opposed to DNA, uracil (U) rather than thymine (T) is the base that is considered to be complementary to adenosine. However, when a uracil is denoted in the context of the present disclosure, the ability to substitute a thymine is implied, unless otherwise stated. "Complementarity" may exist between two RNA strands, two DNA strands, or between a RNA strand and a DNA strand. It is generally understood that two or more polynucleotides may be "complementary" and able to form a duplex despite having less than perfect or less than 100% complementarity. Two sequences are "perfectly complementary" or "100% complementary" if at least a contiguous portion of each polynucleotide sequence, comprising a region of complementarity, perfectly base pairs with the other polynucleotide without any mismatches or interruptions within such region. Two or more sequences are considered "perfectly complementary" or "100% complementary" even if either or both polynucleotides contain additional non-complementary sequences as long as the contiguous region of complementarity within each polynucleotide is able to perfectly hybridize with the other. "Less than perfect" complementarity refers to situations where less than all of the contiguous nucleotides within such region of complementarity are able to base pair with each other. Determining the percentage of complementarity between two polynucleotide sequences is a matter of ordinary skill in the art. For purposes of Cas9 targeting, a gRNA may comprise a sequence "complementary" to a target sequence (e.g., major or minor allele), capable of sufficient base-pairing to form a duplex (i.e., the gRNA hybridizes with the target sequence). Additionally, the gRNA may comprise a sequence complementary to a PAM sequence, wherein the gRNA also hybridizes with the PAM sequence in a target DNA.

A "target site" or "target sequence" is the nucleic acid sequence recognized (i.e., sufficiently complementary for hybridization) by a guide RNA (gRNA) or a homology arm of a donor polynucleotide. The target site may be allele-specific (e.g., a major or minor allele).

The term "donor polynucleotide" refers to a polynucleotide that provides a sequence of an intended edit to be integrated into the genome at a target locus by HDR.

By "homology arm" is meant a portion of a donor polynucleotide that is responsible for targeting the donor polynucleotide to the genomic sequence to be edited in a cell. The donor polynucleotide typically comprises a 5' homology arm that hybridizes to a 5' genomic target sequence and a 3' homology arm that hybridizes to a 3' genomic target sequence flanking a nucleotide sequence comprising the intended edit to the genomic DNA. The homology arms are referred to herein as 5' and 3' (i.e., upstream and downstream) homology arms, which relates to the relative position of the homology arms to the nucleotide sequence comprising the intended edit within the donor polynucleotide. The 5' and 3' homology arms hybridize to regions within the target locus in the genomic DNA to be modified, which are referred to herein as the "5' target sequence" and "3' target sequence," respectively. The nucleotide sequence comprising the intended edit is integrated into the genomic DNA by HDR at the genomic target locus recognized (i.e., sufficiently complementary for hybridization) by the 5' and 3' homology arms.

"Administering" a nucleic acid, such as a donor polynucleotide, guide RNA, or Cas9 expression system to a cell comprises transducing, transfecting, electroporating, translocating, fusing, phagocytosing, shooting or ballistic methods, etc., i.e., any means by which a nucleic acid can be transported across a cell membrane.

By "selectively binds" with reference to a guide RNA is meant that the guide RNA binds preferentially to a target sequence of interest or binds with greater affinity to the target sequence than to other genomic sequences. For example, a gRNA will bind to a substantially complementary sequence and not to unrelated sequences. A gRNA that "selectively binds" to a particular allele, such as a particular mutant allele (e.g., allele comprising a substitution, insertion, or deletion), denotes a gRNA that binds preferentially to the particular target allele, but to a lesser extent to a wild-type allele or other sequences. A gRNA that selectively binds to a particular target DNA sequence will selectively direct binding of an RNA-guided nuclease (e.g., Cas9) to a substantially complementary sequence at the target site and not to unrelated sequences.

As used herein, the term "recombination target site" denotes a region of a nucleic acid molecule comprising a binding site or sequence-specific motif recognized by a site-specific recombinase that binds at the target site and catalyzes recombination of specific sequences of DNA at the target site. Site-specific recombinases catalyze recombination between two such target sites. The relative orientation of the target sites determines the outcome of recombination. For example, translocation occurs if the recombination target sites are on separate DNA molecules.

As used herein, the terms "label" and "detectable label" refer to a molecule capable of detection, including, but not limited to, radioactive isotopes, fluorescers,™chemiluminescers, chromophores, enzymes, enzyme substrates, enzyme cofactors, enzyme inhibitors, semiconductor nanoparticles, dyes, metal ions, metal sols, ligands (e.g., biotin, streptavidin or haptens) and the like. The term "fluorescer" refers to a substance or a portion thereof which is capable of exhibiting fluorescence in the detectable range. Particular examples of labels which may be used in the practice of the present disclosure include, but are not limited to, SYBR® green, SYBR® gold, a CAL FLUOR® dye such as CAL FLUOR® Gold 540, CAL FLUOR® Orange 560, CAL FLUOR® Red 590, CAL FLUOR® Red 610, and CAL FLUOR® Red 635, a QUASAR® dye such as QUASAR® 570, QUASAR® 670, and QUASAR® 705, an ALEXA FLUOR® such as ALEXA FLUOR® 350, ALEXA FLUOR® 488, ALEXA FLUOR® 546, ALEXA FLUOR® 555, ALEXA FLUOR® 594, ALEXA FLUOR® 647, and ALEXA FLUOR® 784, a cyanine dye such as Cy 3, Cy3.5, Cy5, Cy5.5, and Cy7, fluorescein, 2', 4', 5', 7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), rhodamine, carboxy-X-rhodamine (ROX), tetramethyl rhodamine (TAMRA), FITC, dansyl, umbelliferone, dimethyl acridinium ester (DMAE), Texas red, luminol, NADPH, horseradish peroxidase (HRP), and α-β-galactosidase.

"Homology" refers to the percent identity between two polynucleotide or two polypeptide moieties. Two nucleic acid, or two polypeptide sequences are "substantially homologous" to each other when the sequences exhibit at least about 50% sequence identity, preferably at least about 75% sequence identity, more preferably at least about 80% to 85% sequence identity, more preferably at least about 90% sequence identity, and most preferably at least about 95% to 98% sequence identity over a defined length of the molecules. As used herein, substantially homologous also refers to sequences showing complete identity to the specified sequence.

In general, "identity" refers to an exact nucleotide to nucleotide or amino acid to amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN™, Dayhoff, M.O. in Atlas of Protein Sequence and Structure M.O. Dayhoff ed., 5 Suppl. 3:353 358, National biomedical Research Foundation, Washington, DC, which adapts the local homology algorithm of Smith and Waterman Advances in Appl. Math. 2:482 489, 1981 for peptide analysis. Programs for determining nucleotide sequence identity are available in the Wisconsin Sequence Analysis Package, Version 8 (available from Genetics Computer Group™, Madison, WI) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present disclosure is to use the MPSRCH package of programs copyrighted by the University of Edinburgh, developed by John F. Collins and Shane S. Sturrok, and distributed by IntelliCorp, Inc.™ (Mountain View, CA). From this suite of packages, the Smith Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed byqUA-SARdigestion with single stranded specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction, and cell-to-cell fusion by mating or f-mating are included. The exogenous polynucleotide may be maintained as a non-integrated vector, for example, a plasmid, or alternatively, may be integrated into the host genome.

"Recombinant host cells", "host cells", "cells", "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transformed. In certain embodiments, the cells to be genetically modified are eukaryotic or prokaryotic. In embodiments, the cells are yeast cells, which can be haploid or diploid yeast cells. In embodiments, the cells are mammalian cells, bacterial cells, fungal cells, or plant cells. In embodiments, the cells are human cells.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), introns (located anywhere in the RNA), and translation termination sequences.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (2001) Molecular Cloning, a laboratory manual, 3rd edition, Cold Spring Harbor Laboratories™, New York, Davis et al. (1995) Basic Methods in Molecular Biology, 2nd edition, McGraw-Hill, and Chu et al. (1981) Gene 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as plasmid and viral vectors.

The terms "variant," "analog" and "mutein" refer to biologically active derivatives of the reference molecule that retain desired activity, such as site-directed Cas9 endonuclease activity. In general, the terms "variant" and "analog" refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and U.S. Pat. No. 5,977,301; Nguyen et al., Chem. Biol. (2000) 7:463-473; and Simon et al., Proc. Natl. Acad. Sci. USA (1992) 89:9367-9371 for descriptions of peptoids). Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar— alanine, valine, leucine, isoleucine, proline, phenylalanine, methionine, tryptophan; and (4) uncharged polar—glycine, asparagine, glutamine, cysteine, serine threonine, and tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, adenoviruses, retroviruses, alphaviruses, pox viruses, and vaccinia viruses.

The term "derived from" is used herein to identify the original source of a molecule but is not meant to limit the method by which the molecule is made which can be, for example, by chemical synthesis or recombinant means.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Before describing the present disclosure in detail, it is to be understood that this disclosure is not limited to particular formulations or process parameters as such may, of course, vary. It is also to be understood that the terminology used herein is for the purpose of describing particular embodiments of the disclosure only, and is not intended to be limiting.

Although a number of methods and materials similar or equivalent to those described herein can be used in the practice of the present disclosure, the preferred materials and methods are described herein.

Methods

Described herein are methods for introducing combinations of genetic variants (designed or random) or constructs (genes or otherwise arbitrary DNA) into a population of cells, and for tracking each variant combination by sequentially building an array of barcodes at a common locus (chromosomal or plasmid), termed the barcode locus. Each variant, genetic construct, or genetic modification is represented by a unique barcode, such that sequencing the barcode and its adjacent barcode(s) enables tracking the abundance of each variant permutation within a population of cells by sequencing-based counts.

In one aspect, this disclosure relates to a method for producing a plurality of genetically engineered cells. In embodiments, the method includes (a) contacting a plurality of cells with a first gene editing agent and a first plurality of recombinant polynucleotides, each recombinant polynucleotide comprising a unique polynucleotide barcode sequence, thereby forming a first plurality of gene edited and barcoded cells, each gene edited and barcoded cell comprising the first unique polynucleotide barcode inserted into a barcode locus and a first unique genetic modification; and (b) contacting the first plurality of gene edited and barcoded cells with a second gene editing agent and a second plurality of recombinant polynucleotides, each recombinant polynucleotide comprising a unique polynucleotide barcode sequence, thereby forming a second plurality of gene edited and barcoded cells, each gene edited and barcoded cell comprising the second unique polynucleotide barcode inserted into a barcode locus and a second unique genetic modification; thereby producing a plurality of genetically engineered cells. In embodiments, the method includes repeating step (b) one or more times, wherein each repeat of step (b) employs the same or different plurality of recombinant polynucleotides, each recombinant polynucleotide comprising a unique polynucleotide barcode sequence.

In one aspect is provided a method for producing a plurality of genetically engineered cells by (a) contacting a plurality of cells with a first gene editing agent thereby producing a first plurality of gene edited cells each comprising a first unique genetic modification; (b) transfecting into the first plurality of gene edited cells a first plurality of recombinant polynucleotides, each recombinant polynucleotide comprising a first unique polynucleotide barcode sequence, thereby forming a first plurality of gene edited and barcoded cells, each gene edited and barcoded cell comprising the first unique polynucleotide barcode inserted into a barcode locus and the first unique genetic modification. In this way, cells can be genetically modified by an unknown (e.g., random) mutation or other change, and the barcode can be associated with that change after the mutation/change is made within the cell. In embodiments, the method includes (c) contacting said first plurality of gene edited and barcoded cells with a second gene editing agent thereby producing a second plurality of gene edited cells each comprising a second unique genetic modification; and (d) transfecting into the second plurality of gene edited cells a second plurality of recombinant polynucleotides, each recombinant polynucleotide comprising a second unique polynucleotide barcode sequence, thereby forming a second plurality of gene edited and barcoded cells, such that a second unique polynucleotide barcode is inserted into a barcode locus of each of said second plurality of gene edited and barcoded cells, each gene edited and barcoded cell comprising the second unique polynucleotide barcode inserted into a barcode locus and the second unique genetic modification; thereby producing a plurality of genetically engineered cells. In embodiments, the method includes repeating steps (c) and (d) one or more times, wherein each repeat of steps (c) and (d) employs the same or different plurality of recombinant polynucleotides, each recombinant polynucleotide comprising a unique polynucleotide barcode sequence.

In embodiments, a plurality of genetically engineered cells can be made by any combination of (a) contacting a plurality of cells with a first gene editing agent and a first plurality of recombinant polynucleotides, each recombinant polynucleotide comprising a unique polynucleotide barcode sequence, thereby forming a first plurality of gene edited and barcoded cells, each gene edited and barcoded cell comprising the first unique polynucleotide barcode inserted into a barcode locus and a first unique genetic modification; and (b) contacting said first plurality of gene edited and barcoded cells with a second gene editing agent thereby producing a second plurality of gene edited cells each comprising a second unique genetic modification; and (c) transfecting into the second plurality of gene edited cells a second plurality of recombinant polynucleotides, each recombinant polynucleotide comprising a second unique polynucleotide barcode sequence, thereby forming a second plurality of gene edited and barcoded cells, such that a second unique polynucleotide barcode is inserted into a barcode locus of each of said second plurality of gene edited and barcoded cells, each gene edited and barcoded cell comprising the second unique polynucleotide barcode inserted into a barcode locus and the second unique genetic modification. Steps (a) and (b)/(c) can be performed in any order. In embodiments, step (a) and/or (b)/(c) is repeated one or more times to further genetically modify the plurality of cells.

The plurality of cells may be made up of all the same cells (e.g. the same genus/species of cells, and/or having the same genetic sequence in each cell) or may be different cells (e.g. wherein at least some of the cells have at least one base pair change in the genomic sequence compared to another cell or cells in the plurality of cells). As used herein, the term "genomic sequence" or "genome" may be any DNA within a cell that encodes at least one gene, including but not limited to a chromosomal, plasmid, or mitochondrial DNA.

The term "unique polynucleotide barcode sequence" or "unique polynucleotide barcode" indicates that many or all of the cells in the plurality of cells have a different polynucleotide barcode sequence therein. In embodiments, the plurality of recombinant polynucleotides is a library of polynucleotides, where each polynucleotide includes a different barcode sequence. As would be understood to a person of skill in the art, a polynucleotide library may include more than a single copy of a given recombinant polynucleotide, but within a plurality of recombinant polynucleotides there will be a population of recombinant polynucleotides that each has a different sequence. In embodiments, each recombinant polynucleotide also includes a sequence (e.g., a donor DNA sequence) that contains a genetic modification (and/or can be used to create the genetic modification within a cell). In such embodiments, the barcode and the genetic modification are associated (e.g., in a database) so that a cell can be identified as having the genetic modification by determining which barcode(s) is present in the barcode locus (e.g., by sequencing). Similarly, a "unique genetic modification" indicates that many or all of the cells in the plurality of cells have a different genetic modification therein.

In embodiments, the first unique polynucleotide barcode is associated with the first unique genetic modification in each of said first plurality of gene edited and barcoded cells. "Associated" in this context refers to the correspondence of the genetic modification with the barcode, such that knowledge of the barcode (e.g., that a cell contains a specific barcode) indicates that the cell contains the corresponding genetic modification. In embodiments, the barcode locus and at least a portion of the genome of each of said first plurality of gene edited and barcoded cells are sequenced, such that the first unique polynucleotide barcode is associated with the first unique genetic modification in a database. In embodiments, the second unique polynucleotide barcode is associated with the second unique genetic modification in each of said second plurality of gene edited and barcoded cells. In embodiments, the barcode locus and at least a portion of the genome of each of said second plurality of gene edited and barcoded cells are sequenced, such that the second unique polynucleotide barcode is associated with the second unique genetic modification in a database. For example, the barcode locus and at least the portion of the genome containing a genetic modification are sequenced in a cell to identify what genetic modification is present in a cell containing a particular unique barcode, and that information is entered into a database such that the barcode is associated with the genetic modification. This allows a cell to be identified as having the genetic modification by sequencing only the barcode locus in the future.

In some embodiments, the barcode is associated with a genetic modification (e.g., in a database) prior to contacting a plurality of cells with the plurality of recombinant polynucleotides. That is, each recombinant polynucleotide may contain both a unique barcode and a unique genetic modification (e.g., donor DNA or other sequence that includes the modification and/or will cause the modification in a target cell), and the unique barcode and the unique genetic modification are associated (e.g., by sequencing of the recombinant polynucleotide) prior to contacting the plurality of cells with the recombinant polynucleotide.

In embodiments, the method includes identifying the gene mutations in each of the plurality of genetically engineered cells by sequencing the barcode locus. Sequencing of the barcode locus in each cell (or a clonal colony from each cell) will determine the barcode sequence(s) that are present in each cell. That can be used to query the database and determine the genetic modification that has been associated with that barcode. Where multiple barcodes are present, the database is queried for each barcode sequence, which allows determination of multiple genetic modifications in a single cell. In addition, the order in which the barcodes are present indicates the order in which the modifications were made.

In one aspect is provided a method for producing a plurality of barcoded cells. In embodiments, the method includes (a) contacting a plurality of cells with a first plurality of recombinant polynucleotides, each recombinant polynucleotide comprising a unique polynucleotide barcode sequence, such that a first unique polynucleotide barcode is inserted into a barcode locus of each of said first plurality of cells, thereby forming a first plurality of barcoded cells. In embodiments, the method further includes (b) contacting the first plurality of barcoded cells with a second plurality of recombinant polynucleotides, each recombinant polynucleotide comprising a unique polynucleotide barcode sequence, such that a second unique polynucleotide barcode is inserted into the barcode locus of each of said first plurality of gene edited and barcoded cells, thereby forming a second plurality of gene edited and barcoded cells. The barcodes in such cells can be linked to/associated with any relevant information in a database, such that sequencing the barcode locus and querying the database will provide information about each cell. For example, the barcodes may be associated with genetic mutations, deletions, insertions, substitutions, translocations, epigenetic modifications, addition of a transgene, modification of regulatory sequences, DNA assemblies, artificial chromosomes, functional guide RNA sequences constructs for CRISPR interference, or any other information.

In one aspect is provided a method for compressing polynucleotide information into a single barcode in a cell. In embodiments, the method includes obtaining a cell comprising at least two unique polynucleotide barcodes in a barcode locus; inserting a new unique polynucleotide barcode in the barcode locus of the cell; and sequencing the barcode locus such that the new unique polynucleotide barcode (compressor barcode) is associated with the at least two unique polynucleotide barcodes. In embodiments, the method further includes removing the at least two unique polynucleotide barcodes from the barcode locus of the cell. This process can be referred to as "barcode compression."

In one aspect a plurality of gene edited and barcoded cells that were made by a method described herein is provided.

In one aspect a gene edited and barcoded cell that was made by a method described herein is provided.

In embodiments, each unique polynucleotide barcode is added adjacent to the previous unique polynucleotide barcode in the barcode locus. In embodiments, each unique polynucleotide barcode is added upstream of the previous unique polynucleotide barcode in the barcode locus. In embodiments, each unique polynucleotide barcode is added downstream of the previous unique polynucleotide barcode in the barcode locus.

In embodiments, each unique polynucleotide barcode is flanked on the recombinant polynucleotide by a right homology arm and/or a left homology arm. In embodiments, each first unique polynucleotide barcode is flanked on each recombinant polynucleotide of the first plurality of polynucleotides by a first right homology arm, a second right homology arm, and a left homology arm, such that the first right homology arm and the left homology arm are homologous to a sequence at the barcode locus. The second right homology arm is situated in between the first right homology arm and the left homology arm such that it integrates with the first unique polynucleotide barcode at the barcode locus. In embodiments, each second unique polynucleotide barcode is flanked on each recombinant polynucleotide of the second plurality of polynucleotides by the second right homology arm, the left homology arm, and optionally a third right homology arm, such that the second right homology arm and the left homology arm are homologous to a sequence at the barcode locus after integration of the first unique polynucleotide barcode into the barcode locus.

In embodiments, each recombinant polynucleotide of the first plurality of polynucleotides comprises a first marker polynucleotide between the left homology arm and the second right homology arm. In embodiments, each recombinant polynucleotide of the second plurality of polynucleotides comprises a second marker polynucleotide between the left homology arm and the third right homology arm. In embodiments, the marker polynucleotide is incorporated into the barcode locus with the unique polynucleotide barcode. In embodiments, each recombinant polynucleotide further comprises a marker polynucleotide. In embodiments, the marker polynucleotide is incorporated into the barcode locus with the unique polynucleotide barcode. In embodiments, the method includes selecting cells for presence of the marker polynucleotide. In embodiments, the method includes selecting cells for absence of the marker polynucleotide. In embodiments, the marker polynucleotide in the first plurality of recombinant polynucleotides is different from the marker polynucleotide in the second plurality of recombinant polynucleotides.

The polynucleotide (and optionally any associated sequences, e.g. a marker sequence, homology arms, etc.) may be inserted into the barcode locus by any means. In embodiments, each unique polynucleotide barcode is inserted in the barcode locus by homologous recombination. In embodiments, each unique polynucleotide barcode is inserted in the barcode locus by non-homologous end joining. In embodiments, each unique polynucleotide barcode is inserted in the barcode locus using an integrase. In embodiments, each unique polynucleotide barcode is inserted in the barcode locus using a transposase.

In embodiments, the first gene editing agent is a meganuclease, zinc finger nuclease (ZFN), transcription activator-like effector-based nuclease (TALEN), RNA-guided nuclease, a chemical agent, a recombinase, an integrase, or a transposase. In embodiments, the second gene editing agent is a meganuclease, zinc finger nuclease (ZFN), transcription activator-like effector-based nuclease (TALEN), clustered regularly interspaced short palindromic repeats (CRISPR) system, a chemical agent, a recombinase, an integrase, or a transposase. In embodiments, the first and/or second gene editing agent is a RNA-guided nuclease. In embodiments, the first gene editing agent is a CRISPR system. In embodiments, the first gene editing agent is a CRISPR/Cas9 system. In embodiments, the first gene editing agent is a CRISPR/Cas12a system. In embodiments, the second gene editing agent is a CRISPR system. In embodiments, the second gene editing agent is a CRISPR/Cas9 system. In embodiments, the second gene editing agent is a CRISPR/Cas12a system.

In embodiments, the first gene editing agent and the second gene editing agent are the same. In embodiments, the first gene editing agent and the second gene editing agent are different.

In embodiments, the method includes sequencing at least a portion of the chromosome of a cell from the first plurality of gene edited and barcoded cells. In embodiments, the method includes sequencing at least a portion of the chromosome of a cell from the second plurality of gene edited and barcoded cells. In embodiments, the barcode locus is sequenced. In embodiments, at least one genetic modification is determined by sequencing.

In embodiments, the method includes identifying at least one genetic modification with a unique polynucleotide barcode.

In embodiments, the method includes (i) inserting a new unique polynucleotide barcode in the barcode locus of each cell, wherein the barcode locus comprises at least two unique polynucleotide barcodes prior to insertion of the new unique polynucleotide barcode. In embodiments, the method includes (ii) sequencing the barcode locus such that the new unique polynucleotide barcode is associated with the at least two unique polynucleotide barcodes. In embodiments, the method includes (iii) removing the at least two unique polynucleotide barcodes from the barcode locus of each cell. In embodiments, the method includes repeating the genetic modification/barcoding steps (e.g., steps (a), (b), (c), and/or (d)), thereby producing a plurality of genetically engineered cells.

In embodiments, each recombinant polynucleotide is provided by a vector. In embodiments, the vector is a plasmid vector or a viral vector. In embodiments, the vector is a high copy number vector. In certain embodiments, each recombinant polynucleotide is provided as linear DNA. In certain embodiments, each recombinant polynucleotide on the linear or vector DNA is operably linked to an RNA polymerase promoter to enable transcription in the host cell and is operably linked with RNA sequence elements to enable reverse-transcription of the recombinant RNA to generate single-stranded donor DNA. Methods to generate single-stranded DNA are known to those of ordinary skill in the art and include the use of a bacterial retron system (e.g. Ec86 retron) or viral reverse transcriptase (e.g. Moloney mouse leukemia viral reverse transcriptase). For example, the method may further comprise amplifying a recombinant polynucleotide comprising a genome editing cassette, which is provided as a PCR product.

In embodiments, the barcode locus is a chromosomal barcode locus.

In embodiments, the genetic modification is a designed genetic modification.

Importantly, the barcodes described herein are not restricted to associations with CRISPR genome editing constructs, but have broader applications for any genetic modification process that yields known or unknown genetic changes, or for storage and compression of arbitrary digital information in DNA. Non-limiting examples of such applications include genome modification, genetic constructs, epigenetic modification, and lineage tracing (FIG. 1A).

Gene editing agents are known in the art. Gene editing agents may be agents that cause directed (designed) gene modifications, or physical and chemical agents that cause spontaneous (random) gene mutation (e.g., mutagens). In embodiments, the gene editing agent is a meganuclease, zinc finger nuclease (ZFN), transcription activator-like effector-based nuclease (TALEN), RNA-guided nuclease, heat, radiation, a chemical agent, a recombinase, an integrase, or a transposase.

In embodiments, the gene editing agent is a RNA-guided nuclease. In embodiments, the RNA-guided nuclease is a CRISPR system. In embodiments, the RNA-guided nuclease is a CRISPR/Cas system. In embodiments, the RNA-guided nuclease is a CRISPR/Cas9 system. In embodiments, the RNA-guided nuclease is a CRISPR/Cas12a system. In embodiments, the CRISPR system may be any such system, including without limitation, SpCas9, SaCas9, NmCas9, St1Cas9, FnCas9, Cas12a (e.g. FnCpf1, AsCpf1, LbCpf1), Mad7, CasX, CasY, Cas13a, C2c1, C2c2, C2c3, LshC2c2, Cas14, dSpCas9-FokI, Split-SpCas9, SpCas9-nickase. Additional CRISPR systems are known, for example as described in Komor et al., Nature (2016) 533(7603):420-4, which is incorporated herein by reference in its entirety.

In embodiments, integration of a barcode at the barcode locus is performed using a site-specific recombinase system. Exemplary site-specific recombinase systems that can be used for this purpose include a Cre-loxP site-specific recombinase system, a Flp-FRT site-specific recombinase system, a PhiC31-att site-specific recombinase system, and a Dre-rox site-specific recombinase system. For a description of these and other site-specific recombinase systems that can be used, see, e.g., Wirth et al. (2007) Curr. Opin. Biotechnol. 18(5):411-419; Branda et al. (2004) Dev. Cell 6(1):7-28; Birling et al. (2009) Methods Mol. Biol. 561:245-263; Bucholtz et al. (2008) J. Vis. Exp. May 29 (15) pii: 718; Nem et al. (2011) Proc. Natl. Acad. Sci. U.S.A. 108(34):14198-14203; Smith et al. (2010) Biochem. Soc. Trans. 38(2):388-394; Turan et al. (2011) FASEB J. 25(12):4088-4107; Garcia-Otin et al. (2006) Front. Biosci. 11:1108-1136; Gaj et al. (2014) Biotechnol Bioeng. 111(1):1-15; Krappmann (2014)

Appl. Microbiol. Biotechnol. 98(5):1971-1982; Kolb et al. (2002) Cloning Stem Cells 4(1):65-80; and Lopatniuk et al. (2015) J. Appl. Genet. 56(4):547-550; herein incorporated by reference in their entireties.

A recombination target site for a site-specific recombinase may be added to the barcode locus to allow integration by site-specific recombination. In addition, the recombinant polynucleotide may be designed with a matching recombination target site for the site-specific recombinase such that site-specific recombination between the recombination target site on the recombinant polynucleotide and the recombination target site at the barcode locus results in integration of the genome editing cassette at the barcode locus.

In certain embodiments, the method further comprises inhibiting non-homologous end joining (NHEJ). For example, NHEJ may be inhibited by contacting cells with a small molecule inhibitor selected from the group consisting of wortmannin and Scr7. Alternatively, RNA interference or CRISPR-interference can be used to inhibit expression of a protein component of the NHEJ pathway.

In other embodiments, the method further comprises using an HDR enhancer or active donor recruitment to increase the frequency of HDR in the cells. In certain embodiments, an inhibitor of the non-homologous end joining (NHEJ) pathway is used to further increase the frequency of cells genetically modified by HDR. Examples of inhibitors of the NHEJ pathway include any compound (agent) that inhibits or blocks either expression or activity of any protein component in the NHEJ pathway. Protein components of the NHEJ pathway include, but are not limited to, Ku70, Ku86, DNA protein kinase (DNA-PK), Rad50, MRE11, NBS1, DNA ligase IV, and XRCC4. An exemplary inhibitor is wortmannin which inhibits at least one protein component (e.g., DNA-PK) of the NHEJ pathway. Another exemplary inhibitor is Scr7 (5,6-bis((E)-benzylideneamino)-2-mercaptopyrimidin-4-ol), which inhibits joining of DSBs (Maruyama et al. (2015) Nat. Biotechnol. 33(5):538-542, Lin et al. (2016) Sci. Rep. 6:34531). RNA interference or CRISPR-interference may also be used to block expression of a protein component of the NHEJ pathway (e.g., DNA-PK or DNA ligase IV). For example, small interfering RNAs (siRNAs), hairpin RNAs, and other RNA or RNA:DNA species which can be cleaved or dissociated in vivo to form siRNAs may be used to inhibit the NHEJ pathway by RNA interference. Alternatively, deactivated Cas9 (dCas9) together with single guide RNAs (sgRNAs) complementary to the promoter or exonic sequences of genes of the NHEJ pathway can be used in transcriptional repression by CRISPR-interference. Alternatively, an HDR enhancer such as RS-1 may be used to increase the frequency of HDR in cells (Song et al. (2016) Nat. Commun. 7:10548).

Genome editing may be performed on a single cell or a population of cells of interest and can be performed on any type of cell, including any cell from a prokaryotic, eukaryotic, or archaeon organism, including bacteria, archaea, fungi, protists, plants, and animals. Cells from tissues, organs, and biopsies, as well as recombinant cells, genetically modified cells, cells from cell lines cultured in vitro, and artificial cells (e.g., nanoparticles, liposomes, polymersomes, or microcapsules encapsulating nucleic acids) may all be used in the practice of the methods and compositions described herein. The methods described herein are also applicable to editing of nucleic acids in cellular fragments, cell components, or organelles comprising nucleic acids (e.g., mitochondria in animal and plant cells, plastids (e.g., chloroplasts) in plant cells and algae). Cells may be cultured or expanded prior to or after performing genome editing as described herein. In one embodiment, the cells are yeast cells.

RNA-Guided Nuclease Systems

In embodiments, each recombinant polynucleotide further comprises a third polynucleotide encoding a RNA-guided nuclease. In embodiments, each recombinant polynucleotide further comprises a donor polynucleotide. In embodiments, the RNA-guided nuclease is provided by a vector. In embodiments, the RNA-guided nuclease is provided by a second nucleic acid sequence integrated into the genome of the cells. In embodiments, the RNA-guided nuclease is a Cas nuclease or an engineered RNA-guided FokI-nuclease. In embodiments, the Cas nuclease is Cas9 or Cas12a. In embodiments, the RNA-guided nuclease is provided on the same recombinant polynucleotide as the unique barcode sequence. In embodiments, a donor polynucleotide (e.g., donor DNA) and/or a polynucleotide encoding a guide RNA (gRNA) is incorporated into each cell. In embodiments, the gRNA is capable of hybridizing at a genomic target locus to be modified. In embodiments, the donor polynucleotide comprising a 5' homology arm that hybridizes to a 5' genomic target sequence and a 3' homology arm that hybridizes to a 3' genomic target sequence flanking a nucleotide sequence comprising an intended edit to be integrated into the genomic target locus. In embodiments, each recombinant polynucleotide comprises a different genome editing cassette comprising a different guide RNA-donor polynucleotide combination, such that the plurality of recombinant polynucleotides is capable of producing a plurality of different intended edits at one or more genomic target loci. In embodiments, the RNA-guided nuclease creates double-stranded breaks in the genomic DNA of the cells at the one or more genomic target loci, and the donor polynucleotide present in each cell is integrated at the genomic target locus recognized by its 5' homology arm and 3' homology arm by homology directed repair (HDR) such that a plurality of genetically modified cells are produced.

In embodiments, each recombinant polynucleotide is provided by a vector. In embodiments, the vector is a plasmid vector or a viral vector. In embodiments, the vector is a high copy number vector. In certain embodiments, each recombinant polynucleotide is provided as linear DNA. For example, the method may further comprise amplifying a recombinant polynucleotide comprising a genome editing cassette, which is provided as a PCR product.

In certain embodiments, the RNA-guided nuclease is also provided by a vector. In certain embodiments, the genome editing cassette and the RNA-guided nuclease are provided by a single vector or separate vectors. In another embodiment, a recombinant polynucleotide encoding the RNA-guided nuclease is integrated into the genome of the host cells.

Transcription of a guide RNA will generally depend on the presence of a promoter, which may be included in the genome editing cassette, or in a vector or at a genomic locus (e.g., the barcode locus) in which the genome editing cassette is inserted. The promoter may be a constitutive or an inducible promoter. In certain embodiments, each genome editing cassette comprises a promoter operably linked to the polynucleotide encoding the guide RNA. In other embodiments, the barcode locus comprises a promoter that becomes operably linked to the polynucleotide encoding the guide RNA of any genome editing cassette that integrates at the barcode locus. In another embodiment, each recombinant polynucleotide is provided by a vector, wherein the vector comprises a promoter that is operably linked to the polynucleotide encoding the guide RNA. In certain embodiments, the guide RNA and/or donor DNA cassette integrate into the barcode locus along with the recombinant polynucleotide barcode. In other embodiments, only the polynucleotide barcode integrates into the barcode locus.

In certain embodiments, the gene editing agent (optionally in combination with the donor polynucleotide and/or guide RNA) is capable of producing mutations at multiple sites within a single gene. In other embodiments, the gene editing agent is capable of producing mutations at multiple sites in different genes or anywhere in the genome. For example, a gene editing agent (e.g., donor polynucleotide) may introduce a different mutation into a gene, such as an insertion, deletion, or substitution. In another embodiment, at least one gene editing agent (e.g., donor polynucleotide) introduces a mutation that inactivates a gene. In another embodiment, at least one gene editing agent (e.g., donor polynucleotide) removes a mutation from a gene. In another embodiment, at least one gene editing agent (e.g., donor polynucleotide) inserts a precise genetic change into the genomic DNA.

In certain embodiments, each recombinant polynucleotide further comprises a pair of restriction sites flanking a genome editing cassette. In some embodiments, the restriction sites are recognized by a meganuclease (e.g., SceI) that generates a DNA double-strand break. The expression of the meganuclease may be controlled by an inducible promoter.

In another embodiment, the genome editing cassette further comprises a tRNA gene at the 5' end of the nucleotide sequence encoding the guide RNA.

In another embodiment, the genome editing cassette further comprises a nucleotide sequence encoding a hepatitis delta virus (HDV) ribozyme at the 5' end of the nucleotide sequence encoding the guide RNA. In another embodiment, the genome editing cassette further comprises a nucleotide sequence encoding a Hammerhead Ribozyme (HHR) at the 5' end of the nucleotide sequence encoding the guide RNA adjacent to the promoter of RNA polymerase II or RNA polymerase III. In another embodiment, the genome editing cassette further comprises a nucleotide sequence encoding a ribozyme, for example CPEB3, PMAR1, or RiboJ.

In another embodiment, the RNA-guided nuclease is a Cas nuclease (e.g., Cas9 or Cas12a) or an engineered RNA-guided FokI-nuclease.

In another embodiment, the genome editing cassette is flanked by restriction sites recognized by a meganuclease.

In embodiments, each genome editing cassette further comprises the unique barcode sequence for identifying the guide RNA and the donor polynucleotide encoded by each genome editing cassette. In an embodiment, the method further comprises deleting the polynucleotide encoding the guide RNA and the donor polynucleotide integrated at the barcode locus while retaining the unique barcode at said barcode locus that represents the deleted sequences. In another embodiment, the method further comprises sequencing the barcode at the barcode locus of at least one genetically modified cell to identify the genome editing cassette used in genetically modifying said cell.

In certain embodiments, the method further comprises sequencing each genome editing cassette. Sequencing of a genome editing cassette to link a barcode to a particular gRNA-donor polynucleotide combination may be performed, for example, at an intermediate cloning step prior to ligation of a genome editing cassette into a vector or prior to transfecting cells. Alternatively or additionally, sequencing of a genome editing cassette that has been integrated at the barcode locus may be used to determine genome edits performed on a genetically modified cell.

An RNA-guided nuclease can be targeted to a particular genomic sequence (i.e., genomic target sequence to be modified) by altering its guide RNA sequence. A target-specific guide RNA comprises a nucleotide sequence that is complementary to a genomic target sequence, and thereby mediates binding of the nuclease-gRNA complex by hybridization at the target site. For example, the gRNA can be designed with a sequence complementary to the sequence of a minor allele to target the nuclease-gRNA complex to the site of a mutation. The mutation may comprise an insertion, a deletion, or a substitution. For example, the mutation may include a single nucleotide variation, gene fusion, translocation, inversion, duplication, frameshift, missense, nonsense, or other mutation associated with a phenotype or disease of interest. The targeted minor allele may be a common genetic variant or a rare genetic variant. In certain embodiments, the gRNA is designed to selectively bind to a minor allele with single base-pair discrimination, for example, to allow binding of the nuclease-gRNA complex to a single nucleotide polymorphism (SNP). In particular, the gRNA may be designed to target disease-relevant mutations of interest for the purpose of genome editing to remove the mutation from a gene. Alternatively, the gRNA can be designed with a sequence complementary to the sequence of a major or wild-type allele to target the nuclease-gRNA complex to the allele for the purpose of genome editing to introduces a mutation into a gene in the genomic DNA of the cell, such as an insertion, deletion, or substitution. Such genetically modified cells can be used, for example, to alter phenotype, confer new properties, or produce disease models for drug screening.

In certain embodiments, the RNA-guided nuclease used for genome modification is a clustered regularly interspersed short palindromic repeats (CRISPR) system Cas nuclease. Any RNA-guided Cas nuclease capable of catalyzing site-directed cleavage of DNA to allow integration of donor polynucleotides by the HDR mechanism can be used in genome editing, including CRISPR system type I, type II, or type III Cas nucleases. Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, Cas12a, Mad7, CasX, CasY, Cas13a, Cas14, C2c1, C2c2, C2c3, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

In certain embodiments, a type II CRISPR system Cas9 endonuclease is used. Cas9 nucleases from any species, or biologically active fragments, variants, analogs, or derivatives thereof that retain Cas9 endonuclease activity (i.e., catalyze site-directed cleavage of DNA to generate double-strand breaks) may be used to perform genome modification as described herein. The Cas9 need not be physically derived from an organism, but may be synthetically or recombinantly produced. Cas9 sequences from a number of bacterial species are well known in the art and listed in the National Center for Biotechnology Information (NCBI) database. See, for example, NCBI entries for Cas9 from: *Streptococcus pyogenes* (WP_002989955, WP_038434062, WP_011528583); *Campylobacter jejuni* (WP_022552435, YP_002344900), *Campylobacter coli* (WP_060786116); *Campylobacter fetus* (WP_059434633); *Corynebacterium*

*ulcerans* (NC_015683, NC_017317); *Corynebacterium diphtheria* (NC 016782, NC_016786); *Enterococcus faecalis* (WP_033919308); *Spiroplasma syrphidicola* (NC_021284); *Prevotella intermedia* (NC 017861); *Spiroplasma taiwanense* (NC_021846); *Streptococcus iniae* (NC_021314); *Belliella baltica* (NC_018010); *Psychroflexus torquisI* (NC_018721); *Streptococcus thermophilus* (YP_820832), *Streptococcus mutans* (WP_061046374, WP_024786433); *Listeria innocua* (NP 472073); *Listeria monocytogenes* (WP_061665472); *Legionella pneumophila* (WP 062726656); *Staphylococcus aureus* (WP_001573634); *Francisella tularensis* (WP_032729892, WP_014548420), *Enterococcus faecalis* (WP_033919308); *Lactobacillus rhamnosus* (WP_048482595, WP_032965177); and *Neisseria meningitidis* (WP_061704949, YP_002342100); all of which sequences (as entered by the date of filing of this application) are herein incorporated by reference. Any of these sequences or a variant thereof comprising a sequence having at least about 70-100% sequence identity thereto, including any percent identity within this range, such as 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity thereto, can be used for genome editing, as described herein. See also Fonfara et al. (2014) Nucleic Acids Res. 42(4):2577-90; Kapitonov et al. (2015) J. Bacteriol. 198(5):797-807, Shmakov et al. (2015) Mol. Cell. 60(3):385-397, and Chylinski et al. (2014) Nucleic Acids Res. 42(10):6091-6105); for sequence comparisons and a discussion of genetic diversity and phylogenetic analysis of Cas9.

The CRISPR-Cas system naturally occurs in bacteria and archaea where it plays a role in RNA-mediated adaptive immunity against foreign DNA. The bacterial class 2 type II CRISPR system uses the endonuclease, Cas9, which forms a complex with a guide RNA (gRNA) that specifically hybridizes to a complementary genomic target sequence, where the Cas9 endonuclease catalyzes cleavage to produce a double-stranded break. Targeting of Cas9 typically further relies on the presence of a protospacer-adjacent motif (PAM) in the DNA directly 3' of the gRNA-binding site.

The genomic target site will typically comprise a nucleotide sequence that is complementary to the gRNA, and may further comprise a protospacer adjacent motif (PAM). In certain embodiments, the target site comprises 20-30 base pairs in addition to a 3 base pair PAM in the case of Cas9 from *S. pyogenes* (SpCas9). Typically, the first nucleotide of a PAM can be any nucleotide, while the two other nucleotides will depend on the specific SpCas9 variant that is chosen. Exemplary PAM sequences are known to those of skill in the art and include, without limitation, NNG, NGN, NAG, and NGG, wherein N represents any nucleotide. In certain embodiments, the allele targeted by a gRNA comprises a mutation that creates a PAM within the allele, wherein the PAM promotes binding of the Cas9-gRNA complex to the allele.

In certain embodiments, the gRNA is 5-50 nucleotides, 10-30 nucleotides, 15-25 nucleotides, 18-22 nucleotides, or 19-21 nucleotides in length, or any length between the stated ranges, including, for example, 10, 11, 12, 13, 14, 15, 16, 17, 18, 19, 20, 21, 22, 23, 24, 25, 26, 27, 28, 29, 30, 31, 32, 33, 34, or 35 nucleotides in length. The guide RNA may be a single guide RNA comprising crRNA and tracrRNA sequences in a single RNA molecule, or the guide RNA may comprise two RNA molecules with crRNA and tracrRNA sequences residing in separate RNA molecules.

In another embodiment, the CRISPR nuclease from *Prevotella* and *Francisella* 1 (Cpf1/Cas12a) may be used.

Cas12a is a class 2 type V CRISPR/Cas system RNA-guided nuclease with similarities to Cas9 and may be used analogously. Unlike Cas9, Cas12a does not require a tracrRNA and only depends on a crRNA in its guide RNA, which provides the advantage that shorter guide RNAs can be used with Cas12a for targeting than Cas9. Cas12a is capable of cleaving either DNA or RNA. The PAM sites recognized by Cas12a have the sequences 5'-YTN-3' (where "Y" is a pyrimidine and "N" is any nucleobase) or more commonly 5'-TTTV-3' (where "V" is any base but T), in contrast to the G-rich PAM site recognized by Cas9. Cas12a cleavage of DNA produces double-stranded breaks with sticky-ends having a 4 or 5 nucleotide overhang. For a discussion of Cas12a, see, e.g., Ledford et al. (2015) Nature. 526 (7571): 17-17, Zetsche et al. (2015) Cell. 163 (3):759-771, Murovec et al. (2017) Plant Biotechnol. J. 15(8):917-926, Zhang et al. (2017) Front. Plant Sci. 8:177, Femandes et al. (2016) Postepy Biochem. 62(3):315-326; herein incorporated by reference.

C2c1 is another class 2 type V CRISPR/Cas system RNA-guided nuclease that may be used. C2c1, similarly to Cas9, depends on both a crRNA and tracrRNA for guidance to target sites. For a description of C2c1, see, e.g., Shmakov et al. (2015) Mol Cell. 60(3):385-397, Zhang et al. (2017) Front Plant Sci. 8:177; herein incorporated by reference.

In yet another embodiment, an engineered RNA-guided FokI nuclease may be used. RNA-guided FokI nucleases comprise fusions of inactive Cas9 (dCas9) and the FokI endonuclease (FokI-dCas9), wherein the dCas9 portion confers guide RNA-dependent targeting on FokI. For a description of engineered RNA-guided FokI nucleases, see, e.g., Havlicek et al. (2017) Mol. Ther. 25(2):342-355, Pan et al. (2016) Sci Rep. 6:35794, Tsai et al. (2014) Nat Biotechnol. 32(6):569-576; herein incorporated by reference.

The RNA-guided nuclease can be provided in the form of a protein, such as the nuclease complexed with a gRNA, or provided by a nucleic acid encoding the RNA-guided nuclease, such as an RNA (e.g., messenger RNA) or DNA (expression vector). Codon usage may be optimized to improve production of an RNA-guided nuclease in a particular cell or organism. For example, a nucleic acid encoding an RNA-guided nuclease can be modified to substitute codons having a higher frequency of usage in a yeast cell, a bacterial cell, a human cell, a non-human cell, a mammalian cell, a rodent cell, a mouse cell, a rat cell, or any other host cell of interest, as compared to the naturally occurring polynucleotide sequence. When a nucleic acid encoding the RNA-guided nuclease is introduced into cells, the protein can be transiently, conditionally, or constitutively expressed in the cell.

Donor polynucleotides and gRNAs are readily synthesized by standard techniques, e.g., solid phase synthesis via phosphoramidite chemistry, as disclosed in U.S. Pat. Nos. 4,458,066 and 4,415,732, incorporated herein by reference; Beaucage et al., Tetrahedron (1992) 48:2223-2311; and Applied Biosystems User Bulletin No. 13 (1 Apr. 1987). Other chemical synthesis methods include, for example, the phosphotriester method described by Narang et al., Meth. Enzymol. (1979) 68:90 and the phosphodiester method disclosed by Brown et al., Meth. Enzymol. (1979) 68:109. In view of the short lengths of gRNAs (typically about 20 nucleotides in length) and donor polynucleotides (typically about 100-150 nucleotides), gRNA-donor polynucleotide cassettes can be produced by standard oligonucleotide synthesis techniques and subsequently ligated into vectors. Moreover, libraries of gRNA-donor polynucleotide cassettes directed against thousands of genomic targets can be readily created using highly parallel array-based oligonucleotide library synthesis methods (see, e.g., Cleary et al. (2004) Nature Methods 1:241-248, Svensen et al. (2011) PLoS One 6(9):e24906).

In addition, adapter sequences can be added to oligonucleotides to facilitate high-throughput amplification or sequencing. For example, a pair of adapter sequences can be added at the 5' and 3' ends of an oligonucleotide to allow amplification or sequencing of multiple oligonucleotides simultaneously by the same set of primers. Additionally, restriction sites can be incorporated into oligonucleotides to facilitate cloning of oligonucleotides into vectors. For example, oligonucleotides comprising gRNA-donor polynucleotide cassettes can be designed with a common 5' restriction site and a common 3' restriction site to facilitate ligation into the genome modification vectors. A restriction digest that selectively cleaves each oligonucleotide at the common 5' restriction site and the common 3' restriction site is performed to produce restriction fragments that can be cloned into vectors (e.g., plasmids or viral vectors), followed by transformation of cells with the vectors comprising the gRNA-donor polynucleotide cassettes.

Amplification of polynucleotides encoding gRNA-donor polynucleotide cassettes may be performed, for example, before ligation into genome modification vectors or before sequencing and after barcoding. Any method for amplifying oligonucleotides may be used, including, but not limited to polymerase chain reaction (PCR), isothermal amplification, nucleic acid sequence-based amplification (NASBA), tranfscription mediated amplification (TMA), strand displacement amplification (SDA), and ligase chain reaction (LCR). In one embodiment, the genome editing cassettes comprise common 5' and 3' priming sites to allow amplification of the gRNA-donor polynucleotide sequences in parallel with a set of universal primers. In another embodiment, a set of selective primers is used to selectively amplify a subset of the gRNA-donor polynucleotides from a pooled mixture.

Cells that are transformed with recombinant polynucleotides comprising the genome editing cassettes may be prokaryotic cells or eukaryotic cells, and are preferably designed for high-efficiency incorporation of gRNA-donor polynucleotide libraries by transformation. Methods of introducing nucleic acids into a host cell are well known in the art. Commonly used methods of transformation include chemically induced transformation, typically using divalent cations (e.g., CaCl2)), and electroporation. See, e.g., Sambrook et al. (2001) Molecular Cloning, a laboratory manual, 3rd edition, Cold Spring Harbor Laboratories, New York, Davis et al. (1995) Basic Methods in Molecular Biology, 2nd edition, McGraw-Hill, and Chu et al. (1981) Gene 13:197; herein incorporated by reference in their entireties.

Random diffusion of intracellular donor DNA to a DNA break can be rate-limiting for homologous repair. Active donor recruitment may be used to increase the frequency of cells genetically modified by the donor DNA, by favoring HDR over competing pathways of NHEJ and cell death. The method for active donor recruitment comprises: a) introducing into a cell a fusion protein comprising a protein that selectively binds to the DNA break connected to a polypeptide comprising a nucleic acid binding domain; and b) introducing into the cell a donor polynucleotide comprising i) a nucleotide sequence sufficiently complementary to hybridize to a sequence adjacent to the DNA break, and ii) a nucleotide sequence comprising a binding site recognized by the nucleic acid binding domain of the fusion protein, wherein the nucleic acid binding domain selectively binds to the binding site on the donor polynucleotide to produce a complex between the donor polynucleotide and the fusion protein, thereby recruiting the donor polynucleotide to the DNA break and promoting HDR.

The DNA break may be created by a site-specific nuclease, such as, but not limited to, a Cas nuclease (e.g., Cas9, Cas12a, or C2c1), an engineered RNA-guided FokI nuclease, a zinc finger nuclease (ZFN), a transcription activator-like effector-based nuclease (TALEN), a restriction endonuclease, a meganuclease (e.g., I-SceI, I-CreI, or I-DmoI), a homing endonuclease, and the like. Any site-specific nuclease that selectively cleaves a sequence at the target integration site for the donor polynucleotide may be used.

The DNA break may be a single-stranded (nick) or double-stranded DNA break. If the DNA break is a single-stranded DNA break, the fusion protein used comprises a protein that selectively binds to the single-stranded DNA break, whereas if the DNA break is a double-stranded DNA break, the fusion protein used comprises a protein that selectively binds to the double-stranded DNA break.

In the fusion, the protein that selectively binds to the DNA break can be, for example, an RNA-guided nuclease, such as a Cas nuclease (e.g., Cas9 or Cas12a) or an engineered RNA-guided FokI nuclease.

Donor polynucleotides may be single-stranded or double-stranded, and may be composed of RNA or DNA. A donor polynucleotide comprising DNA can be produced from a donor polynucleotide comprising RNA, if desired, by reverse transcription using reverse transcriptase, such as in the bacterial retron system or with a viral reverse transcriptase. Depending on the type of nucleic acid binding domain in the fusion protein, the donor polynucleotide may comprise, for example, a corresponding binding site comprising an RNA sequence recognized by an RNA binding domain or a DNA sequence recognized by a DNA binding domain. For example, the fusion protein can be constructed with a LexA DNA binding domain to be matched with a corresponding LexA binding site in the donor polynucleotide. In another example, the fusion protein can be constructed with a Fkhl DNA binding domain to be matched with a corresponding Fkhl binding site in the donor polynucleotide.

In another embodiment, the fusion protein may further comprise a phosphothreonine-binding domain (e.g. FHA), wherein the donor polynucleotide is selectively recruited to a DNA break having a protein comprising a phosphorylated threonine residue located sufficiently close to the DNA break for the phosphothreonine-binding domain to bind to the phosphorylated threonine residue. The phosphothreonine-binding domain may be combined with any DNA binding domain (e.g., fusion with LexA to generate LexA-FHA) for donor recruitment.

In embodiments, each recombinant polynucleotide further comprises a second nucleic acid sequence encoding a guide RNA (e.g., guide X) capable of hybridizing with the recombinant polynucleotide. In embodiments, the guide RNA forms a complex with a nuclease in each cell such that the guide RNA-nuclease complex cleaves the recombinant polynucleotide. In embodiments, the recombinant polynucleotide is a plasmid vector and the guide RNA-nuclease complex linearizes the plasmid vector.

In embodiments, each recombinant polynucleotide further comprises a second nucleic acid sequence encoding a guide RNA (e.g., guide X) capable of hybridizing with the recombinant polynucleotide, wherein the guide RNA forms a complex with a nuclease in each cell such that the guide RNA-nuclease complex cleaves the barcode locus.

Sequence Verification

In certain embodiments, the method further comprises arraying of the plurality of genetically modified cells followed by highly parallel sequence verification of the barcode locus of each colony in the array. Examples can be found in US Patent Pub. No. 2016/0122748, which is incorporated herein by reference in its entirety. In embodiments, the method includes: a) plating the plurality of genetically modified cells in an ordered array on media suitable for growth of the genetically modified cells; b) culturing the plurality of genetically modified cells under conditions whereby each genetically modified cell produces a colony of clones in the ordered array; c) introducing a genome modification barcode from a colony in the ordered array into a barcoder cell, wherein the barcoder cell comprises a nucleic acid comprising a recombination target site for a site-specific recombinase and an adjacent barcode sequence that identifies the position of the colony in the ordered array to which the genome modification barcode corresponds; d) translocating the genome modification barcode to a position adjacent to the barcode sequence of the barcoder cell using a site-specific recombinase system, wherein site-specific recombination with the recombination target site of the barcoder cell generates a nucleic acid comprising the barcode sequence linked to the genome modification barcode; e) sequencing the nucleic acid comprising the barcode sequence of the barcoder cell linked to the genome modification barcode to identify the sequences of the genome modification barcode from the colony, wherein the barcode sequence of the barcoder cell is used to identify the position of the colony in the ordered array from which the genome modification barcode originated; and f) picking a clone comprising the genome modification barcode from the colony in the ordered array identified by the barcode of the barcoder cell. The genome editing cassette (e.g. guide RNA and the donor polynucleotides) to which the genome modification barcode corresponds can be identified from a database of genome editing cassette-barcode associations previously determined by sequencing, for example the vector on which the genome modification barcode and the genome modification cassette reside, prior to transfection. In embodiments, the method includes picking a clone comprising the genetic modification barcode(s) from the colony in the ordered array identified by the barcode of the barcoder cell. In embodiments, the method is done in parallel such that a plurality of clones are picked and sequenced.

The term "barcoder cell" refers to a cell comprising a nucleic acid comprising a barcode sequence. In one embodiment, the barcode identifies the position of a colony comprising the barcoder cells.

For example, the genetically modified cells may be haploid yeast cells and the barcoder cells may be haploid yeast cells capable of mating with the genetically modified cells, wherein introducing a genome editing cassette barcode from a genetically modified haploid yeast colony in the ordered array into a barcoder haploid yeast cell comprises mating the haploid yeast clone from the colony with the barcoder haploid yeast cell to produce a diploid yeast cell. Subsequent site-specific recombination, as described herein, generates a nucleic acid comprising the barcode sequence linked to the genome editing cassette in the diploid yeast cell. The genetically modified cells may be strain MATα and the barcoder yeast cells may be strain MATa. Alternatively, the genetically modified cells may be strain MATα and the barcoder yeast cells may be strain MATα.

In certain embodiments, the recombinase system in the barcoder cell is a Cre-loxP site-specific recombinase system, a Flp-FRT site-specific recombinase system, a PhiC31-att site-specific recombinase system, or a Dre-rox site-specific recombinase system. In one embodiment, the recombination target site of the barcoder cell comprises a loxP recombination site.

In another embodiment, the recombinase system in the barcoder cell uses a meganuclease to generate a DNA double-strand break. In another embodiment, the mega-nuclease in the barcoder cell is a galactose inducible SceI meganuclease. In another embodiment, the genome editing cassette is flanked by restriction sites recognized by the meganuclease.

In another embodiment, the method further comprises using a selectable marker that selects for clones that have undergone successful site-specific recombination.

In another embodiment, the method further comprises using a selectable marker that selects for clones that have undergone successful integration of the donor polynucle-otides at the one or more genomic target loci by HDR.

In another embodiment, the method further comprises phenotyping at least one clone in the ordered array.

In another embodiment, the method further comprises sequencing an entire genome of at least one clone in the ordered array.

In another embodiment, the method further comprises repeating steps (a)-(e) with all the colonies in the ordered array to identify the sequences of the genome editing cassette barcodes (and thus the guide RNA and the donor polynucleotide to which they correspond) for every colony in the ordered array.

In another aspect is provided an ordered array of colonies comprising clones of the genetically modified cells produced by the methods described herein, wherein the colonies are re-arrayed according to desired barcodes. In one embodiment, a single colony is picked for each unique genome editing cassette barcode identified on the original set of arrays. This enables consolidation of a library where every colony corresponds to a unique barcode of a desired genome edit. In a further embodiment, the colonies in this consolidated array can be pooled together for competitive growth experiments, with the advantage of less library bias due to a near-equal starting abundance for each barcoded strain.

Example Embodiments and Methods

Figure 1B:
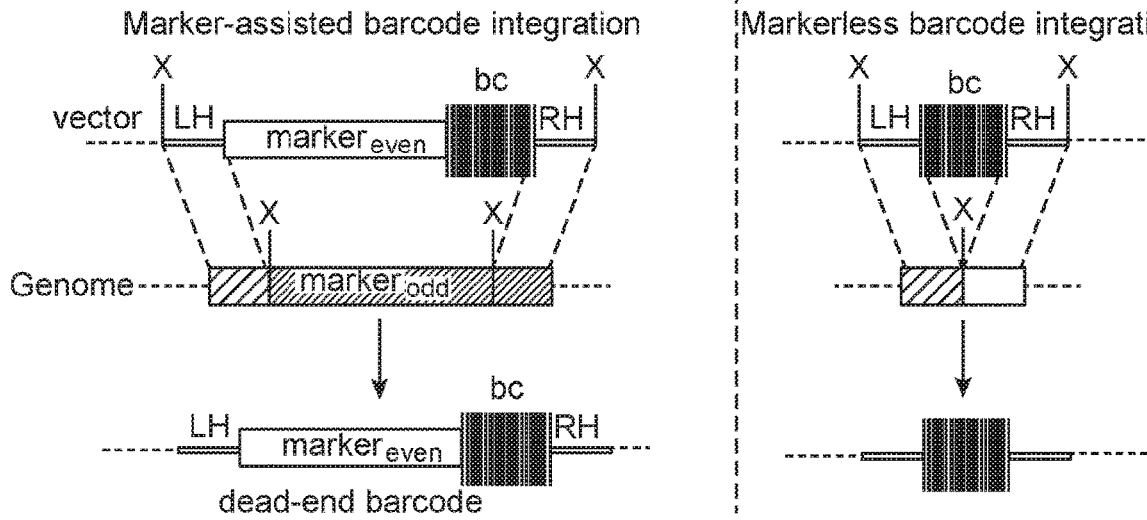
Figure 1C:
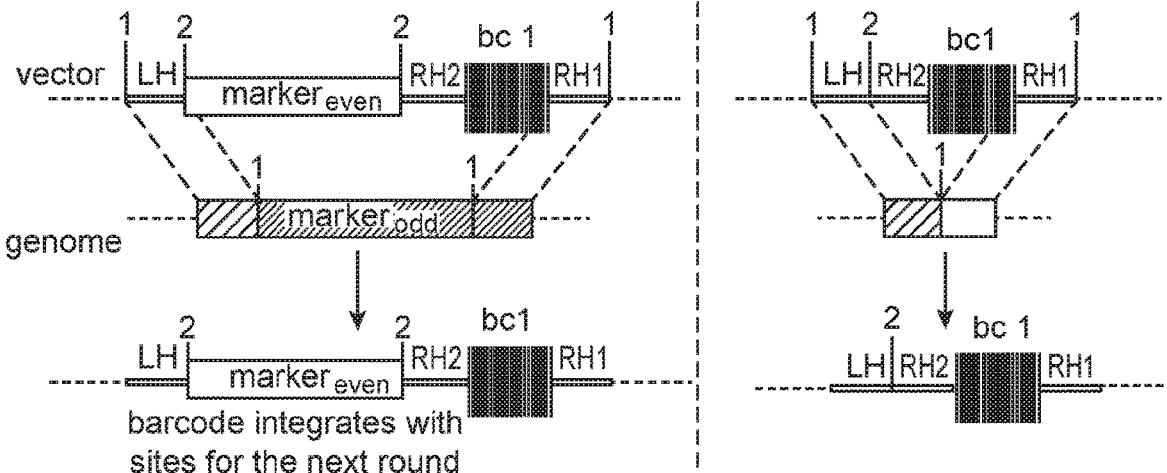
Figures 1D, 2A:
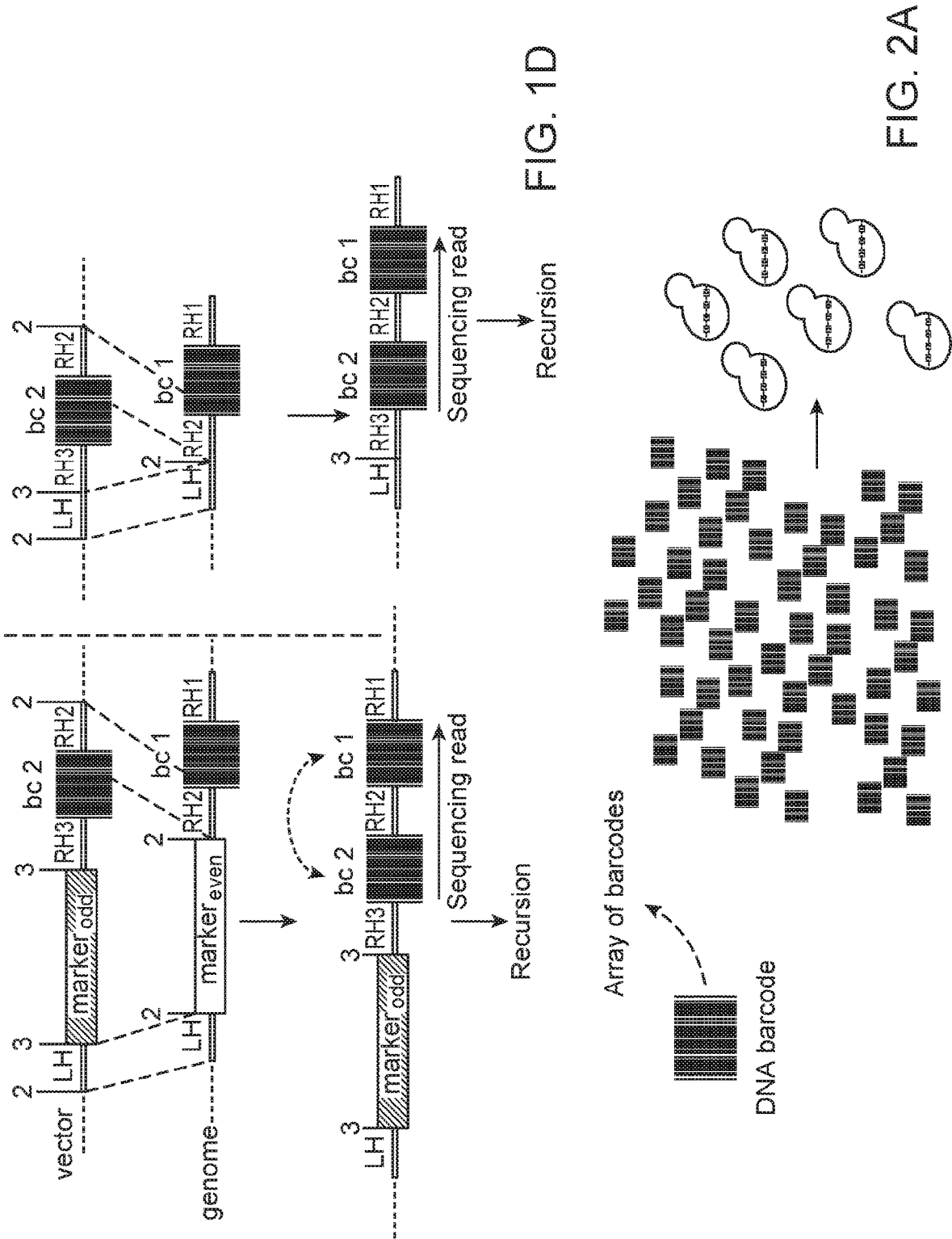
FIGS. 2A-2C show an example of barcode compression.

One principle underlying this methodology is the insertion of one barcode adjacent to another barcode, for example by homology-directed recombination (HDR), resulting in the physical linkage of the barcodes on the same DNA molecule (FIGS. 1B-1D). Multiple individual barcodes effectively combine to generate a larger single barcode, where the order of barcodes represents the order of addition of the genome edits, enabling sequencing-based approaches to identify and count barcode (i.e. variant) permutations or combinations. This disclosure builds on the barcoding system described in U.S. Provisional Application No. 62/559,493, which is incorporated herein by reference in its entirety, in several novel ways to enable subsequent rounds of barcoding.

DNA barcodes can encode a variety of changes to a cell, including those mediated by the co-delivery of known (i.e. sequenced) or unknown DNA constructs. The barcode and DNA construct can be physically linked together, such as on the same vector or amplicon, where sequencing of the vector can link the barcode with the DNA construct. The barcode can represent an unknown DNA modification(s), such as that generated by random mutagenesis or evolution-based approaches. The barcode can also point to an epigenetic modification, and can be used to track the lineage of a population of cells. Generally, the complexity of the barcode pool will be vastly greater than the complexity of the DNA or cellular population to be barcoded, such that the probability of the same barcode sequence associating with two different cells or DNA constructs will be sufficiently low.

Barcodes (and associated polynucleotide sequences) may be integrated into the barcode locus by any means. In embodiments, each unique barcode is inserted in the barcode locus by homologous recombination. In embodiments, each unique barcode is inserted in the barcode locus by non-homologous end joining. In embodiments, each unique barcode is inserted in the barcode locus using an integrase.

In embodiments, the barcodes are integrated into a barcode locus with a selectable marker. In embodiments, no selectable marker is used. FIGS. 1A-ID show examples of barcode linkage recursion, with (left side) or without (right side) the use of selectable markers. Barcoding can be enabled by host-cell homologous recombination (HR), which utilizes two homology arms, termed left homology (LH) and right homology (RH). Cleavage by a site-specific nuclease, such as an RNA guided nuclease, can be used to greatly enhance HR efficiency. Alternatively, cleavage-inde-pendent HR can be used to integrate the incoming barcode construct. The use of dual selectable/counter-selectable markers is optional and serves to remove the fraction of cells that did not incorporate the barcode at the desired locus.

Selectable markers are well known in the art. Choice of which selectable marker(s) to use depends on, for example, the type of cell (e.g., eukaryotic or prokaryotic), the cell culture system, etc., and can be determined by one of skill in the art. Selectable markers that can be used in the methods described herein include, without limitation, antibiotic resistance genes, herbicide resistance genes, antimetabolite marker genes, and reporter genes.

In embodiments, insertion of the barcode involves the co-insertion of sequence elements enabling the insertion of yet another barcode. As shown in FIG. 1C, these insertion elements may include a cleavage site 2 for a site-specific nuclease, a new right homology (RH2), and optionally, a new marker (marker$_{even}$). Round N of barcoding can be succeeded by a round N+1, with the optional marker changing during each round, for example switching back and forth between marker$_{odd}$ and marker$_{even}$ (FIG. 1D). The barcodes continue to accumulate adjacent to each other, separated by the right homology arms (RH1, RH2, RH3, etc.). The close linkage of short barcodes enables efficient and economical high-throughput sequencing approaches to track combinations of barcodes within a complex pool.

In embodiments, each round of barcoding adds a new barcode (typically 20-30 bp in length) separated by a short (typically 40-60 bp) stretch of repair homology on one side of the barcode. Continued rounds of barcode concatenation therefore add 60-90 bp. There is a practical limit to the length of the barcode array, as more than 3-5 rounds of barcoding would result in too a large construct to be tra-versed practically or economically by high-throughput sequencing. To circumvent this problem, a special round of barcoding termed "barcode compression" can be used to map multiple barcodes (for example, 4-8 barcodes) onto a single short barcode.

A DNA barcode can encode arbitrary information. This enables the barcode to represent an array of other linked barcodes, such as those that have accumulated at the barcode locus. In this setup, the barcode is not linked to anything until integration adjacent to a barcode array. As discussed above, it is advised that the complexity of the barcode pool be vastly greater than the complexity of the cellular population to be barcoded.

Figure 2B:
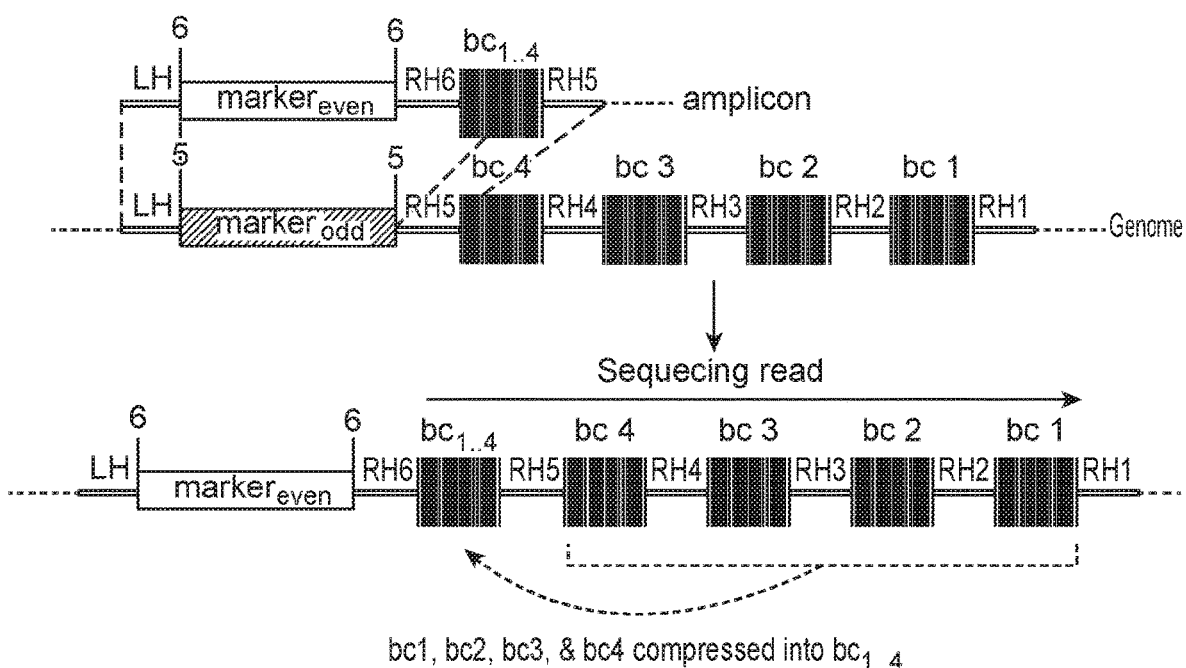
Figure 2C:
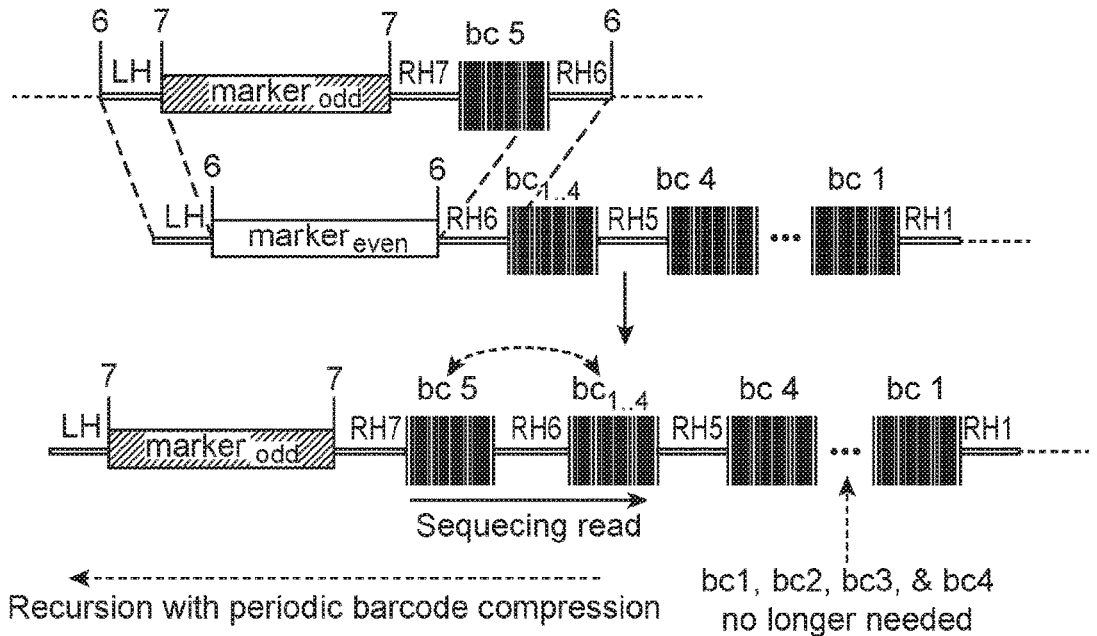

FIGS. 2A-2C shows an example of how a set of "compressor" barcodes may be inserted, enabling one long sequencing read to "compress" a set of linked barcodes onto a single compressed barcode. Thereafter, this barcode combination can be identified simply by sequencing a single barcode. FIG. 2B shows the compression of 4 barcodes into a single $bc_{1\ldots4}$. Barcode compression can be followed by further rounds of recursive barcode linkage, where barcodes that are no longer needed (and are no longer sequenced) accumulate to the right. Compression can be performed periodically to minimize the length of sequencing reads required to interrogate the population.

Figure 3A:
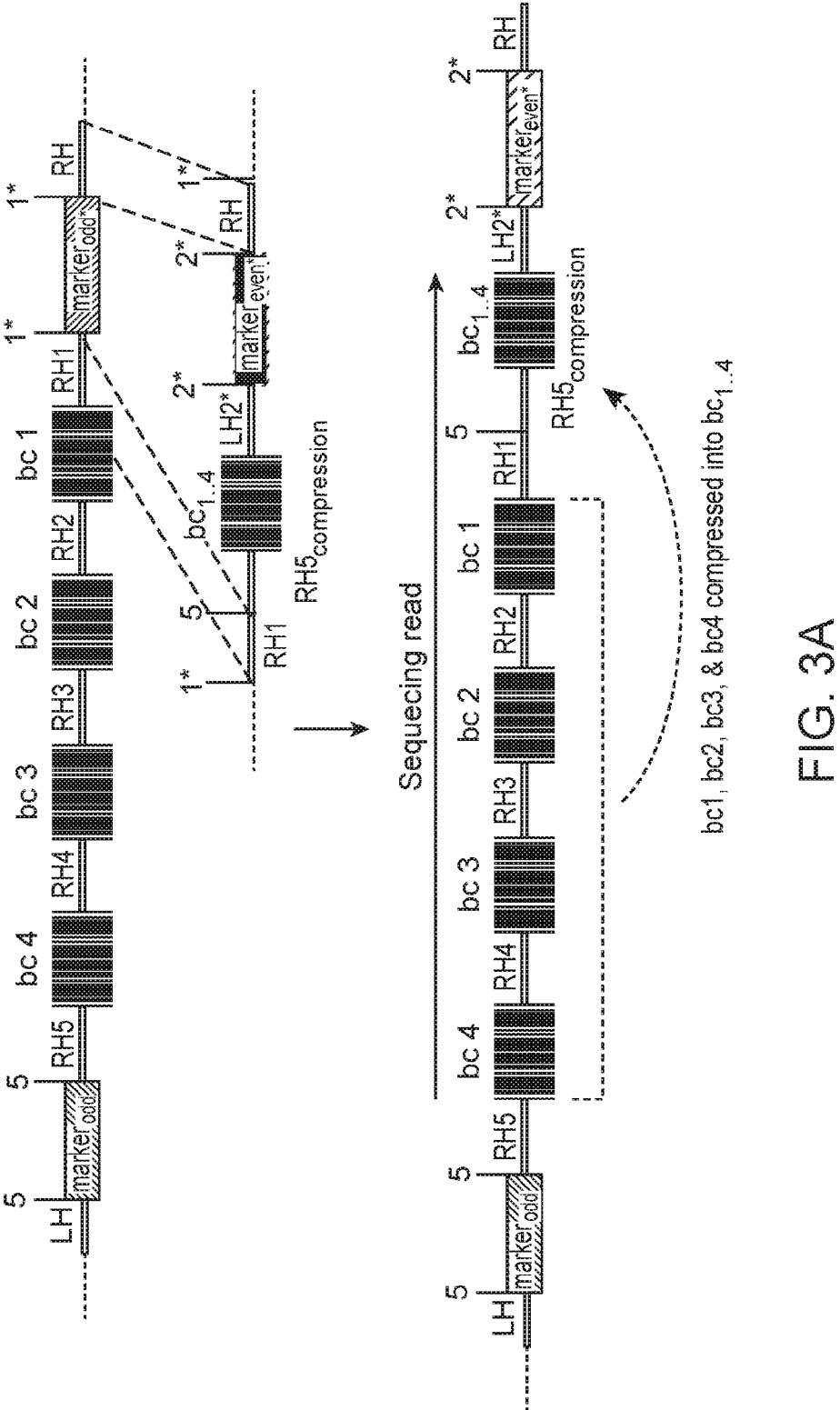
FIGS. 3A-3B show barcode compression with barcode removal and recycling of insertion elements.
Figure 3B:
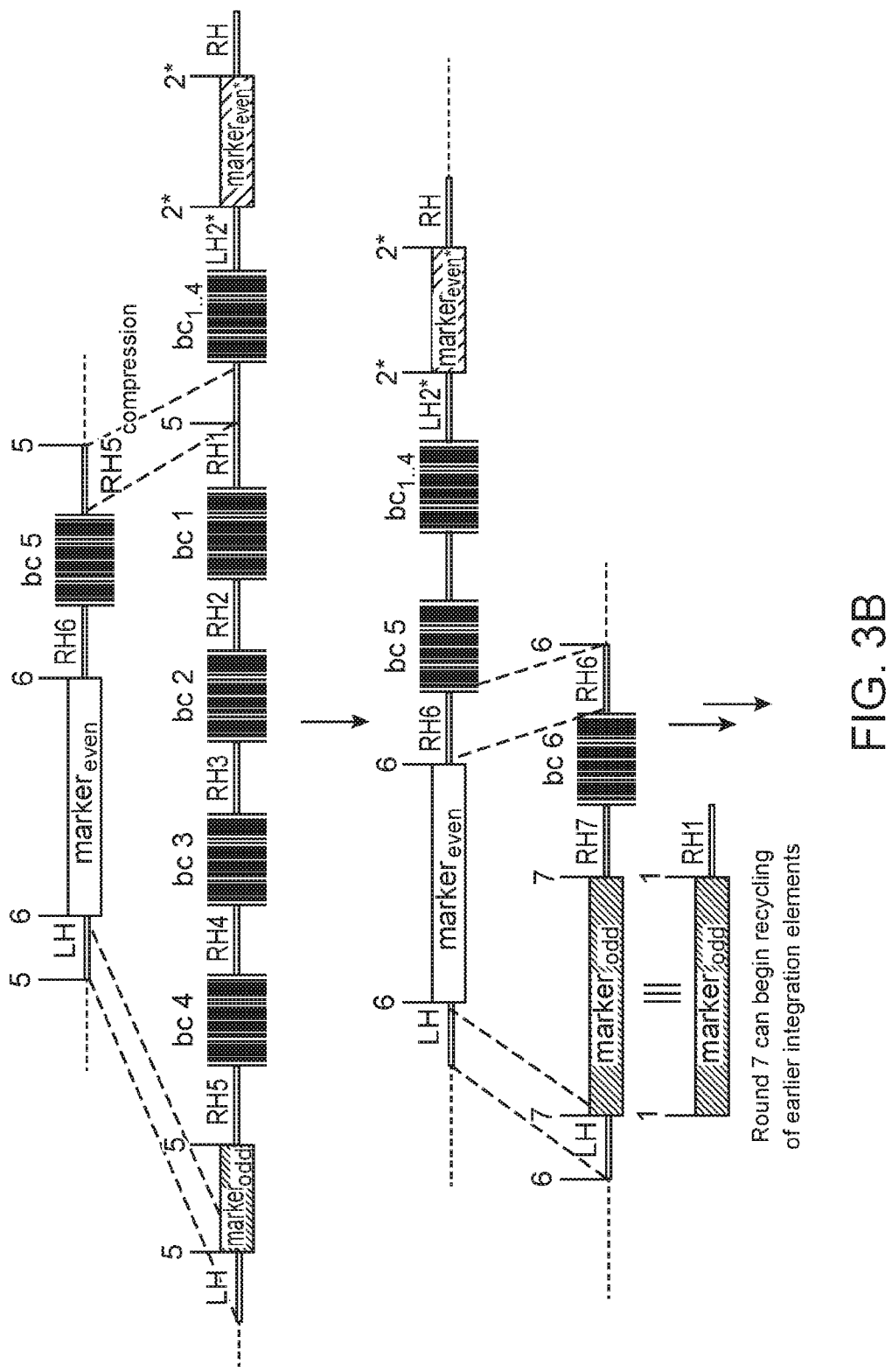

One downside of this approach is that the right homology (RH) elements cannot be re-used in subsequent rounds, due to the likelihood of unintended recombination removing sections of the barcode array. To address this, a dedicated barcode compression site can be introduced, for example to the right of the barcode locus as shown in FIG. 3A, with the use of a universal right homology (RH) and a reserved cleavage site 1*, as well as the optional aid of a different set of markers 1* and 2*. To the right of this compressed barcode, insertion elements are integrated which are reserved for a future round of barcode compression. To the left of this compressed barcode, a special homology termed $RH^{compression}$ and a N+1 cleavage site are introduced. These enable the next round of barcoding to replace bc1, bc2, bc3, and bc4, removing the old barcodes from the barcode locus. As shown in FIG. 3B, after sequencing and computational mapping of linked barcodes onto the compressed barcode, the next round of barcoding enables the removal of the linked barcodes which are no longer needed. The compressed barcode may also introduce a cleavage site and homology for a subsequent round of barcode linkage. In this example, bc5 is inserted adjacent to the left of $bc_{1\ldots4}$ and in the process removes bc1, bc2, bc3, and bc4, as well as RH1, RH2, RH3, RH4, and RH5 and their associated cleavage sites. This enables the recycling of earlier insertion elements and prevents the barcode locus from growing continuously. Like the recursive barcode linkage, this compressed barcode also optionally introduces a marker, homology and cleavage sites for a future round of compression (FIGS. 4A-4B).

Figure 4A:
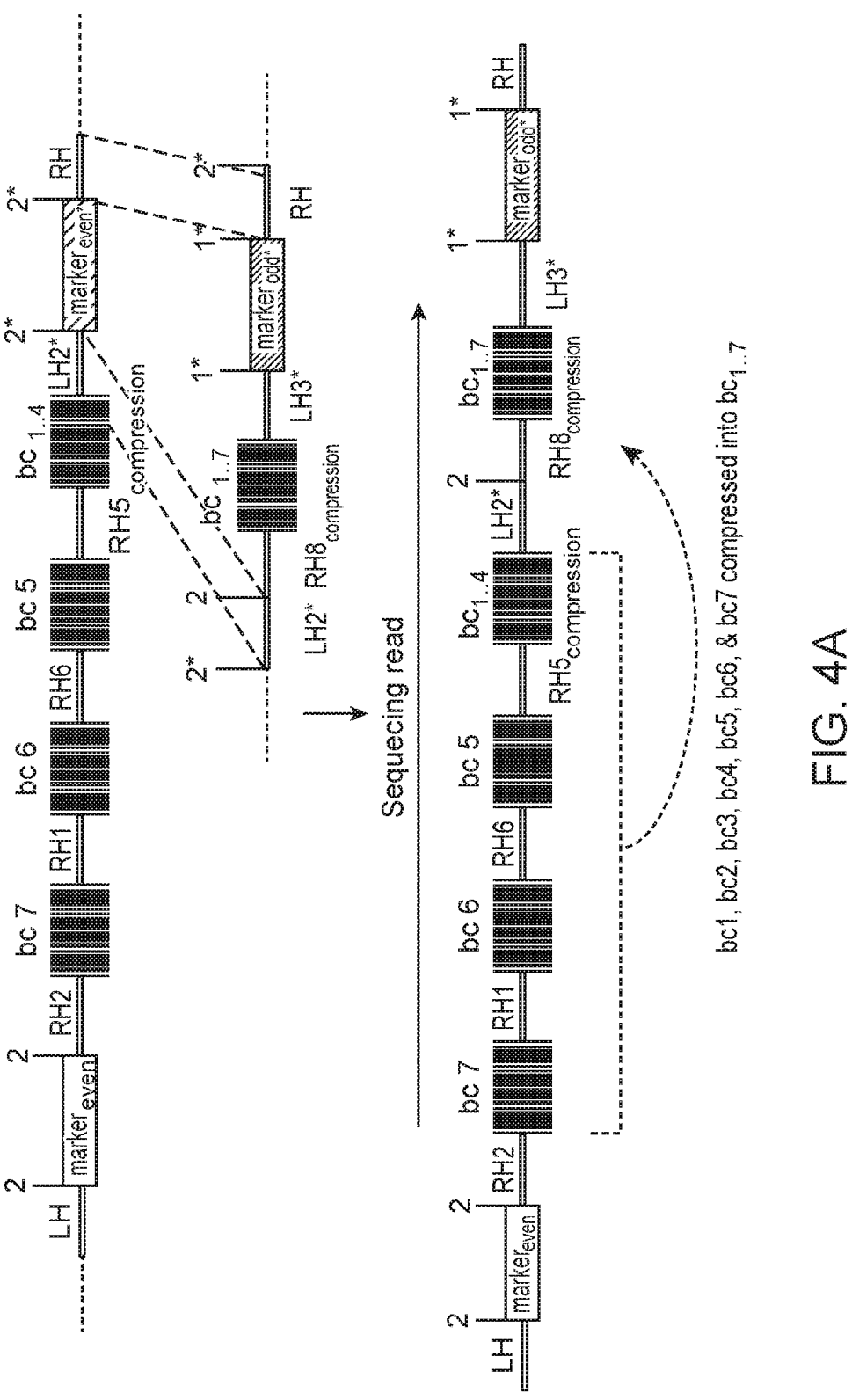
FIGS. 4A-4B show recursive barcode compression.
Figure 4B:
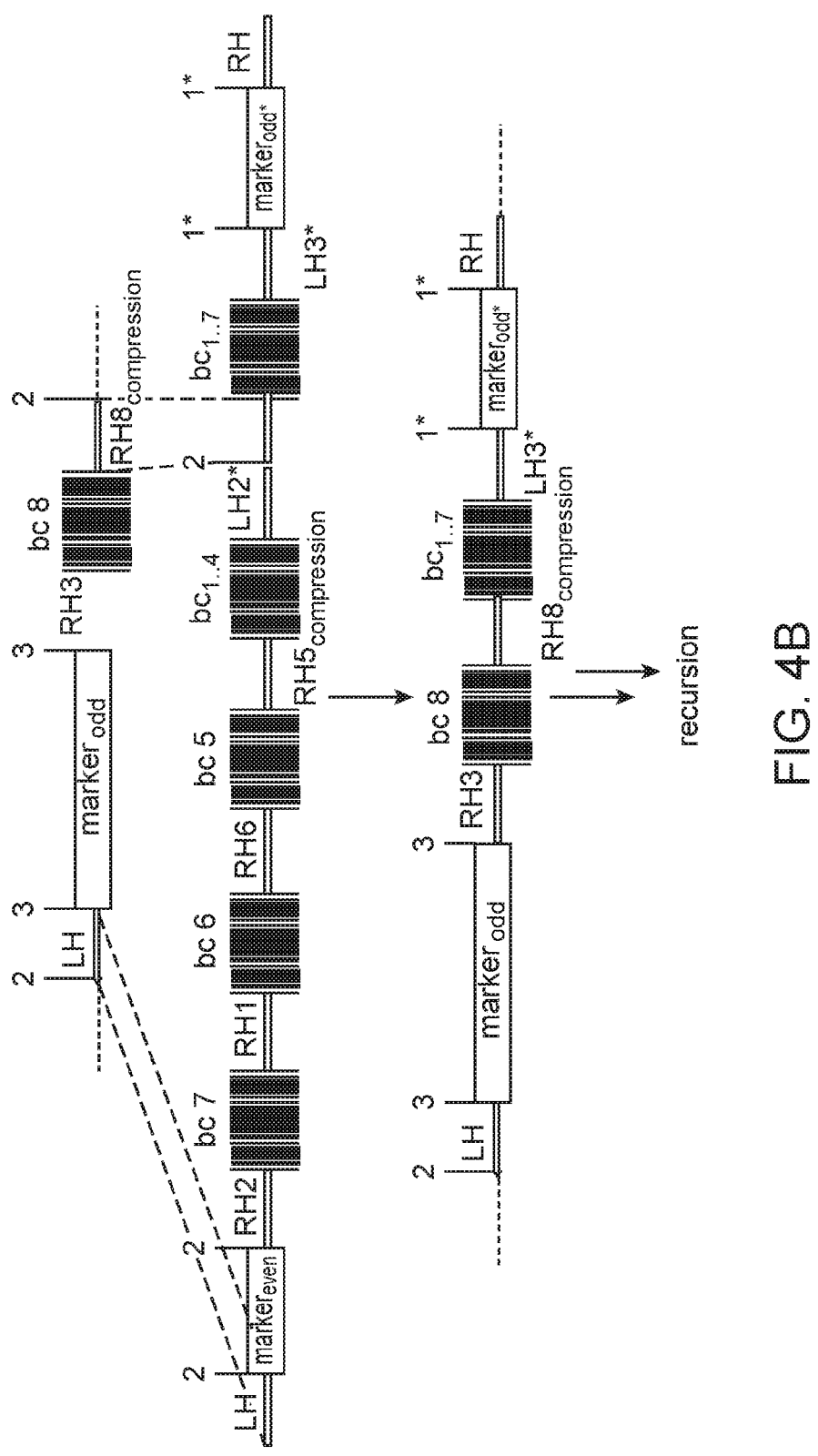

As shown in FIGS. 4A-4B, the second round of barcode compression may be structurally identical to the first round, involving the use of the same RH element but different homologies and cleavage sites for further barcode linkage to the left and barcode compression to the right. In this example round of barcode compression, the incoming barcode $bc_{1\ldots7}$ compresses both the linked barcodes bc5, bc6, and bc7 and the previously compressed $bc_{1\ldots4}$. The next round of barcode linkage to the left optionally removes bc5, bc6, and bc7 and the previously compressed $bc_{1\ldots4}$, enabling the recycling of previously used insertion elements in the next series of barcoding rounds.

Figure 5A:
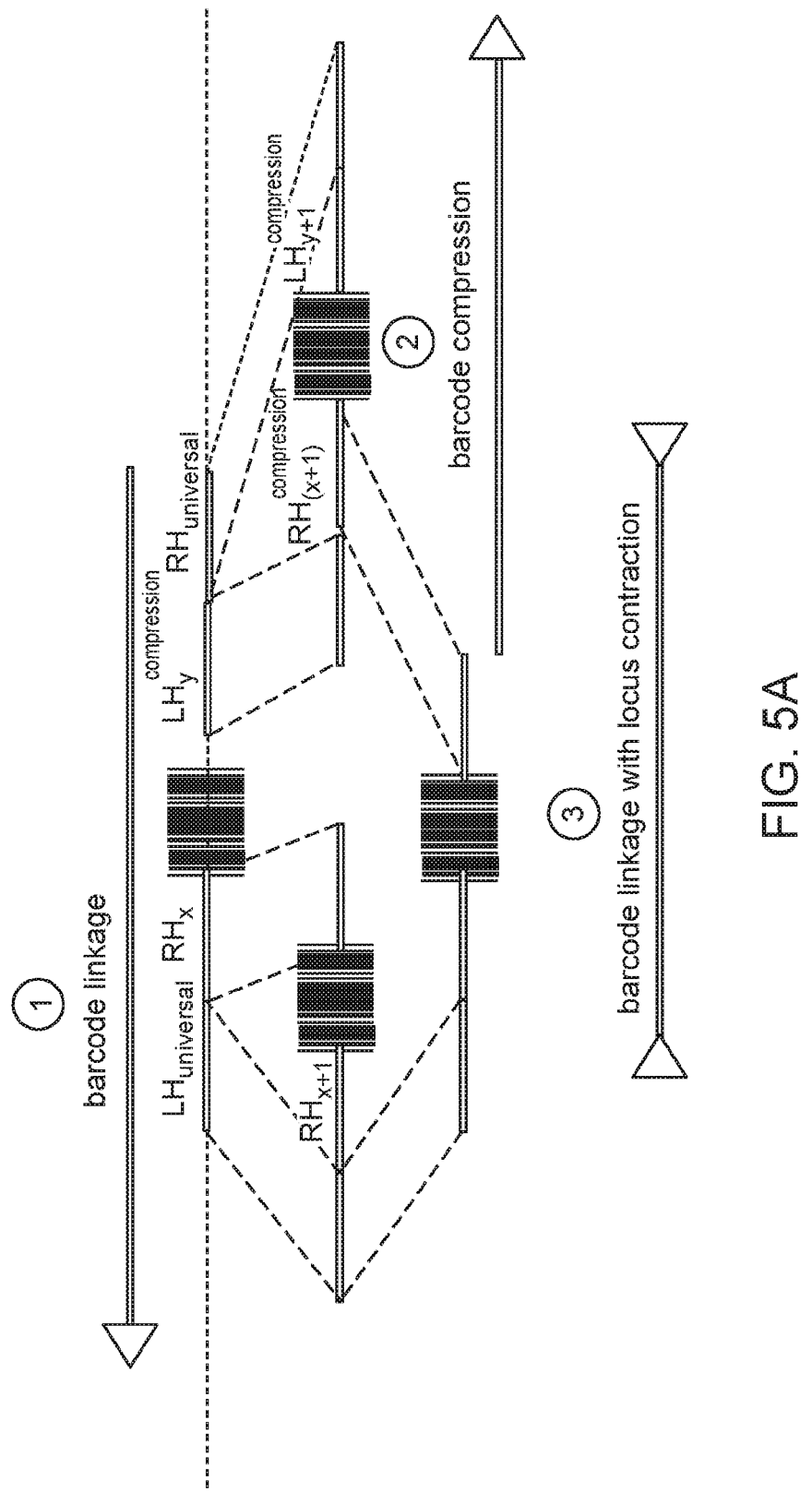
FIGS. 5A-5B show example operations of recursive barcode linkage and compression.
Figure 5B:
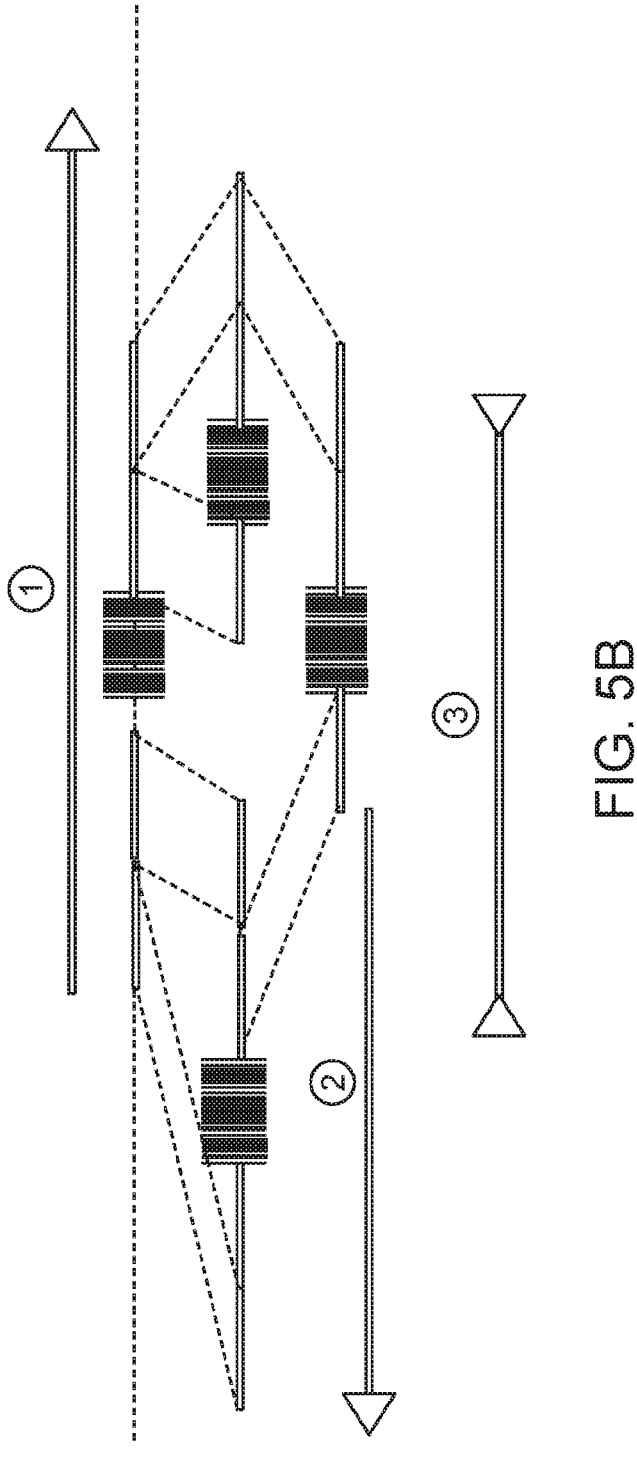

The entire process of (1) barcode linkage to the left, (2) compressed barcode insertion on the right, and (3) barcode array removal with the next barcode can be repeated an arbitrary number of times. An example method for this process is shown in FIGS. 5A-5B:

(1) Barcode linkage operations expand the locus to the left (FIG. 5A) or right (FIG. 5B), where each incoming barcode uses the same $LH_{universal}$, a round specific ($RH_x$) homology, and brings with it the homology on the left for a future round of barcode linkage ($RH_{x+1}$).

(2) Barcode compression expands the locus to the right (FIG. 5A) or left (FIG. 5B), and allows compressing the data stored in an arbitrary number of linked barcodes onto a single barcode. The original locus harbors an $RH_{universal}$ and an $LH_y$ compression homology that is reserved for a round of barcode compression that can occur after any number of rounds of barcode linkage.

(3) Barcode linkage with locus contraction enables recycling of LH and RH elements for future rounds of barcode linkage and compression. The compressed barcode is accompanied to the right by an $LH_{y+1}$ compression homology for yet another future round of compression, and to the left by an $RH_{x+1}$ (compression) homology that enables the next round of barcode linkage to remove previous linked barcodes and contract the locus. The entire set of operations are symmetrical as shown with (FIG. 5A) and (FIG. 5B). This method enables higher order combinatorial genetic modifications to be constructed and tracked with either a single barcode or short barcode array.

In addition to guide-donors, guide RNAs for CRISPR interference or activation, or small-hairpin RNA cassettes can be barcoded. These barcoded constructs can then be introduced as circular or linear vectors into a population of cells by transformation. The insertion of the barcode (and optionally its associated construct) into the barcode locus is mediated by specific homologous sequences on either side of the barcode enabling homologous recombination. The homologous recombination can occur passively or can be stimulated, for example, by a site-specific nuclease (protein-only nuclease or an RNA-guided nuclease), by linearization of the barcoded construct in vitro or in vivo, or by active donor recruitment. In an embodiment, the recombination of homologous sequence between barcodes can be performed in vitro (e.g. by Gibson assembly).

In an embodiment, the method can be used for tracking unknown genetic modifications during strain diversification or strain evolution to enable lineage tracking. In a related embodiment, barcodes may be inserted into the barcode locus after an unguided genetic diversification process, such as random genome-wide mutagenesis or error-prone PCR of a gene or pathway. In this setting, the genetic modification which the barcode represents is not initially known. Multiple rounds of genetic diversification, barcode linkage, and selection, enables the construction of lineage trees. Ultimately sequencing clones with desired properties can yield rich information about how the combination of changes ultimately leads to the phenotype of interest. Furthermore, individual clones can be rapidly isolated from a complex pool of thousands of unknown clones by our recombinase-directed indexing approach (U.S. Patent Application Pub. No. 2016/0122748, which is incorporated herein by reference in its entirety). In yet another embodiment, the barcodes can encode arbitrary digital information in 2-bit DNA encoding space. Subsequent barcode linkage can be used to store information temporally, and barcode compression enable data compression.

Figure 18:
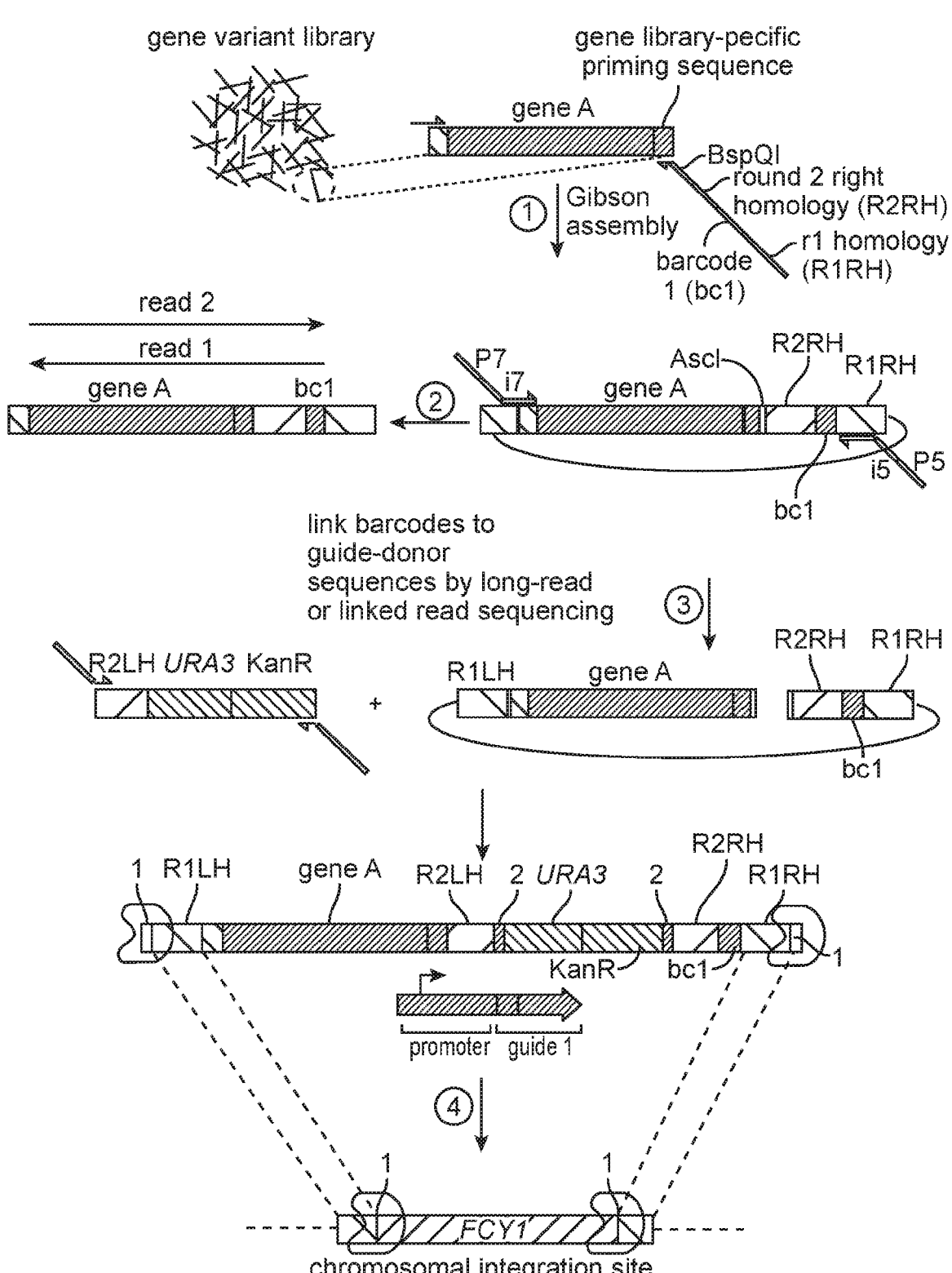
FIG. 18 shows an example method for constructing a library of polynucleotides, each containing a gene variant and associated barcode, for insertion into a chromosomal integration site.

In yet another embodiment, genetic constructs such as entire genes can be barcoded (either during synthesis, PCR amplification, or cloning into a recipient vector by a method such as GATEWAY cloning) and integrated. As shown in FIG. 18, a gene variant library can be constructed by various approaches, including multiplexed Gibson assembly (step 1). In this example, all gene variants contain common amplification sequences at the ends. Long read technologies can be used to associate unique bc1 sequences with gene sequences (step 2). As shown in step 3, a restriction site separating the gene construct from the round 2 right homology (R2RH) sequence enables the insertion of an R2LH sequence with bacterial and yeast-specific markers. Cleavage sites for round 2 flank the markers. Transformation and induction of guide 1 and Cas9 enables insertion of the gene variant construct at the barcode locus (step 4).

Figure 19:
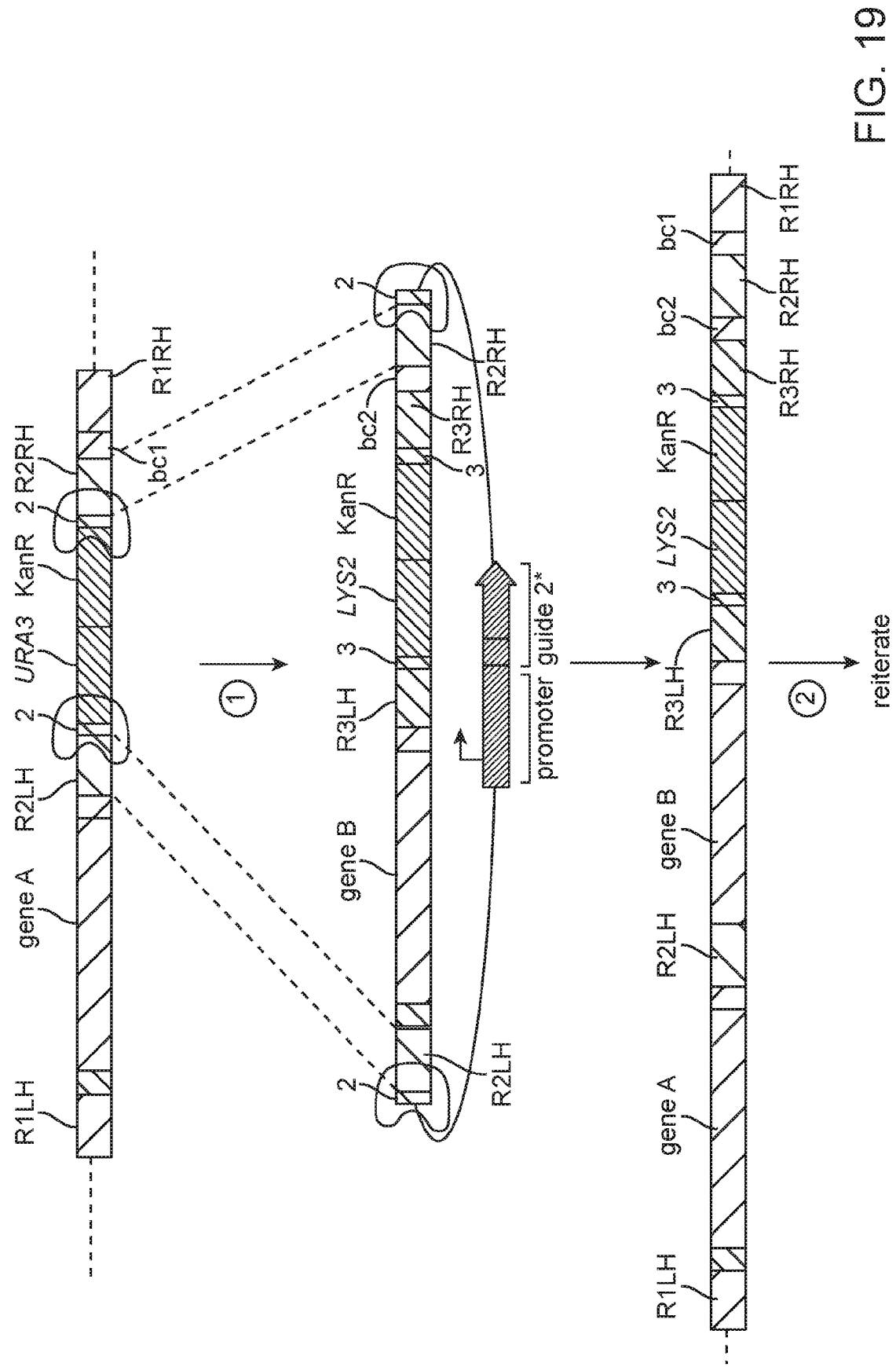
FIG. 19 shows an example method for simultaneous barcode linkage and concatenation of barcoded genes at the barcode locus.

Including recursive integration elements, in a similar style as the guide-donor setup described above, enables an array of barcoded gene constructs to be concatenated at the barcode locus. FIG. 19 shows a second gene variant (gene B) inserts via the guide 2 sites into the barcode locus in place of the marker portion of the gene A cassette from FIG. 18. The result is concatenation of gene A with gene B, and bc1 with bc2. Reiterating the process allows for an arbitrary number of genes to be inserted together, with barcode linkage followed by barcode compression and barcode locus contraction as in FIGS. 5A-5B.

Figure 20:
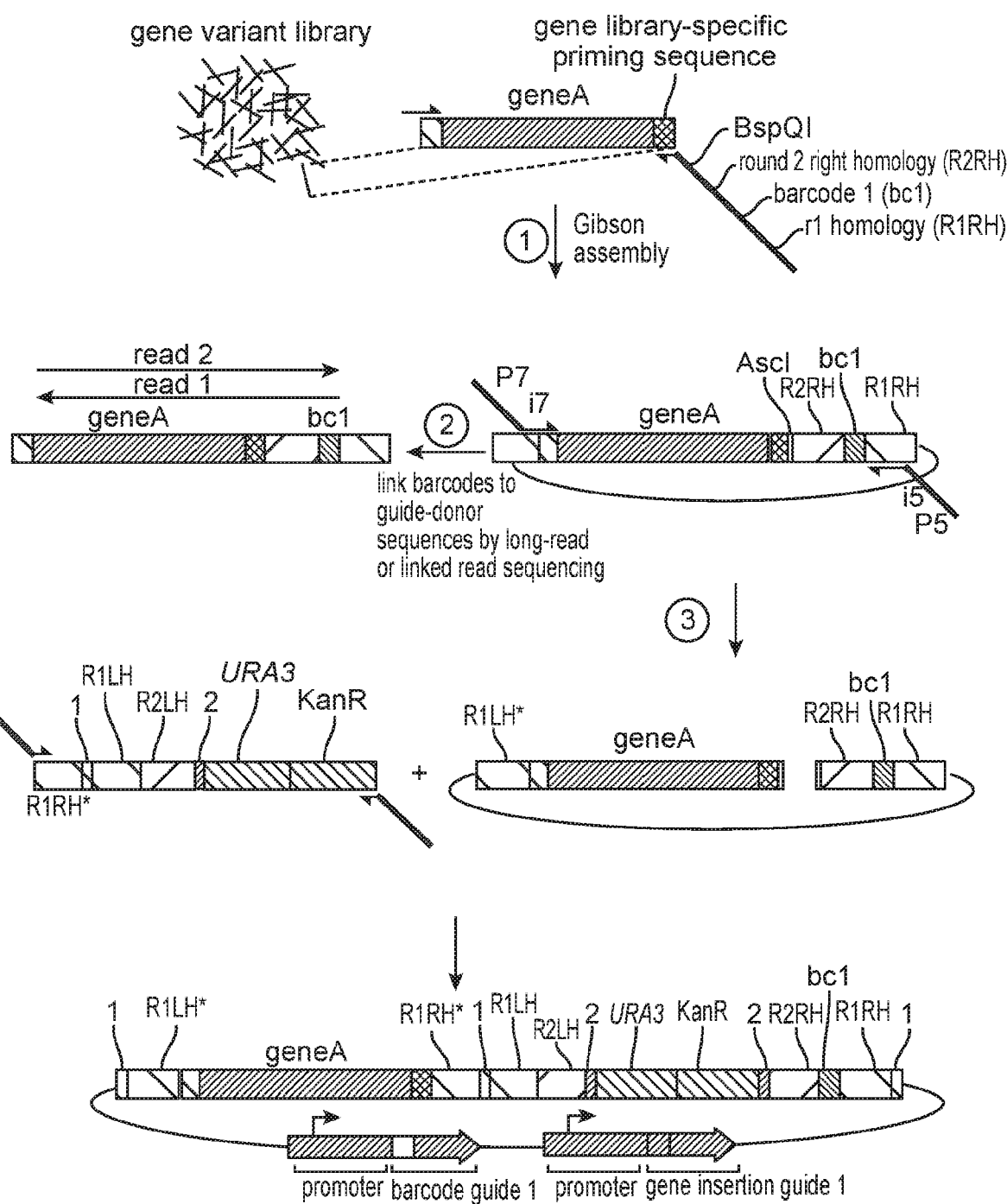
FIG. 20 shows an example method for barcoding entire gene libraries and pathways for gene insertion at arbitrary loci.
Figure 21:
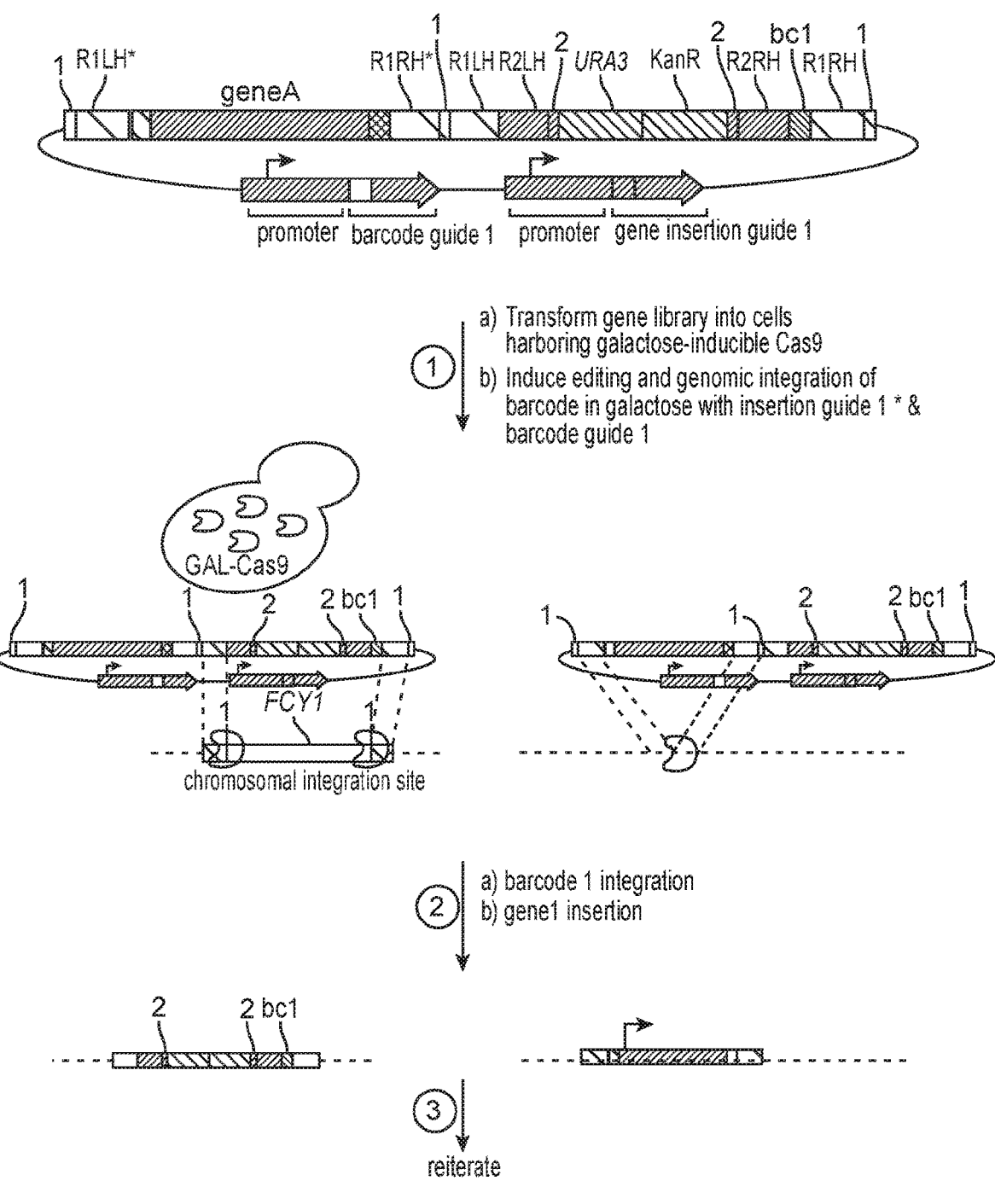
FIG. 21 shows simultaneous barcode insertion at the barcode locus and gene insertion at an arbitrary locus.

A variation of this method can introduce the genes at desired locations throughout the genome, where the gene on the plasmid is flanked by homologies to a desired genomic region, essentially becoming a donor DNA with a large genomic insertion (FIGS. 20 and 21). Notably, these barcoding methods can be combined in subsequent rounds of the method, such that round 1 could represent a library of genomic edits, round 2 a library of entire genes, etc. such that arbitrary barcode types (genome edits, entire genes, CRISPR interference/activation cassettes) can be mixed and matched.

One limitation of the methodology includes the need for sequential editing and barcoding steps. Another is that it might not be practical to confirm all the actual edits or modifications by whole genome sequencing of each clone in pools of very high complexity. Lastly, as a pool of variants are mixed with a pool of genetic constructs and the constructs are randomly introduced into each variant, the combinations that are interrogated by necessity must be an all-by-all, with modalities such as a many-by-many, few-by-many, many-by-few, or few-by-few approach. As a consequence, the size of each transformation needed to enable complete coverage of all desired variant combinations grows exponentially with each round of editing and barcoding, such that after 3 rounds of editing, 1000 initial variants results in 1000 choose 3, or 1000*999*998/(3*2*1)=166, 167,000, number of possible combinations, exploding with further rounds. Selection of desired variants from which to start (few-by-many) or downsizing the genetic constructs to add (many-by-few) enables management of the combination space. One way of managing this problem is to use Recombinase Directed Indexing (REDI) to create arrays of strains after editing. The methods described herein are compatible with Recombinase Directed Indexing to parse modified strains as detailed in U.S. Provisional Patent Application No. 62/559,493, which is incorporated herein by reference in its entirety. After strains are parsed into arrayed format, specific strains can be selected to receive libraries of second or later round barcoded cassettes. Practical considerations such as culture volumes employed in the laboratory and number of sequencing reads required for adequate coverage of large populations of variants will dictate the number of variant combinations that can ultimately be assayed.

In embodiments, at least two rounds of barcoding are performed on a plurality of cells. In embodiments, at least three rounds of barcoding are performed on a plurality of cells. In embodiments, at least four rounds of barcoding are performed on a plurality of cells. In embodiments, at least five rounds of barcoding are performed on a plurality of cells. In embodiments, at least six, at least seven, at least eight, at least nine, or at least ten rounds of barcoding are performed on a plurality of cells.

In embodiments, 2 to 100 rounds of barcoding are performed on a plurality of cells. In embodiments, 2 to 50 rounds of barcoding are performed on a plurality of cells. In embodiments, 2 to 20 rounds of barcoding are performed on a plurality of cells. In embodiments, 2 to 15 rounds of barcoding are performed on a plurality of cells. In embodiments, 2 to 10 rounds of barcoding are performed on a plurality of cells. In embodiments, 2 to 8 rounds of barcoding are performed on a plurality of cells. In embodiments, 2 to 6 rounds of barcoding are performed on a plurality of cells. In embodiments, 2 to 5 rounds of barcoding are performed on a plurality of cells. In embodiments, 2 to 4 rounds of barcoding are performed on a plurality of cells. In embodiments, 3 to 20 rounds of barcoding are performed on a plurality of cells. In embodiments, 4 to 20 rounds of barcoding are performed on a plurality of cells. In embodiments, 5 to 20 rounds of barcoding are performed on a plurality of cells. In embodiments, 6 to 20 rounds of barcoding are performed on a plurality of cells. In embodiments, 8 to 20 rounds of barcoding are performed on a plurality of cells. In embodiments, 10 to 20 rounds of barcoding are performed on a plurality of cells.

In embodiments, at least two rounds of barcoding are performed on a plurality of cells prior to barcode compression. In embodiments, at least three rounds of barcoding are performed on a plurality of cells prior to barcode compression. In embodiments, at least four rounds of barcoding are performed on a plurality of cells prior to barcode compression. In embodiments, at least five rounds of barcoding are performed on a plurality of cells prior to barcode compression. In embodiments, at least six, at least seven, at least eight, at least nine, or at least ten rounds of barcoding are performed on a plurality of cells prior to barcode compression.

In embodiments, 2 to 20 rounds of barcoding are performed on a plurality of cells prior to barcode compression. In embodiments, 2 to 15 rounds of barcoding are performed on a plurality of cells prior to barcode compression. In embodiments, 2 to 10 rounds of barcoding are performed on a plurality of cells prior to barcode compression. In embodiments, 2 to 8 rounds of barcoding are performed on a plurality of cells prior to barcode compression. In embodiments, 2 to 6 rounds of barcoding are performed on a plurality of cells prior to barcode compression. In embodiments, 2 to 5 rounds of barcoding are performed on a plurality of cells prior to barcode compression. In embodiments, 2 to 4 rounds of barcoding are performed on a plurality of cells prior to barcode compression. In embodiments, 3 to 20 rounds of barcoding are performed on a plurality of cells prior to barcode compression. In embodiments, 4 to 20 rounds of barcoding are performed on a plurality of cells prior to barcode compression. In embodiments, 5 to 20 rounds of barcoding are performed on a plurality of cells prior to barcode compression. In embodiments, 6 to 20 rounds of barcoding are performed on a plurality of cells prior to barcode compression. In embodiments, 8 to 20 rounds of barcoding are performed on a plurality of cells prior to barcode compression. In embodiments, 10 to 20 rounds of barcoding are performed on a plurality of cells prior to barcode compression.

In embodiments, at least two rounds of gene editing and barcoding are performed on a plurality of cells. In embodiments, at least three rounds of gene editing and barcoding are performed on a plurality of cells. In embodiments, at least four rounds of gene editing and barcoding are performed on a plurality of cells. In embodiments, at least five rounds of gene editing and barcoding are performed on a plurality of cells. In embodiments, at least six, at least seven, at least eight, at least nine, or at least ten rounds of gene editing and barcoding are performed on a plurality of cells.

In embodiments, 2 to 20 rounds of gene editing and barcoding are performed on a plurality of cells. In embodiments, 2 to 15 rounds of gene editing and barcoding are performed on a plurality of cells. In embodiments, 2 to 10 rounds of gene editing and barcoding are performed on a plurality of cells. In embodiments, 2 to 8 rounds of gene editing and barcoding are performed on a plurality of cells. In embodiments, 2 to 6 rounds of gene editing and barcoding are performed on a plurality of cells. In embodiments, 2 to 5 rounds of gene editing and barcoding are performed on a plurality of cells. In embodiments, 2 to 4 rounds of gene editing and barcoding are performed on a plurality of cells. In embodiments, 3 to 20 rounds of gene editing and barcoding are performed on a plurality of cells. In embodiments, 4 to 20 rounds of gene editing and barcoding are performed on a plurality of cells. In embodiments, 5 to 20 rounds of gene editing and barcoding are performed on a plurality of cells. In embodiments, 6 to 20 rounds of gene editing and barcoding are performed on a plurality of cells. In embodiments, 8 to 20 rounds of gene editing and barcoding are performed on a plurality of cells. In embodiments, 10 to 20 rounds of gene editing and barcoding are performed on a plurality of cells.

In embodiments, at least two rounds of gene editing and barcoding are performed on a plurality of cells prior to barcode compression. In embodiments, at least three rounds of gene editing and barcoding are performed on a plurality of cells prior to barcode compression. In embodiments, at least four rounds of gene editing and barcoding are performed on a plurality of cells prior to barcode compression. In embodiments, at least five rounds of gene editing and barcoding are performed on a plurality of cells prior to barcode compression. In embodiments, at least six, at least seven, at least eight, at least nine, or at least ten rounds of gene editing and barcoding are performed on a plurality of cells prior to barcode compression.

In embodiments, 2 to 20 rounds of gene editing and barcoding are performed on a plurality of cells prior to barcode compression. In embodiments, 2 to 15 rounds of gene editing and barcoding are performed on a plurality of cells prior to barcode compression. In embodiments, 2 to 10 rounds of gene editing and barcoding are performed on a plurality of cells prior to barcode compression. In embodiments, 2 to 8 rounds of gene editing and barcoding are performed on a plurality of cells prior to barcode compression. In embodiments, 2 to 6 rounds of gene editing and barcoding are performed on a plurality of cells prior to barcode compression. In embodiments, 2 to 5 rounds of gene editing and barcoding are performed on a plurality of cells prior to barcode compression. In embodiments, 2 to 4 rounds of gene editing and barcoding are performed on a plurality of cells prior to barcode compression. In embodiments, 3 to 20 rounds of gene editing and barcoding are performed on a plurality of cells prior to barcode compression. In embodiments, 4 to 20 rounds of gene editing and barcoding are performed on a plurality of cells prior to barcode compression. In embodiments, 5 to 20 rounds of gene editing and barcoding are performed on a plurality of cells prior to barcode compression. In embodiments, 6 to 20 rounds of gene editing and barcoding are performed on a plurality of cells prior to barcode compression. In embodiments, 8 to 20 rounds of gene editing and barcoding are performed on a plurality of cells prior to barcode compression. In embodiments, 10 to 20 rounds of gene editing and barcoding are performed on a plurality of cells prior to barcode compression.

In embodiments, only one plasmid library is created by cloning in bacteria. In embodiments, the initial round 1 library may be cleaved in vitro with a meganuclease (e.g., SceI meganuclease) to linearize the guide-donor backbone. In embodiments, the resulting single library of guide-donors can be transformed, together with any future round of insert as desired, directly into yeast. Not only does this eliminate the need for multiple laborious step 2 cloning procedures for each new round of barcoding/editing, but this also greatly enhances editing efficiency because linear fragments activate HDR machinery. This approach demonstrates a setup featuring three independent, orthogonal methods for enhancing HDR: donor recruitment, donor amplification, and linearized donor vector.

EXAMPLES

One skilled in the art would understand that descriptions of making and using the particles described herein is for the sole purpose of illustration, and that the present disclosure is not limited by this illustration.

Example 1. First Round Barcode Integration

Figure 6:
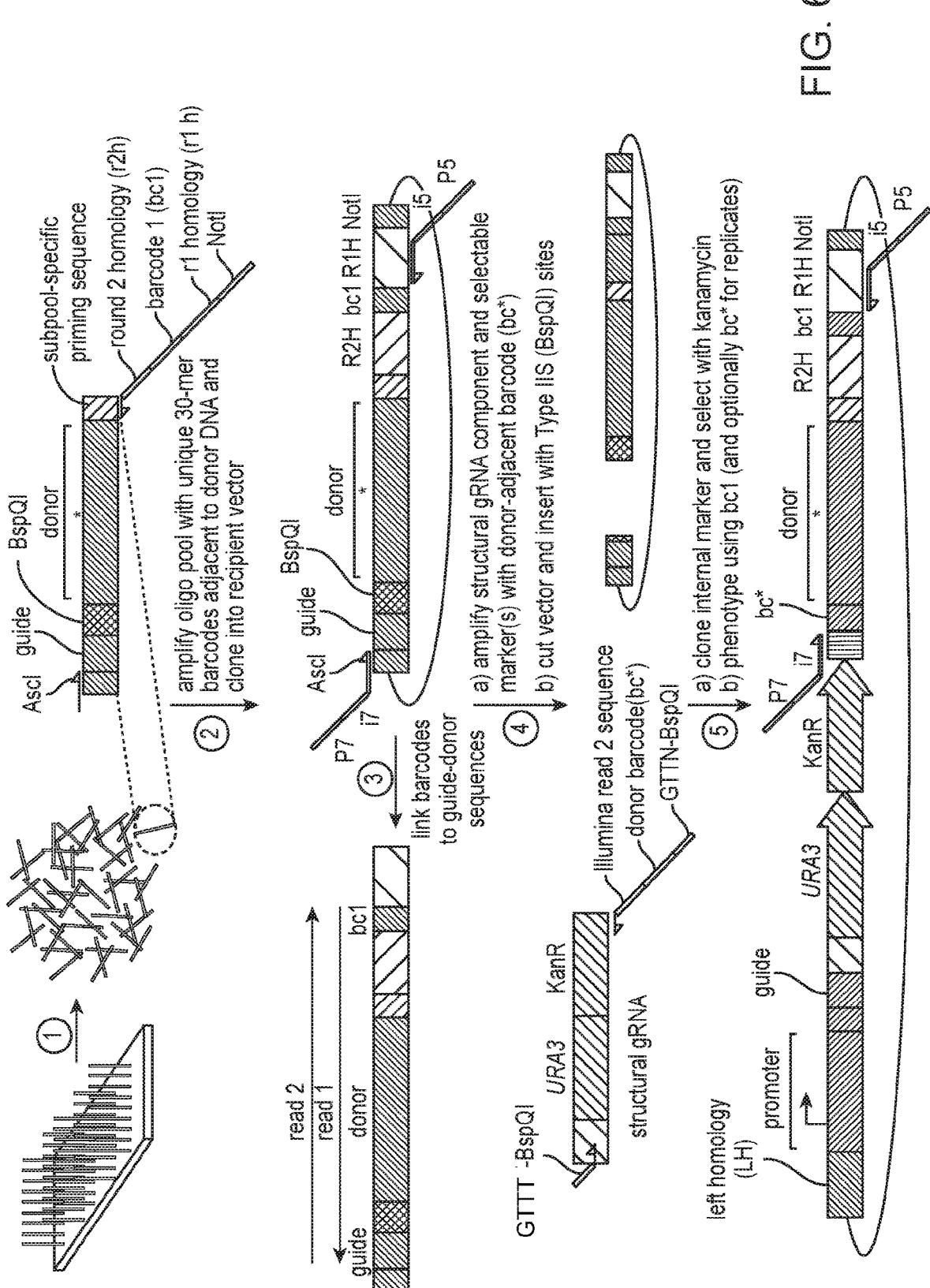
FIG. 6 shows an example method of library cloning to link guide-donors with unique DNA barcodes.

Oligonucleotides encoding guide-donors are synthesized in high-density array format and cleaved off of the array surface to generate a complex pool. Oligonucleotide pools containing the guide RNA-donor DNA sequences (guide-donor) are barcoded during polymerase chain reaction (PCR) and cloned into a vector (FIG. 6, steps 1, 2). Each oligo contains common amplification sequences flanking the guide-donor cassette to enable amplification of specific subpools. The forward primer harbors a restriction site (AscI) at its 3'-end and the reverse primer encodes a distinct restriction site (NotI) at its 5'-end followed by a degenerate barcode (bc1) encoding a pseudo-random sequence (either NNNVHTGNNNVHTGNNNVHTGNNNVHTGNNN or NNNTGVHNNNTGVHNNNTGVHNNNTGVHNNN) that excludes illegal restriction sites (NotI, AscI, and BspQI). The degenerate barcode is flanked by 50 bp homology sequences termed round 1 homology (r1h) and round 2 homology (r2h). NotI and AscI sites enable sticky end cloning into a multi-copy recipient vector, with the AscI site at the 3'-end of the guide RNA promoter. The guide and donor sequences are separated by a type IIS restriction site (BspQI) that enables cloning with an arbitrary overhang, in this case the GTTT directly 3' of the guide sequence, to enable cloning in the constant structural component of the guide RNA.

Sequencing across the guide, donor, and barcode assigns to each barcode the exact guide-donor sequence (FIG. 6, step 3). High-throughput sequencing (HTS) of the first-step cloning products enables linking the guide-BspQI-donor sequences with unique barcodes (bc1). Paired-end sequencing can be used to increase confidence of base calls following quality-based merging of read 1 and read 2.

An insert containing the guide scaffold and selectable markers is then cloned in between the guide and donor (FIG. 6, steps 4, 5). Step 4a: The structural guide RNA component along with yeast-specific (e.g. URA3, LYS2, or HIS3) and bacterial-specific (e.g. kanR) selection markers are amplified with primers harboring BspQI sequences at their 5'-ends. The reverse primer includes an additional barcode (bc*; either NNNNNN or NNNNNNHVVNHBBHBHD)

situated 3' of the Illumina read 2 priming sequence, modified to contain a G-to-A SNP at the first position of the BspQI site. Step 4b: Cleavage of the first step cloning products with BspQI followed by phosphatase treatment enables scarless cloning of the structural gRNA insert. These second-step libraries are selected with kanamycin to enable enrichment of vectors harboring the insert. Paired-end HTS of bc*-donor and bc1 enables mapping the barcodes to unique guide-donor combinations (FIG. 6, step 5).

Figure 7:
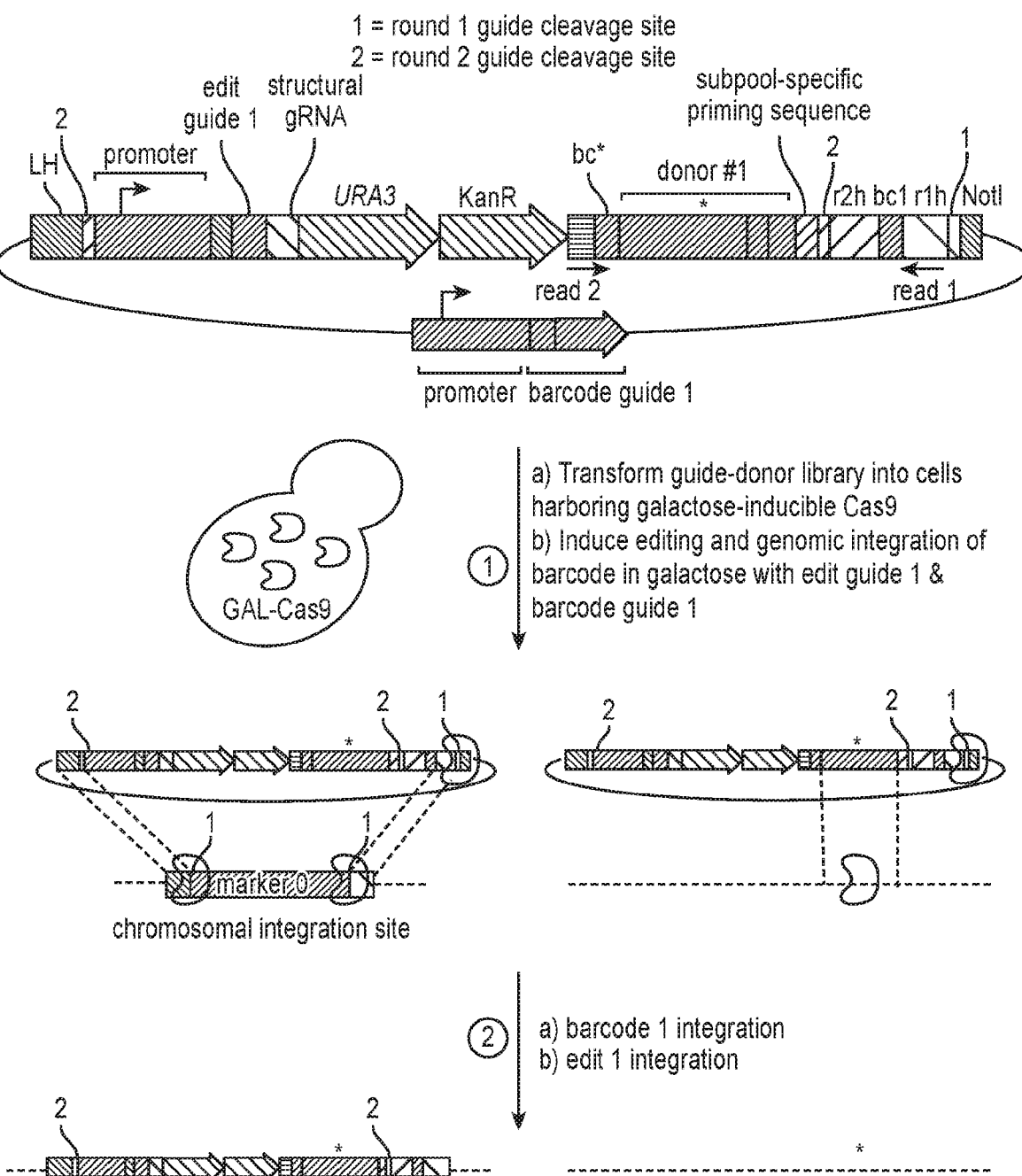
FIG. 7 shows an example method of simultaneous editing and barcode integration via self-destructing plasmids.

The guide-donor vectors after the second cloning step are transformed into yeast and selected with the insert-specific marker (URA3) (FIG. 7). The guide RNAs, which may be different for each donor DNA/genetic construct, target specific genomic loci for double-strand breaks, which are repaired by the corresponding donor DNAs resulting in precise genome modifications at desired locations throughout the genome. The recipient strain is modified to harbor a barcode integration locus with a counter-selectable marker (FCY1). In addition to the guide sequences from the library, the guide-donor plasmids also harbor a barcode guide 1 expression unit to promote barcode integration, with barcode guide 1 cleavage sites flanking FCY1. Following transformation, the guide-donor plasmids accumulate to high copy number through outgrowth. To the right of the round 1 homology (r1h) sequence on the guide-donor plasmid resides a barcode guide 1 cleavage site, which enables later linearization of the plasmid to accelerate plasmid loss after editing.

A second, universal guide RNA or site-specific nuclease targets the barcode locus and/or the guide-donor plasmid (resulting in linearization of the plasmid) and homologous recombination at the barcode locus. This aspect, which is defined by a guide-donor construct that inserts a barcode into the genome at the barcode locus with or without active donor recruitment (such as mediated by LexA-Fkh1 or LexA-FHA), and makes a defined genomic change elsewhere, is described in detail in U.S. Provisional Application No. 62/559,493, which is incorporated herein by reference in its entirety. In addition, or alternatively, the barcode incorporation into the barcode locus can be stimulated by active donor recruitment (see U.S. Provisional App. No. 62/559,493).

Induction of Cas9 results in barcode guide 1 cleaving the plasmid and genomic barcode locus, and in edit guide 1 cleavage elsewhere in the genome. (Step 2a) Barcode guide 1 cleavage results in genomic integration of the entire guide RNA-bc*-donor DNA-bc1 cassette via a 5' universal left homology (LH) sequence present on both the guide-donor plasmid and in the chromosomal barcode site, and a round-specific 3'-homology. (Step 2b) Edit guide 1 cleavage is followed by donor DNA-directed homologous recombination to generate edit #1.

Example 2. Recursive Barcode Integration

Figure 8:
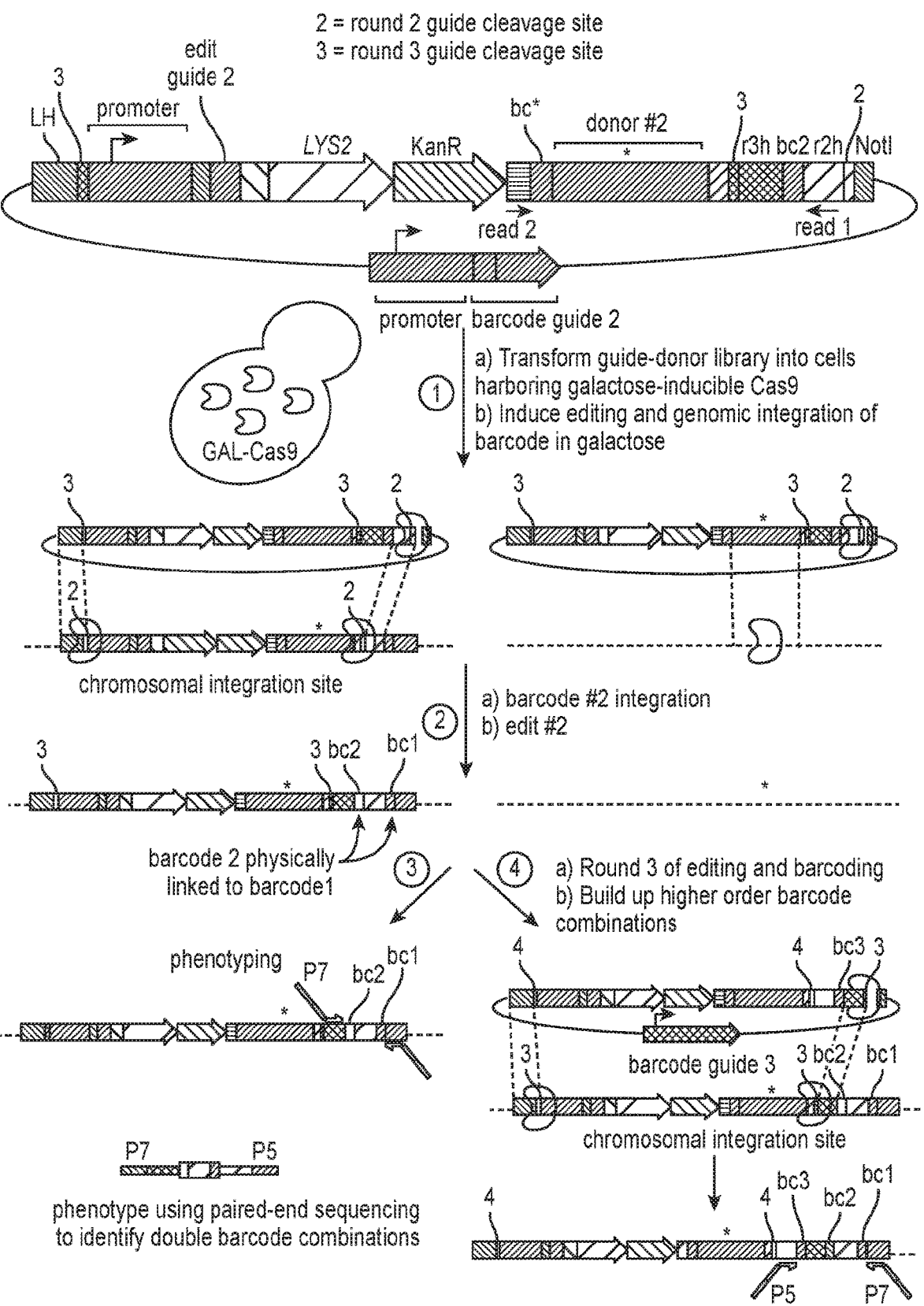
FIG. 8 shows an example method of higher-order guide-donor editing and sequential linkage of barcodes.

Each guide-donor barcoded integrates with homology and cut sites for the next round. As shown in FIG. 8:

(1) A pool of strains harboring bc1 variants are transformed with guide-donor plasmids tagged with bc2 to enable a second round of multiplexed editing, generating a pool of strains with all possible combinations of bc1 and bc2. The cloning strategy for the round 2 guide-donor plasmids is as follows: (a) The same universal left homology (LH) flanks a barcode guide 3 site to enable a subsequent round of editing (round 3); (b) a different yeast marker (LYS2) is used in the structural guide RNA insert; (c) the round 2 homology (r2h) is the same as that used for guide-donor plasmids in round 1 (see FIG. 6) except the guide site is placed on the 3'-end; (d) upstream (US) of bc2 resides a stretch of homology (r3h) for round 3 integration, with the barcode 3 guide site situated at the 5'-end of r3h.

(2) Integration via LH and r2H results in bc1 being linked close together with bc2. The previous guide-donor cassette represented by bc1 is removed in this step. The removal of the integrated yeast marker (URA3) from round 1 enables recycling of this marker in round 3.

(3) The bc1 and bc2 sequences are now linked close together, enabling paired-end HTS to identify double-barcode combinations for strain identification and pooled phenotyping.

(4) (a) Round 3 of editing and barcoding utilizes a guide donor plasmid with the same LH with the cleavage site for barcode guide 4, a bc3 sequence flanked by r4h and r3h sequences, each with their respective guide targets flanking them, and a barcode guide 3 expression unit. The yeast internal marker can be swapped back to that of round 1. The use of counter-selectable markers and self-destruction of the guide-donor plasmid removes markers from previous rounds of editing. After round 1, URA3 selection followed by FCY1 counter-selection with 5-FC ensures integration of the URA3 cassette. After round 2, LYS2 selection followed by URA3 counter-selection with 5-FOA ensures integration of the LYS2 cassette. After round 3, URA3 selection followed by LYS2 counter-selection with α-aminoadipate ensures integration of the URA3 cassette, and so on. (b) Subsequent rounds of editing (round n) are enabled by constructing a guide-donor recipient vector harboring the (n+1) barcode guide site at the 3'-end of the LH and at the 5'-end of r(n+1)h barcode integration sequences, an (n) barcode guide site at the 3'-end of r(n)h, and a Pol III expression unit for the (n) edit guide elsewhere on the plasmid. Each right homology sequence r(n)h and r(n+1)h should not harbor significant homology to any previously used right homology sequence. These can be designed by generating random 50-mers with a defined range of G/C/A/T content and confirming lack of significant homology to the yeast genome and other right homology sequences through BLAST. The (n) and (n+1) barcode guide sites should not harbor any significant homology to any other site in the genome with protospacer adjacent motifs (PAMs), and this can be checked via BLAST or off-target algorithms tailored for RNA-guided nucleases.

Example 3. Barcode Compression

Figure 9:
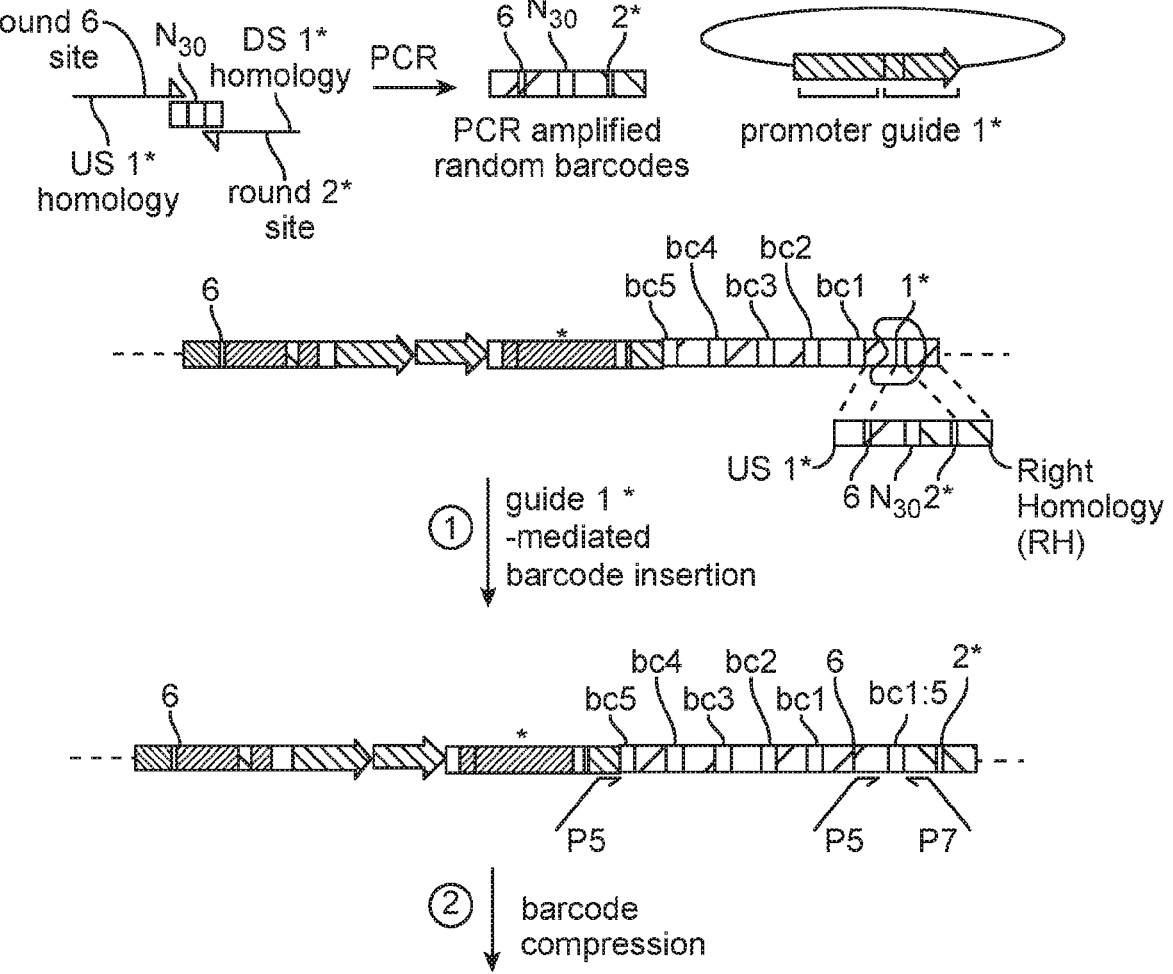
FIG. 9 shows an example method of guide-donor barcode compression.
Figure 10:
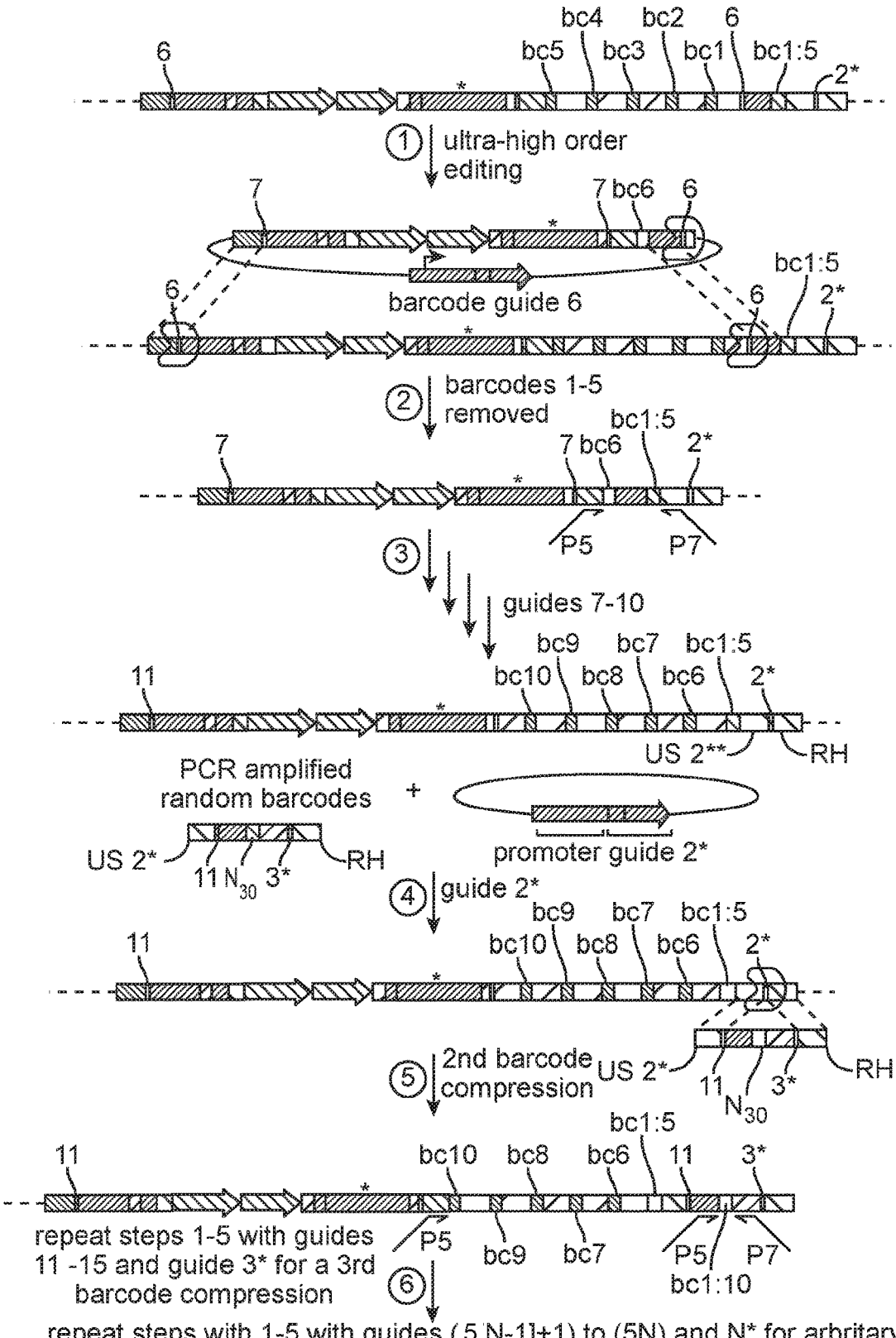
FIG. 10 shows an example method of ultra-higher order editing via barcode compression.

Barcode compression can be accomplished with a guide construct targeting the compressor landing pad, and a PCR product containing the compressor barcode (FIGS. 9 and 10). As subsequent rounds of editing build up longer barcodes, the feasibility and practicality of HTS to identify barcode combinations becomes limiting because the required read lengths are on the order of [(barcode length) *(number of barcodes)+(homology length)*(number of barcodes−1)] divided by 2 in the case of paired-end sequencing. FIG. 9 shows the following steps: (1) After an arbitrary number of editing rounds (e.g. 5), a plasmid harboring a guide termed 1*, where the  denotes that this guide will enable barcode compression, is transformed into the pool of edited strains along with a PCR amplicon harboring highly complex barcodes (e.g. $N_{30}$). As shown in FIGS. 2A-2C**, this amplicon can also be linked to a marker for selection. The barcodes are flanked by sequences that enable HDR at the guide 1* site, termed upstream compression round 1* homology (US 1**) and right homology (RH). To enable further rounds of editing and barcoding, a round 6 site is placed adjacent to the US 1* homology, along with an r6h sequence. To enable a future round of barcode compression, a round 2* site is engineered adjacent to the RH homology, along with US round 2* homology sequence. The barcodes can be synthesized as a stretch of degenerate sequence (e.g. $N_{30}$) flanked by constant sequence for amplification (top left).

(2) HTS of the entire barcode locus allows for linkage of the individual bc1, bc2, bc3, bc4, and bc5 sequences to the unique bc1:5 compressed barcode. Thereafter, these strains can be phenotyped through sequencing bc1:5 alone.

The compression of barcodes be1 through bc5 to bc1:5 can be followed by iterative rounds of editing and barcode compression (as in FIGS. 7 and 8). FIG. 10 shows the steps for higher-order editing via barcode compression:

(1) The next barcode (bc6) inserts adjacent to the compressed barcode (bc1:5), accompanied by edit #6 elsewhere in the genome (not shown).

(2) The guide-donor-bc6 cassette removes all of the barcodes bc1, bc2, bc3, bc4, and bc5, along with their adjacent homologies, leaving only bc1:5. This prevents the barcode locus from expanding in size, and allows recycling of previously used guides 1* through 5*, as well as their associated homologies r1h through r5h for subsequent rounds of editing and barcoding.

(3) Recursive barcoding resumes as in FIG. 4B.

(4) Barcodes bc6 through bc10, in combination with bc1:5, can be further compressed with the 2* guide targeting the site 2* to the right of bc1:5. The PCR amplicon is analogous to that which generated bc1:5 barcodes, with the exception that site 5 is replaced by site 11, and the site 2* is replaced by the 3** site. Flanking homologies US 2* (equivalent to DS 1* from the first round of barcode compression) and universal right homology (RH) sequences placed during round 1** of barcode compression enable targeting.

(5) HTS of the entire barcode locus allows for linkage of the individual bc1:5, bc6, bc7, bc8, bc9, and bc10 sequences to the single barcode bc1:10. Thereafter, these strains can be interrogated through sequencing bc1:10.

(6) Even further rounds of editing and barcoding can be initiated with guide 11*, and further compressed using the 3** site to generate with an arbitrary number of barcoded edits.

It may be advantageous to have the barcode, but not the guide-donor sequence integrate (as originally shown in FIGS. 7 and 8), because there can be competition between the genome-integrated guide and the incoming guide for the next round, which might lead to lower editing efficiencies. Furthermore, not integrating the donor allows for simpler WGS verification of the edit, as one does not have to be concerned about reads from the donor confounding the variant call at the target site.

Figures 11A, 11B:
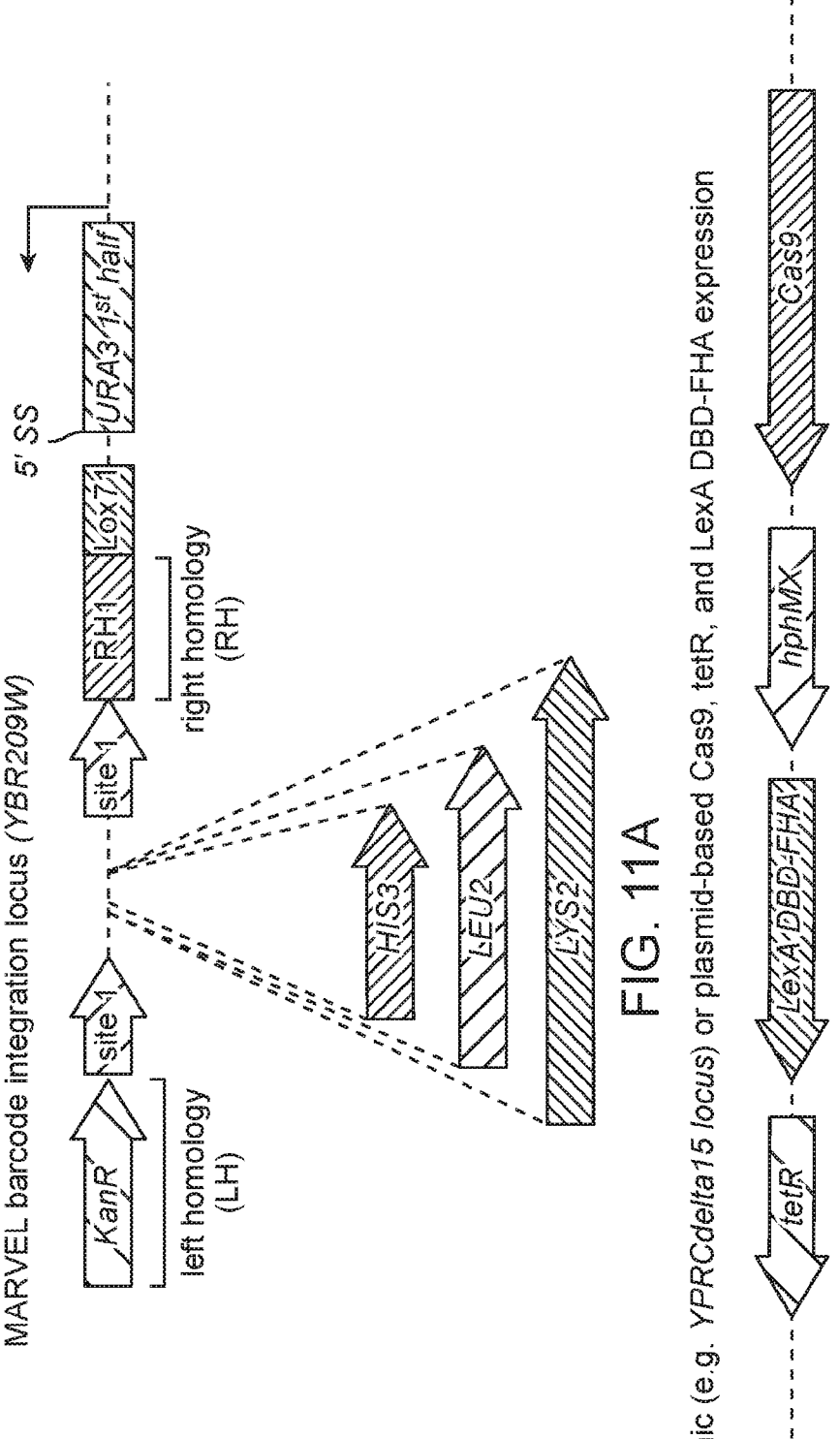
FIGS. 11A-11B show an example barcode locus with different selectable markers for the starting (round 0) cell.

In order to integrate the barcode without integrating the guide or donor, the landing pad can be designed to integrate only the insert residing in between the guide-donor (FIGS. 11A-11B). FIGS. 11A-11B show the initial landing pad prior to receiving the round 1 barcode. The left homology can be arbitrarily long, and in this case the ~1 kb kanR bacteria/ yeast shuttle marker is used as homology. As the method can proceed in different selectable marker orders, various starting strains can be constructed with the marker flanked by the site 1 guide cleavage target. The right homology is shorter than the left homology and is adjacent to a Lox71 site, which can be used for recombinase-directed indexing and for other Cre-Lox-mediated barcode linkage approaches. The starting strain can have trans-acting factors Cas9, TetR, and LexA-FHA either expressed from the genome or from plasmids.

Figure 12:
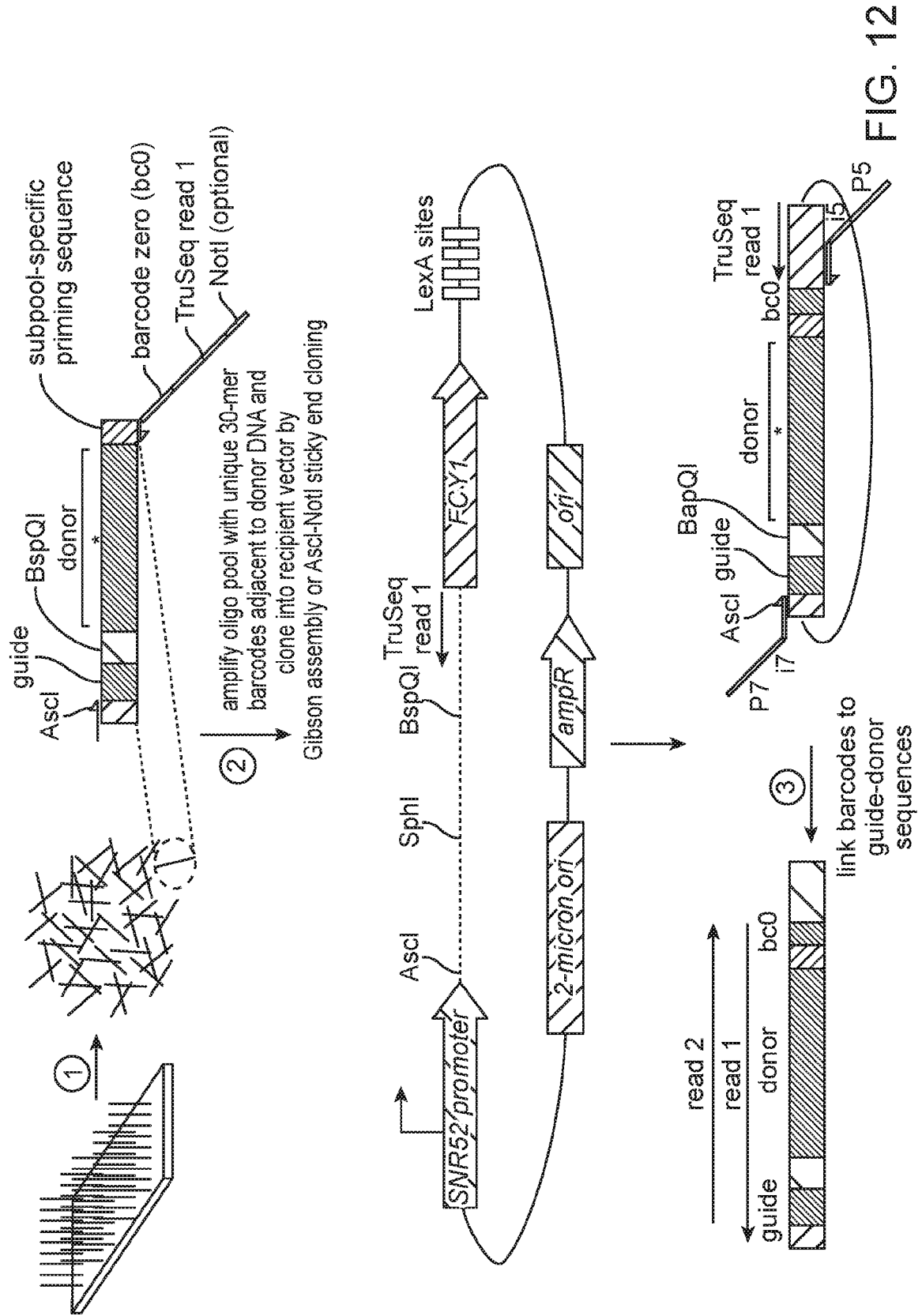
FIG. 12 shows an example cloning barcoded guide-donor library for barcode integration without guide-donor integration.
Figure 13:
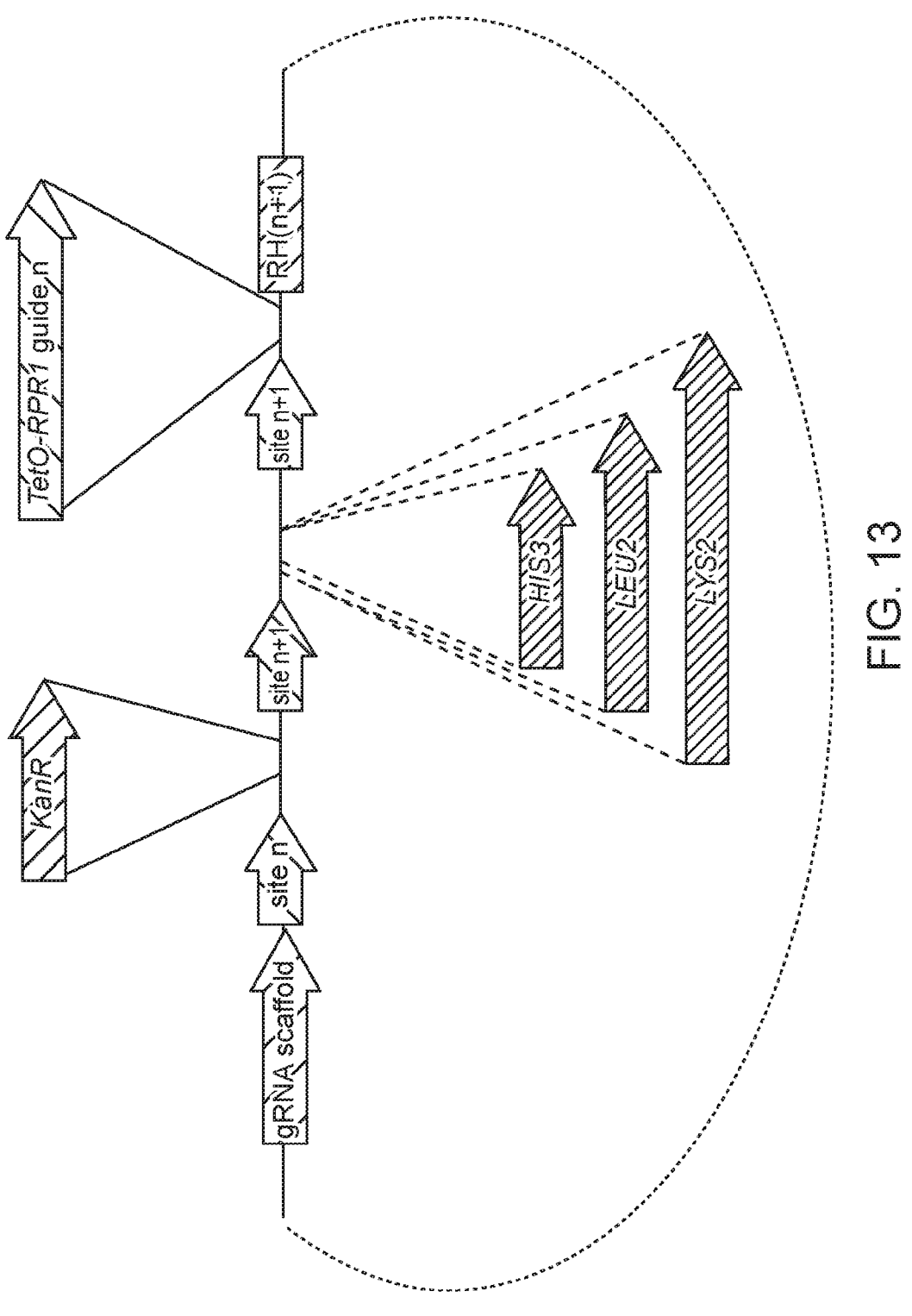
FIG. 13 shows an example of construction of a series of round-specific inserts for barcode integration without guide-donor integration.
Figures 14, 15A:
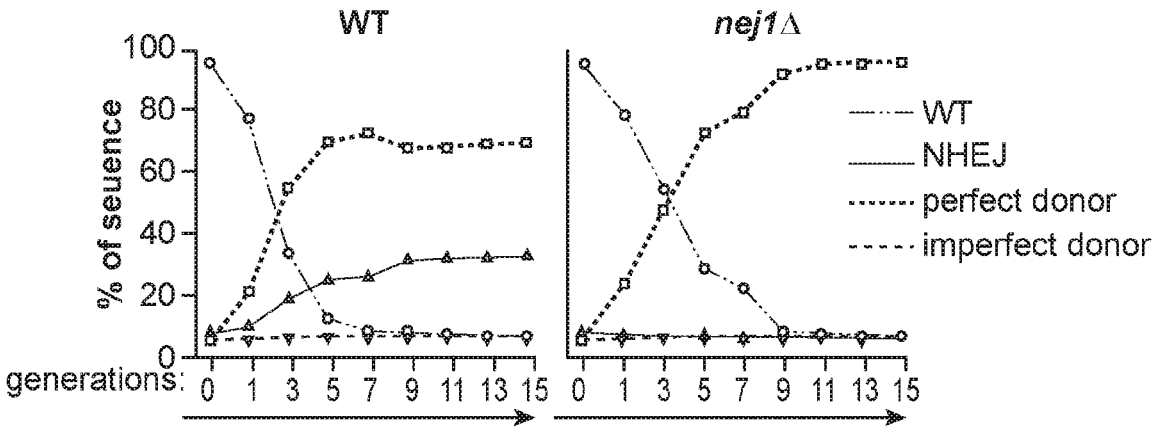
FIG. 14 shows an example method for associating the guide-donor barcodes with insert barcodes for barcode integration without guide-donor integration.
FIGS. 15A-15C show simultaneous genome editing, guide-donor barcode integration, and plasmid self-destruction for a single barcode.

Example 4. Cloning Barcoded Guide-Donor Libraries for Barcode Integration without Guide-Donor Integration An additional advantage of this setup is that a single step 1 guide-donor plasmid library can be used to receive inserts for multiple rounds (FIGS. 12-14). To achieve this, an additional barcode is added during the insert cloning step, which is associated with the guide-donor barcode (bc0) by a sequencing step (FIG. 14; note only part of the insert containing the barcode is shown in the bottom plasmid diagram).

In this version of the method, the guide-donor does not integrate—only the insert does. The initial barcode added to the guide-donor in step 1 of cloning also does not integrate, but it is important because it is mapped onto the insert barcode in step 2 cloning. Note that the integration guide in the insert does integrate. However, it is subject to TetR repression so it will not compete with the incoming guide in the absence of anhydrotetracycline (ATc). Alternatively, the integration guide can be paired with a different CRISPR nuclease, such as Cas12a.

FIG. 13 shows steps that can be used to build the insert for each round. Once constructed, these are used as a template for PCR to generate barcoded, round-specific inserts. Here is an example strategy for building these inserts:

step 1) clone gBlocks containing guide sites into backbone.

step 2) clone inducible barcode integration guide for round n.

step 3) clone kanR yeast/bacterial shuttle marker. This cleans up background for internal cloning and also serves as universal left arm homology.

step 4) clone in up to 3 different markers for each round. For example, for 3 rounds of editing can proceed in 6 different orders with 3 markers:

a) HIS3-LEU2-LYS2 b) HIS3-LYS2-LEU2 c) LEU2-LYS2-HIS3 d) LEU2-HIS3-LYS2 e) LYS2-HIS3-LEU2 e) LYS2-LEU2-HIS3

Performing the method with different marker order will check whether genetic interactions occur between engineered variants and the particular auxotrophic state of the cell at each round.

In FIG. 14, the round-specific insert templates from FIG. 13 are amplified with a reverse primer that contains the barcode, a short right homology (RH) and a cloning site. These are cloned by sticky-end ligation after TypeIIS restriction digestion into the step 1 guide-donor libraries from FIG. 12. An amplicon encompassing the insert barcode, the donor, and the guide-donor barcode allows "mapping" the guide-donor barcode onto the insert barcode.

Example 5. Simultaneous Genome Editing, Guide-Donor Barcode Integration, and Plasmid Self-Destruction for Single Barcode Integration Barcode integration and editing can be induced to 100% using inducible Cas9. WT and nej1Δ were transformed with GAL-Cas9 and a guide-donor cassette to introduce a premature termination codon (PTC) in the ADE2 gene. Cas9 expression was induced by galactose and aliquots were harvested at the indicated generations. The ADE2 locus was analyzed by NGS and the fractions of WT sequence, NHEJ indels, and donor DNA-directed editing (either perfect or imperfect repair) were calculated (see Methods). FIG. 15A shows the mean percentages at each generation from duplicate experiments.

Figure 15B:
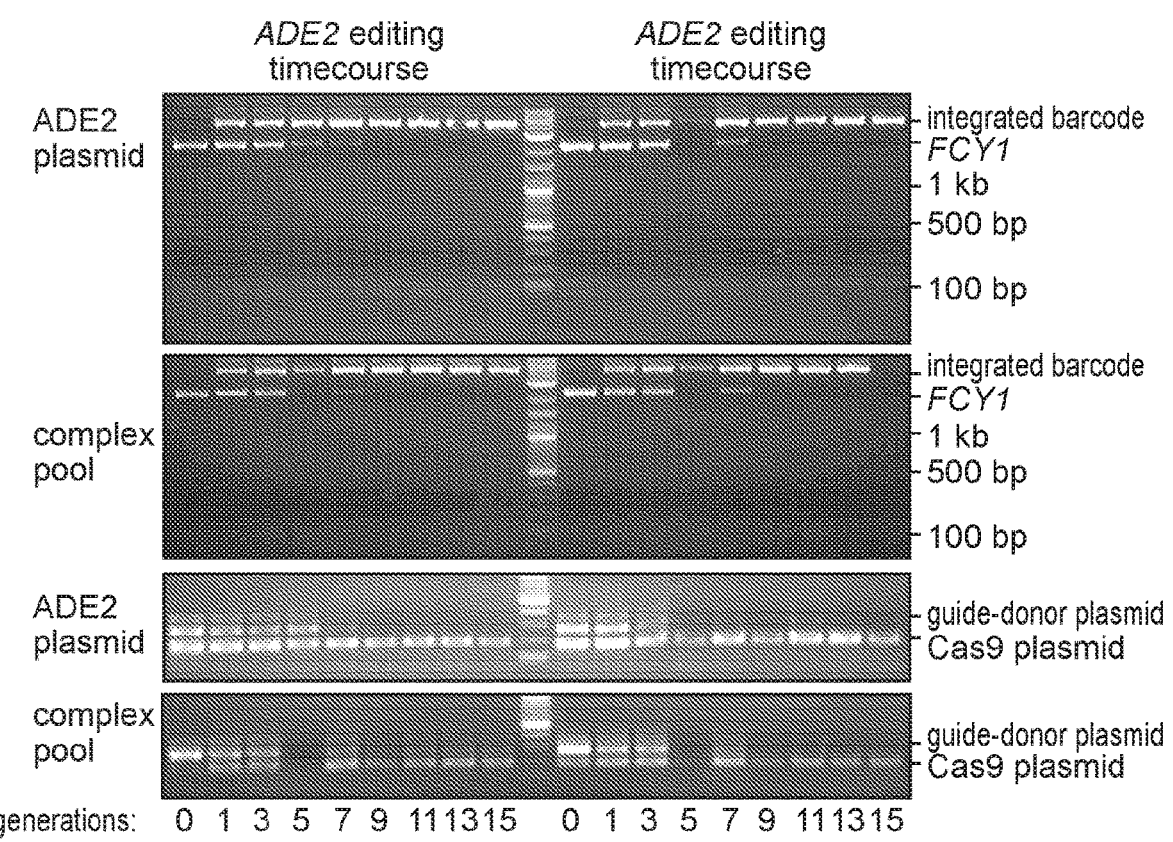

Integration of the guide-donor barcode was assayed by amplification targeting the chromosomal barcode locus for the single ADE2 guide-donor plasmid (FIG. 15B, top) as well as a complex pool of >100,000 barcoded guide-donor plasmids (bottom). The uncropped gel image indicates an absence of detectable NHEJ indel events at the barcode locus. Self-destruction of the guide-donor plasmids was assessed by a three-primer PCR, with a common forward primer and either a guide-donor plasmid-specific primer (top band) or a Cas9-plasmid specific primer (bottom band).

Figure 15C:
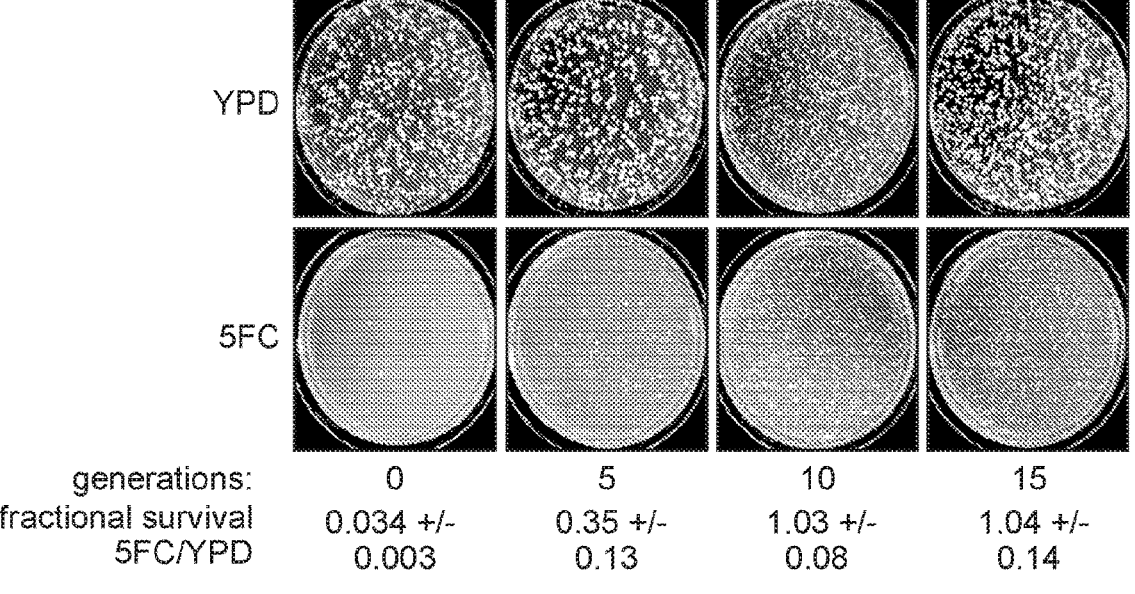

Cultures at the indicated generations of galactose induction were plated in quadruplicate at a density of ~1000 cells per plate on rich medium (YPD) and FCY1 counter-selectable medium (5-FC) (FIG. 15C). The fraction of surviving colonies on plates are shown. All experiments were repeated with three biological replicates starting from independent transformations of the guide-donor plasmids.

Example 6. Barcode Linkage Proof of Principle

Figures 16A, 16B:
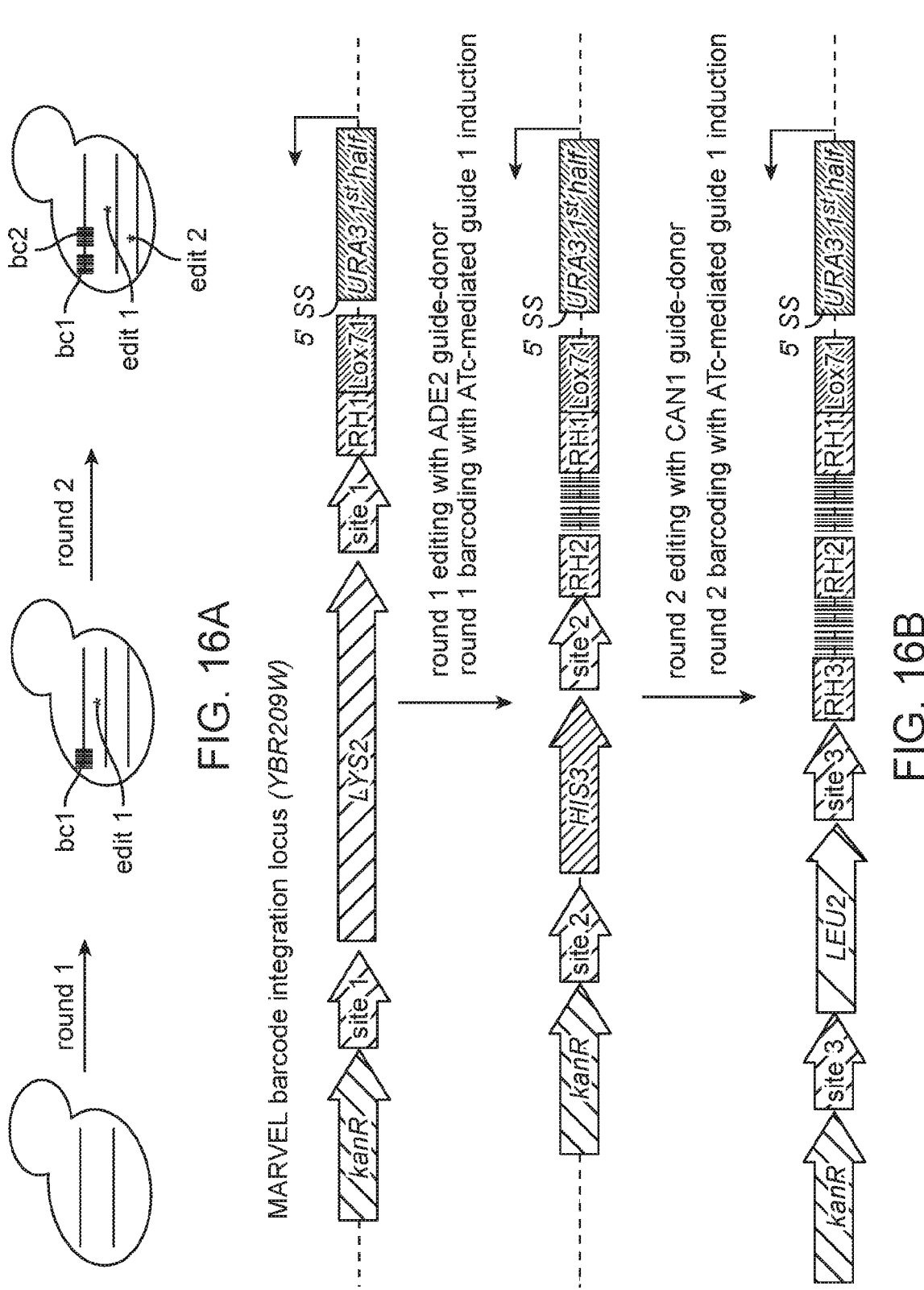
FIGS. 16A-16C show the overall methodology. Two different barcoded strains from round 1 were subjected to round 2 of recursive barcode linkage with a single barcoded CAN1 guide-donor plasmid, with confirmation of barcode linkage at the barcode locus by Sanger sequencing (FIG. 16C).

For barcode linkage proof of principle, we introduced a guide-donor editing ADE2 for round 1 and then a guide-donor editing CAN1 for round 2. To test that barcode linkage works independent of the barcode 1, two round 1 strains were generated with different barcodes, and a single barcoded round 2 plasmid was introduced into each strain (FIG. 16A). FIG. 16B shows the barcode locus before round 1 (top), after round 1 (middle), and after round 2 of recursive barcode linkage (bottom). In this proof of principle, a round 1 guide-donor plasmid targets the ADE2 gene, and the round 2 guide-donor targets the CAN1 gene.

Figure 16C:
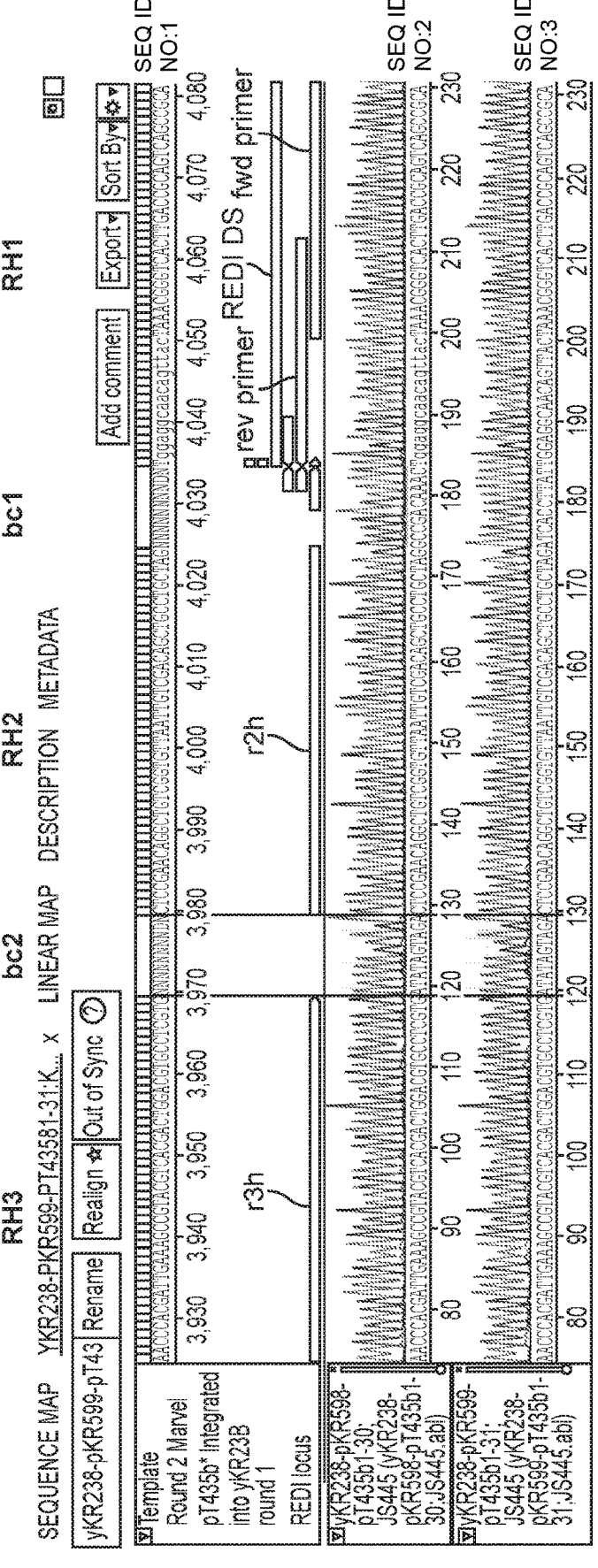

Inducing the barcoding guide with the small molecule anhydrotetracycline (ATc) led to successful recombination with a 45-bp RH sequence, demonstrating that barcodes can be linked (FIG. 16C). The highlighted sequences represent the barcodes.

Figure 17:
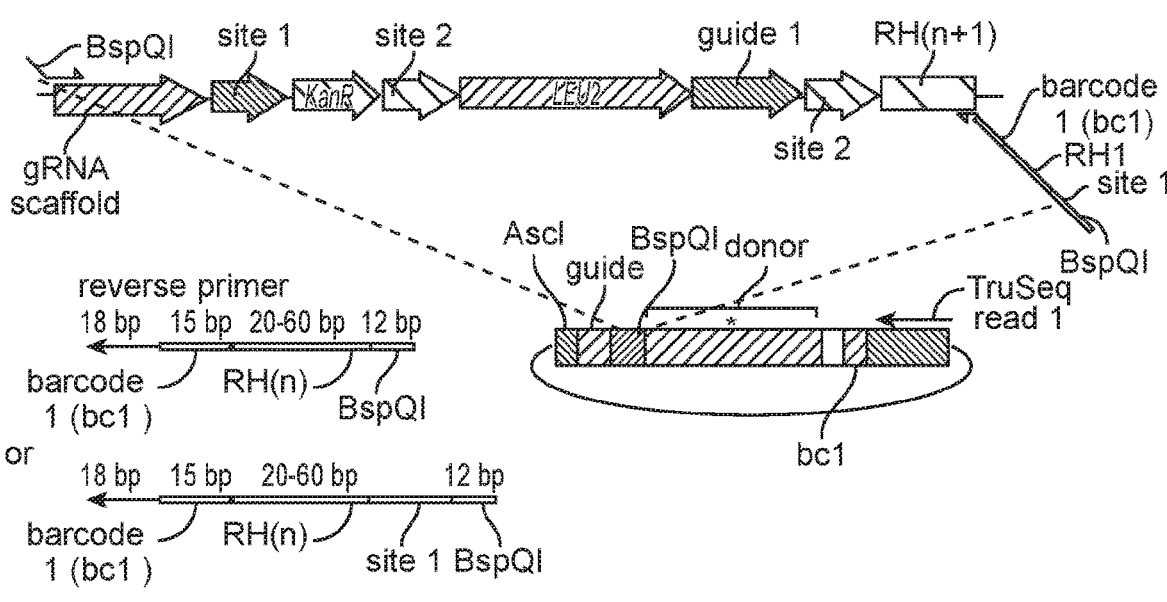
FIG. 17 shows the dependence of barcoding efficiency on RH length in the presence or absence of an RH-proximal cut site. All constructs have an LH-proximal cut site.

Example 6. Determination of Barcoding Efficiency as Function of RH Length and Presence of an RH-Proximal Cut Site Multiple opposing factors influence the desired length of the RH sequence. On the one hand, the RH sequence needs to be long enough to promote efficient homologous recombination. On the other hand, the shorter the RH, the more barcodes can be linked together and fit into a read of a given length. In addition, the shorter the barcode linkage length, the less prevalent PCR recombination will be during the phenotyping process. Also, as the RH must be included in the reverse primer, this is an additional practical constraint on the length. We therefore sought to find the minimum length of RH that supports efficient integration, testing 0, 20, 30, 40, 50, and 60 bp (FIG. 17A). These plasmids were then modified to contain an additional cut site directly adjacent to RH. These plasmids (which contain ADE2 guide-donors) were introduced into a Cas9/TetR/LexA-FHA-expressing strain and kept in -LYS-LEU medium to select against premature barcode integration and maintain the guide-donor plasmid. They were then transferred to -LEU+ATc medium to induce barcoding, and aliquots were sampled every 3 generations using an automated liquid handling system (TECAN Evo). PCR with primers flanking the barcode locus indicate the ratio of unmodified locus (FIG. 17B, lower band) to integrated barcode (upper band). The ratio of barcoded-to-nonbarcoded cells reached a steady-state after ~9 generations, and did not go to completion after 15 generations even with 60 bp of homology.

Strikingly, there was a substantial drop in integration efficiency going from 30 bp to 20 bp of RH, with 20 bp of RH performing no better than 0 bp. The process of barcoding involves a Cas9::guide complex cleaving at two sites flanking a marker at the genomic integration site, as well as upstream of the long left homology (LH) on the guide-donor plasmid. We hypothesized that a short RH sequence would be more efficiently recognized if an additional cut site were introduced directly adjacent to the RH. Remarkably, the addition of an RH-proximal cut site not only vastly increased the kinetics of barcoding and led to near complete barcoding after only 3 generations, but also led to highly efficient utilization of the 20 bp RH with comparable efficiencies independent of the RH length (FIG. 17C). This suggests that the barcode linkage unit can be as small as 30 bp (10 bp barcode with 20 bp RH sequence), enabling more linkage steps before a compression step is needed, and greatly mitigating the likelihood of PCR recombination causing problems with variant counting. This highlights the unique strength of the self-destructing/self-integrating vector, as the vector can be linearized under conditions which require selection for its marker by integrating the barcoded-marker portion of the vector.

Example 7. Barcoding Entire Gene Libraries & Pathways for Gene Insertion at Arbitrary Loci FIG. 20 shows a method for barcoding entire gene libraries & pathways for gene insertion at arbitrary loci. Barcoding and cloning of a gene variant library is performed as in Example 3. Long read technologies can be used to associate unique bc1 sequences with gene sequences, as in Example 3 (FIGS. 11A-11B). Two separate homologies are utilized, R1LH* and R1RH*, to enable insertion of the gene variant at an arbitrary locus. These * homologies flank the target site for the gene insertion guide 1. The bc1 and accompanying markers integrate at the barcode locus.

Example 8. Simultaneous Barcode Insertion at the Barcode Locus and Gene Insertion at an Arbitrary Locus FIG. 21 shows simultaneous barcode insertion at the barcode locus and gene insertion at an arbitrary locus. The barcoded gene variant plasmid library from Example 4 (FIG. 12) is transformed into cells. The gene insertion guide 1 is induced separately or simultaneously with the barcode guide 1. Insertion of the gene variant at the desired target locus and bc1 at the barcode locus. Reiterating the process allows for an arbitrary number of genes to be inserted at pre-defined loci across the genome, while the barcode locus can undergo barcode linkage followed by barcode compression and barcode locus contraction as in FIGS. 5A-5B.

Figure 22A:
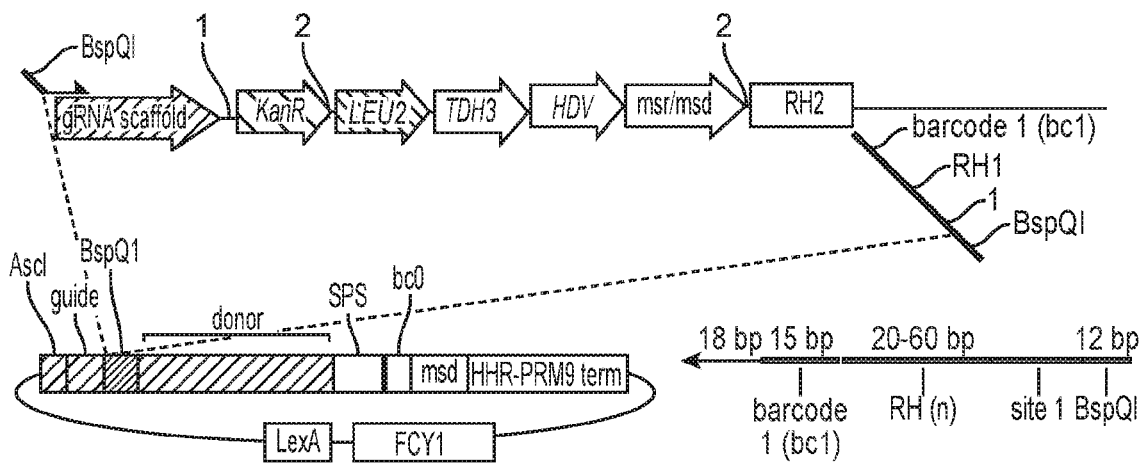
FIGS. 22A-22C show a modification of the guide-donor plasmid with retron elements flanking the donor. The donor is transcribed by a RNA polymerase II promoter, ribozymes remove the 5'cap and poly(A) tail, and the retron elements (msr/msd) promote reverse-transcription of the donor RNA to generate donor cDNA. In this system modification, editing of the target variant can occur either through homologous recombination with the donor cDNA or the plasmid-based donor.
Figure 22B:
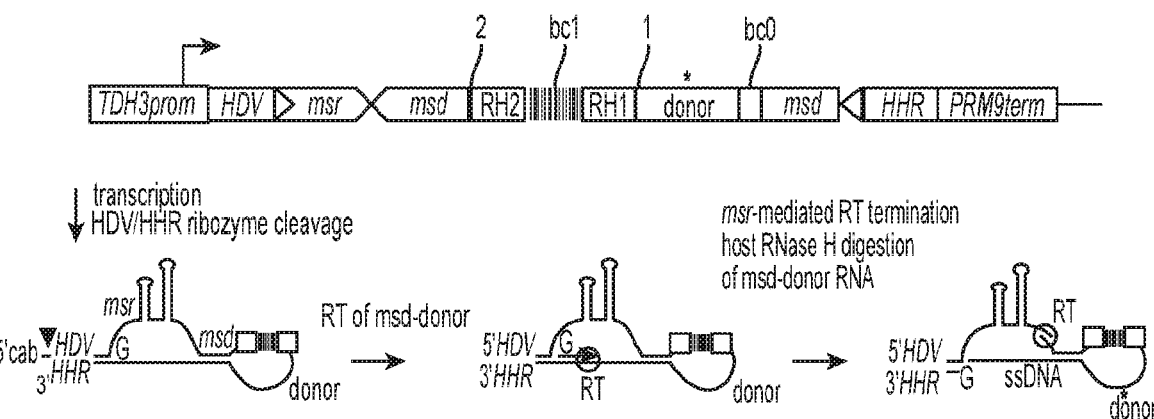
Figures 22C, 23A:
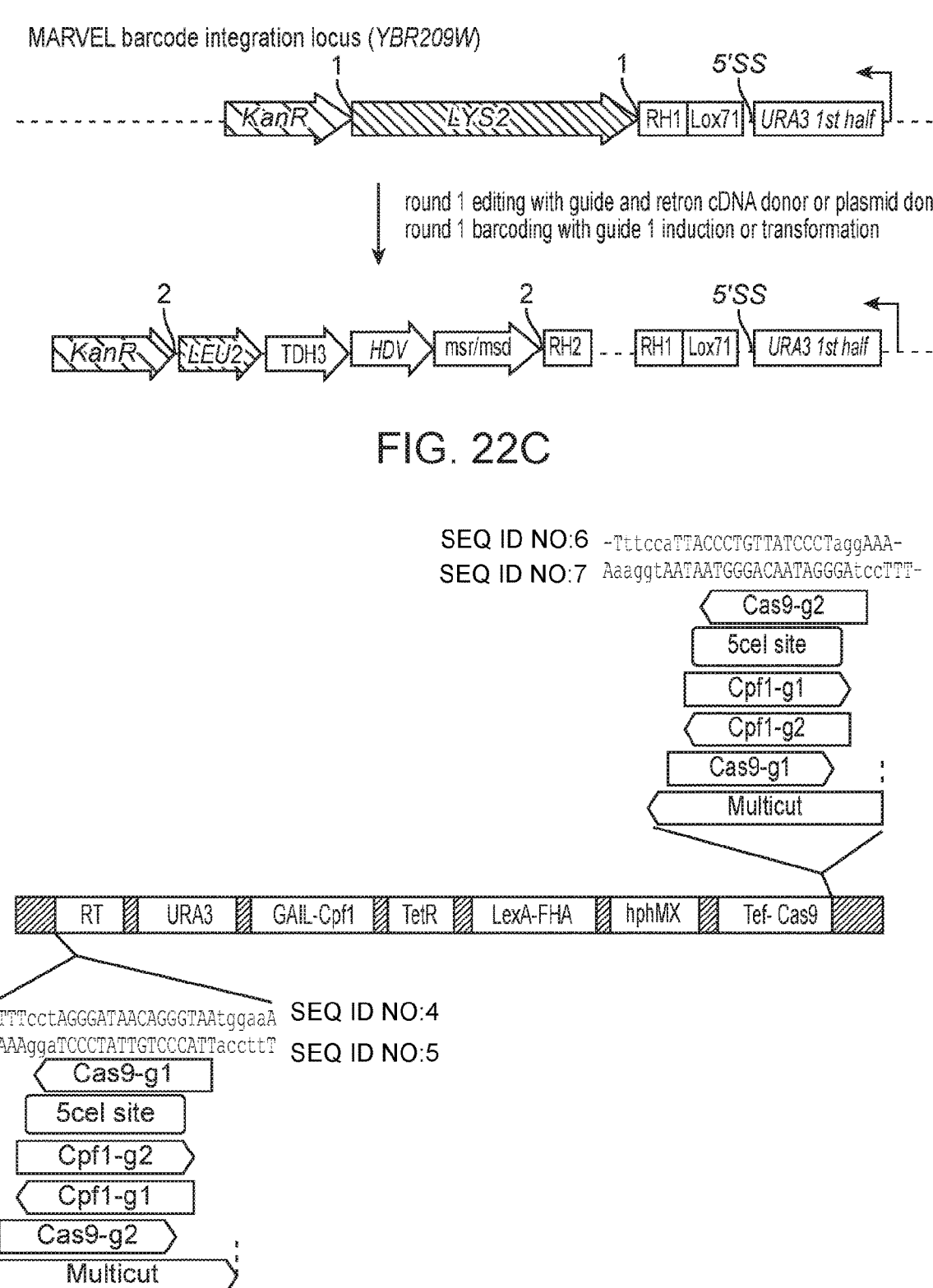
FIGS. 23A-23C show a schematic for integrating guide-donor plasmids via multiple cut-sites on the donor plasmid and barcode locus. Multiple cut-site sequence detail for guide-donor integration at a desired locus. An inducible nuclease (Cpf1/Cas12a and I-SceI shown here) other than the nuclease used for the gene edit (Cas9 in this example) enables integration of the guide-donor portion of the plasmid into the genome and subsequent guide-donor plasmid destruction.
Figure 23B:
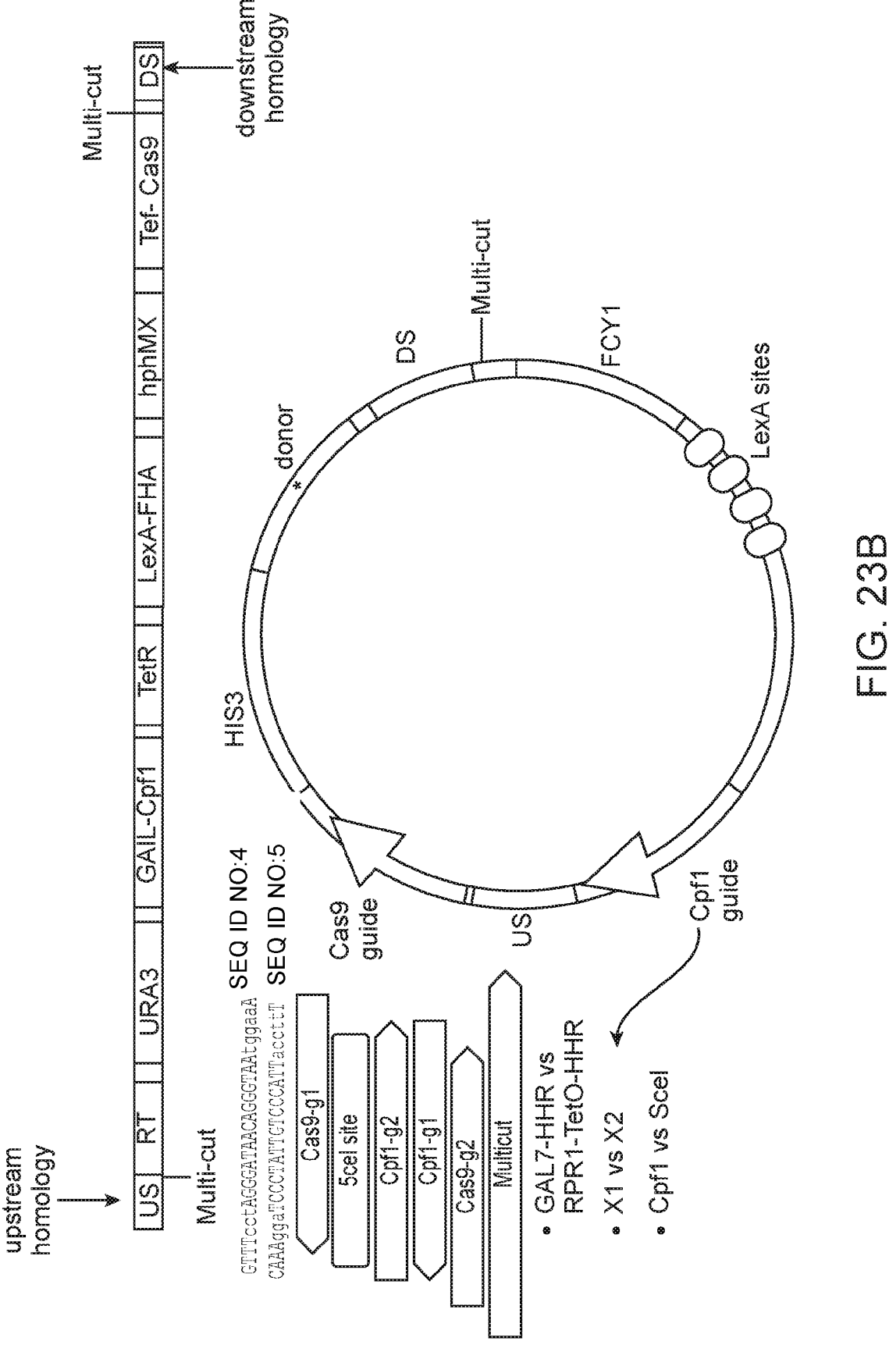
Figure 23C:
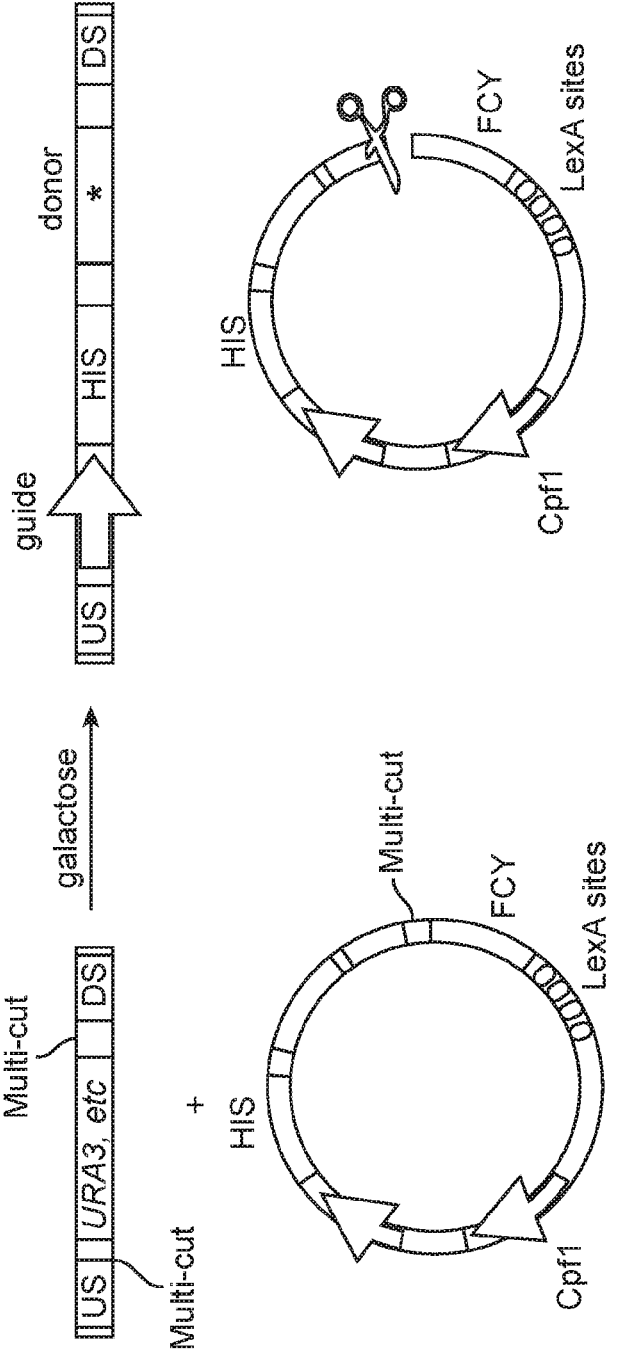

Example 9. Inducible, Self-Destructing Plasmid for Barcode Incorporation Using a Non-Redundant Nuclease from the Germline Editor This example illustrates a method to destroy the donor plasmid after each round of donor DNA incorporation into the genomic DNA. As expressed, the sequence of the donor plasmid generates a different, non-redundant nuclease from the germline editing nuclease already incorporated into the genome of the yeast strain of interest (Cas9, for example). As shown in the FIGS. 23A-23C, the nuclease Cpf1 can be used. Cpf1 can be expressed under an inducible promoter, in this case the GAL7 promoter, along with a guide RNA sequence that targets the multi-cut site shown in FIG. 23A. In the presence of galactose, the cells containing the Cpf1-donor plasmid shown in FIG. 23B will express Cpf1 and the Cpf1 guide RNA. Both the genomic and plasmid DNA are cleaved at the multi-cut site by Cpf1. The donor plasmid sequence generated by Cpf1 cleavage is integrated into the genomic DNA, starting at the upstream homology site (UH), and in this case, the donor DNA contains a HIS3 gene for selection, the sequence of interest, including the barcode sequence, and the downstream homology site (DH), as shown in FIG. 23B. In other embodiments, the donor DNA can be limited to incorporate only the barcode and location for a subsequent round (e.g., homology domain(s)).

Figure 24A:
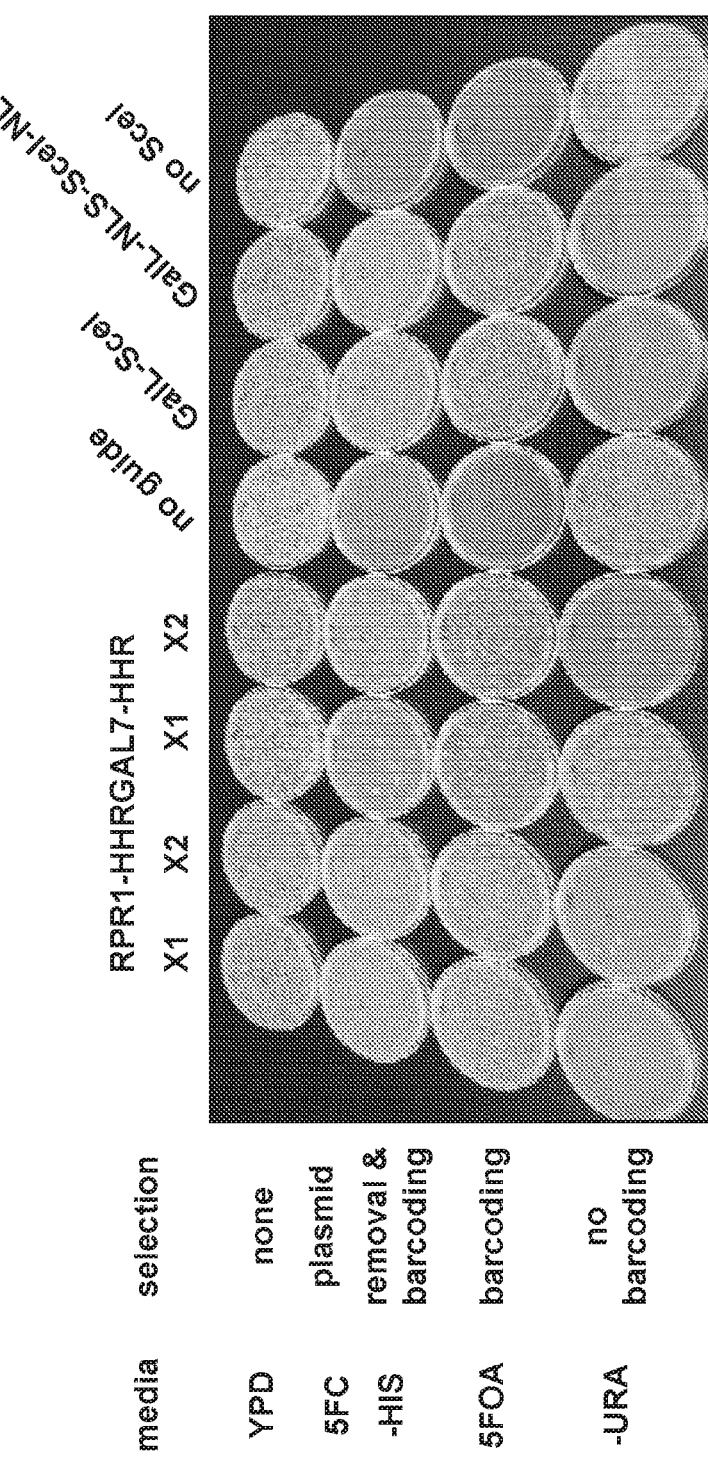
FIG. 24A is a photograph of petri dishes plated with yeast that had been exposed to galactose for twelve generations with the barcoding method indicated above the photograph. The Cpf1/Cas12a guide was expressed with two different guide sequences (X1 and X2) under two different promoters (RPR1-TetO and GAL7 with and without the aid of the hammerhead ribozyme (HHR) to remove the guide transcript leader. The Cpf1/Cas12a was placed under control of the Gal-L promoter for the five left-most columns. I-SceI nuclease with and without a dual nuclear localization signal (NLS) was placed under control of the Gal-L promoter for the indicated columns. Approximately 1000 cells of yeast were plated on the indicated media. YPD enables all viable cells to form colonies, 5FC-HIS selects for cells that underwent barcode integration and plasmid removal, 5FOA selects for cells that underwent barcode integration, and -URA selects for cells that have not undergone barcode integration. The controls for no guide and no SceI indicate that in the absence of guide cleavage, barcode integration and plasmid removal does not proceed.

FIG. 24A shows four separate yeast growth conditions after 12 generations of growth in the presence of galactose (from top to bottom: no selection (YPD), positive selection for plasmid removal/barcoding (5FC-HIS), barcoding (5FOA), and no barcoding (-URA)). Various configurations of donor plasmid were tested (from left to right: RPR1-HHR with X1 or X2 guide RNA; GAL7-HHR with X1 or X2 guide RNA; no guide; Gal-SceI; Gal-NLS-SceI-NLS; and no SceI. NLS: nuclear localization signal.

Figure 24B:
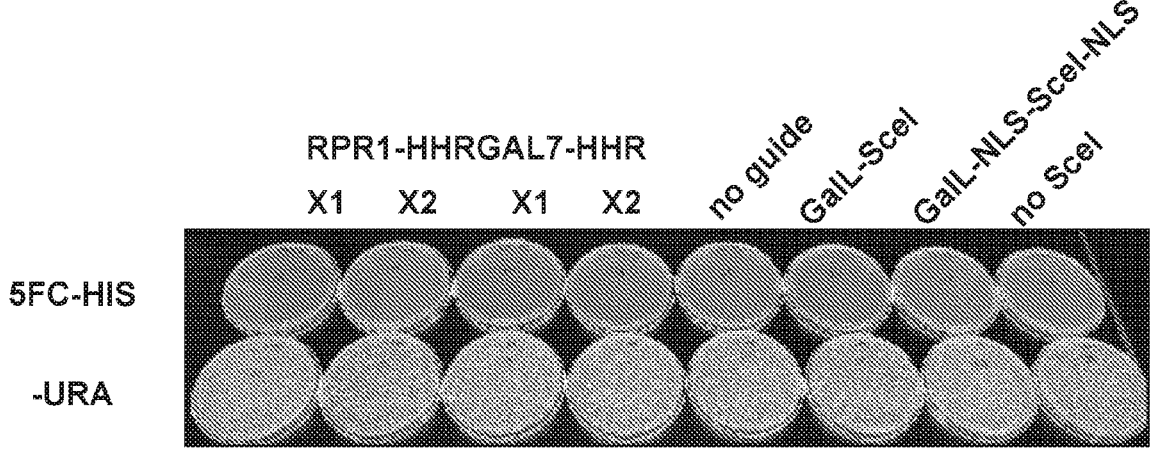
FIG. 24B is a photograph of petri dishes plated with yeast at time zero (no galactose induction), showing minimal leakiness of the Cpf1/Cas12a-guideX system or the I-SceI system.
Figure 24C:
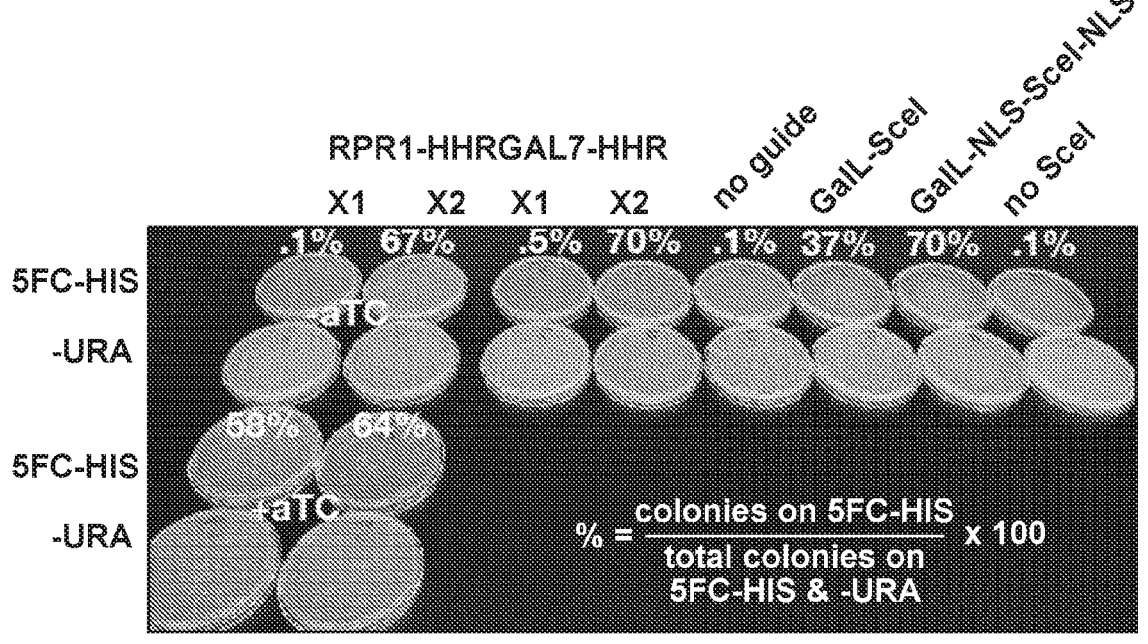
FIG. 24C is a photograph of petri dishes plated with yeast that had been exposed to galactose for six generations. Approximately 1000 cells of yeast were plated on the indicated media. Growth on the different media indicate varying percentages of barcode integration and plasmid removal.

FIG. 24B shows the plasmid removal/barcoding (5FC-HIS) and no barcoding (-URA) conditions with the analogous plasmid configuration to FIG. 24A after the first generation of yeast (before exposure to galactose), demonstrating minimal leakiness of the donor plasmids. The rate of barcode incorporation from the donor plasmid to the genomic DNA per generation is shown in FIG. 24C. After six generations of growth in the presence of galactose, donor plasmids containing the X2 Cpf1 guide sequence are greater than 50% exchanged (% exchanged=(5FC-HIS colonies/ (5FC-HIS colonies+-URA colonies))×100%), whereas <1% of the X1 Cpf1 guide-containing plasmids are exchanged. Donor plasmids containing SceL and NLS-SceI-NLS are highly exchanged (37% and 70%, respectively).

Barcode integration and plasmid destruction were confirmed by polymerase chain reaction.

Example 10. Passive Donor Plasmid Loss Over Time

Figure 25:
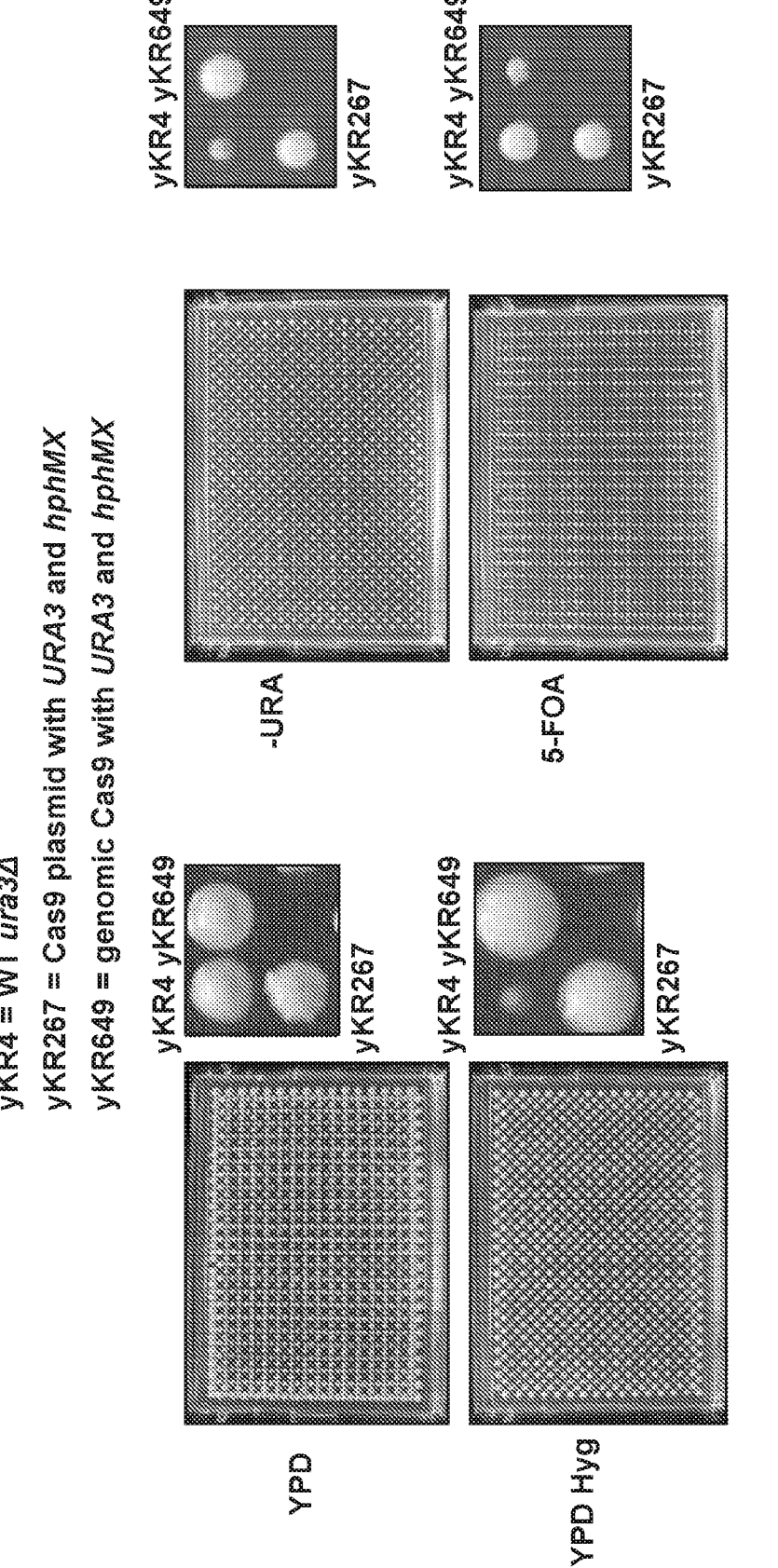
FIG. 25 are photographs of yeast colony arrays showing passive Cas9 plasmid loss during growth on 1536-density YPD agar. A colony array with yKR4 (control with URA3 gene deleted), yKR267 (Cas9/URA3/hphMX on a plasmid) and yKR649 (Cas9/URA3/hphMX in the genome) was stamped first on YPD to allow a fraction of the cells in each colony to lose the Cas9 plasmid (upper left). This array was then replica-plated to agar composed of YPD+hygromycin B (YPD+Hyg, lower left) which maintains selection for the Cas9, -URA (upper right) which maintains selection for the Cas9, and 5-FOA which requires the loss of the Cas9 plasmid to enable colony growth. The strain with genomic Cas9 (yKR649) cannot lose the Cas9/URA3/hphMX construct because it is stably inherited with the yeast genome.
Figure 26:
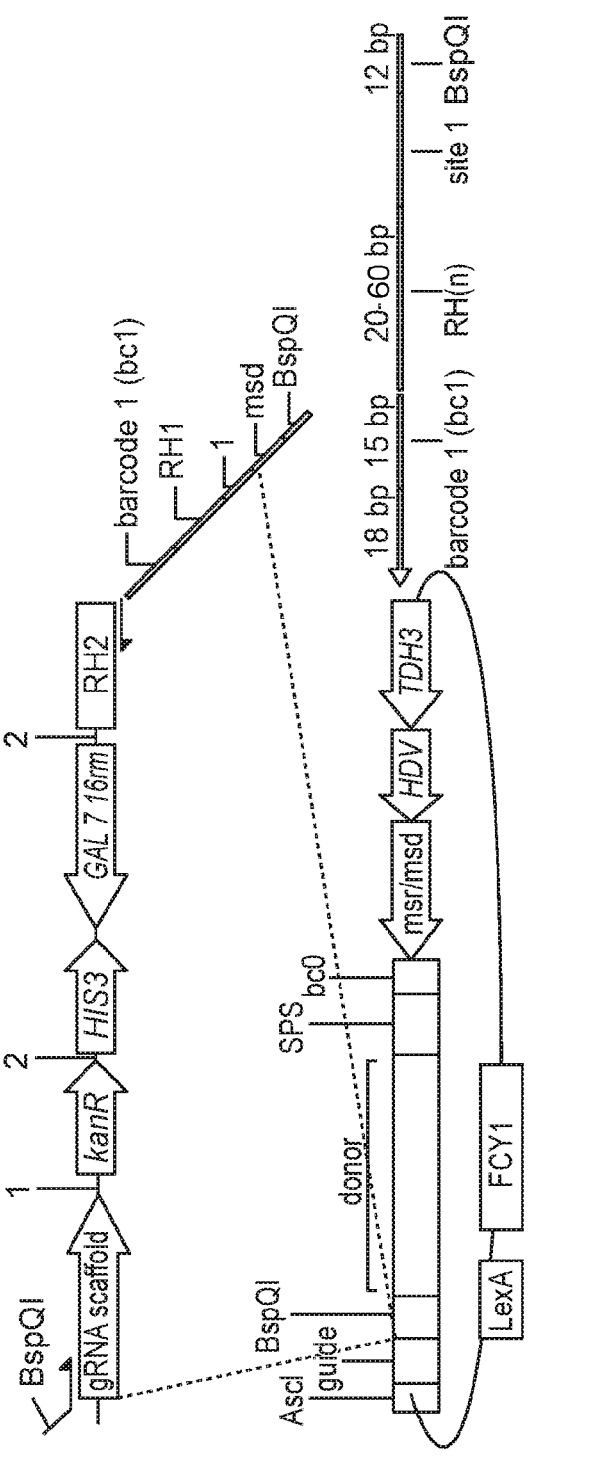
FIG. 26 is a schematic showing a guide-donor plasmid with the TDH3-HDV-msr/msd retron sequence in the reverse direction from other plasmid components.

Passive donor plasmid loss over time is demonstrated in FIG. 25 Three yeast strains, yKR4 (wild type ura3Δ, the negative control), yKR267 (containing Cas9 plasmid with URA3 and hphMX dominant drug resistance marker cassette), and yKR649 (genomic integrated Cas9 with URA3 and hphMX DDRM cassette) were grown for 24 hours with various selection markers (-URA, YPD, YPD-HYG, or hygromycin B, and 5-FOA). The large colonies indicate a positive selection, and the very small or lack of colony indicates a negative selection for the various growth media.

Yeast strain WT ura3Δ, which lacks the URA3 gene, grows on the YPD (positive control media), 5-FOA containing media, and does not grow on (+)HYG media (positive control for hthMX DDRM cassette). Yeast strain yKR267 grows on YPD, YPD-HYG, -URA, and 5-FOA media, indicating the Cas9-containing plasmid is retained in both the no plasmid phenotyping media (5-FOA), and positive plasmid selection media (-URA) (so, this yeast grows in opposite selections). Therefore yeast strain yKR267 can grow with and without plasmid incorporation. Yeast strain yKR649 grows on YPD, YPD-HYG, and -URA, but not on 5-FOA media. Therefore the yKR649 yeast strain retains URA3 activity.

Example 11. Donor Plasmid Destruction Via Transiently Expressed SceI

Figure 27:
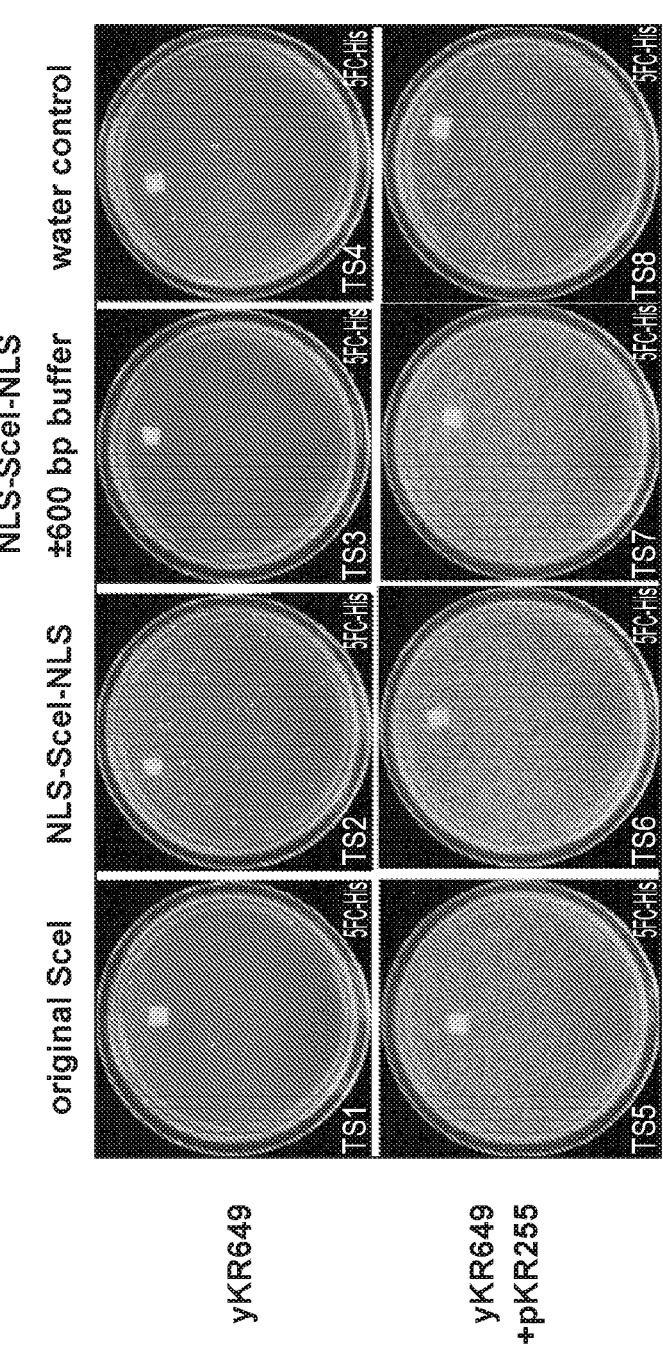
FIG. 27 is a photograph of petri dishes plated with yKR649 yeast, showing barcode integration with transiently-expressed SceI. PCR product encoding the DNA for SceI was co-transformed with the donor plasmid. SceI cuts at the genome and plasmid multi-cut site for barcode and iteration site integration and for donor plasmid destruction. The plates are plated with the yKR649 yeast strain on 5-FC counter selection media, against the guide-donor plasmid that contains the HIS3 gene. Plates with efficient guide-donor, or barcode, incorporation display a multitude of colonies as compared to inefficient incorporation (zero or few colonies).

In this example, the yeast strain yKR649 is transformed with the pKR255 plasmid. In addition, PCR products of various sequences of SceI are co-transformed with the plasmid to transiently elevate SceI expression without induction with a small molecule (galactose, for example). The sequences of SceI in the example are: the full-length SceI sequence, a dual NLS-flanked SceI sequence, and a 600 bp±dual NLS-flanked SceI sequence. The cells were grown with sufficient outgrowth time to allow for SceI expression and cutting of the genome and plasmid in the multi-cut sites, and for homology repair mechanism to integrate the barcode using a HIS3 selection, shown in FIG. 27. Dilutions of 1:100 of the SceI PCR products were assessed and also generated efficient donor DNA incorporation.

Figures 28A, 28B:
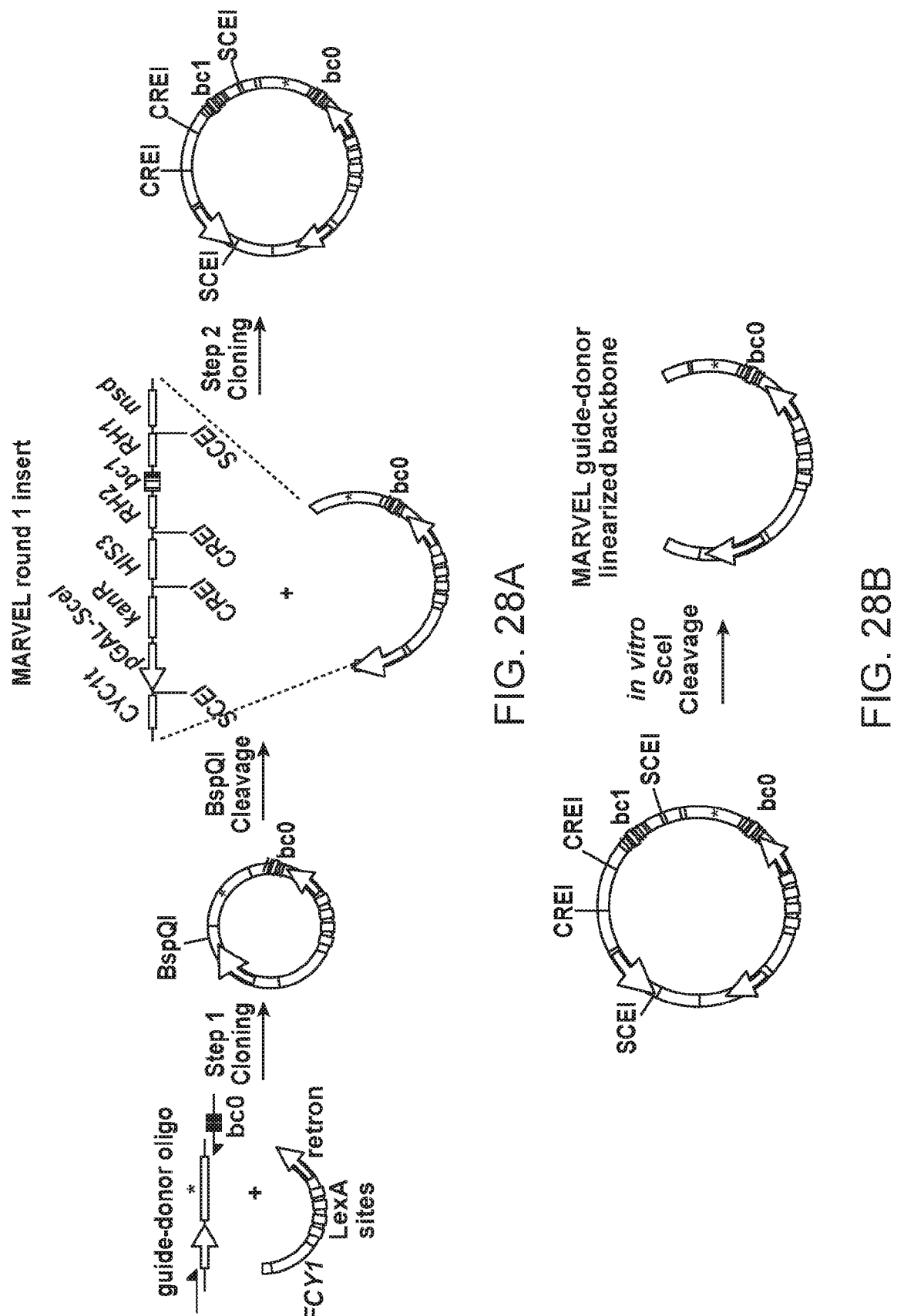
FIGS. 28A-28C present a strategy for concurrent editing with in vivo assembly of MARVEL plasmids.
Figure 28C:
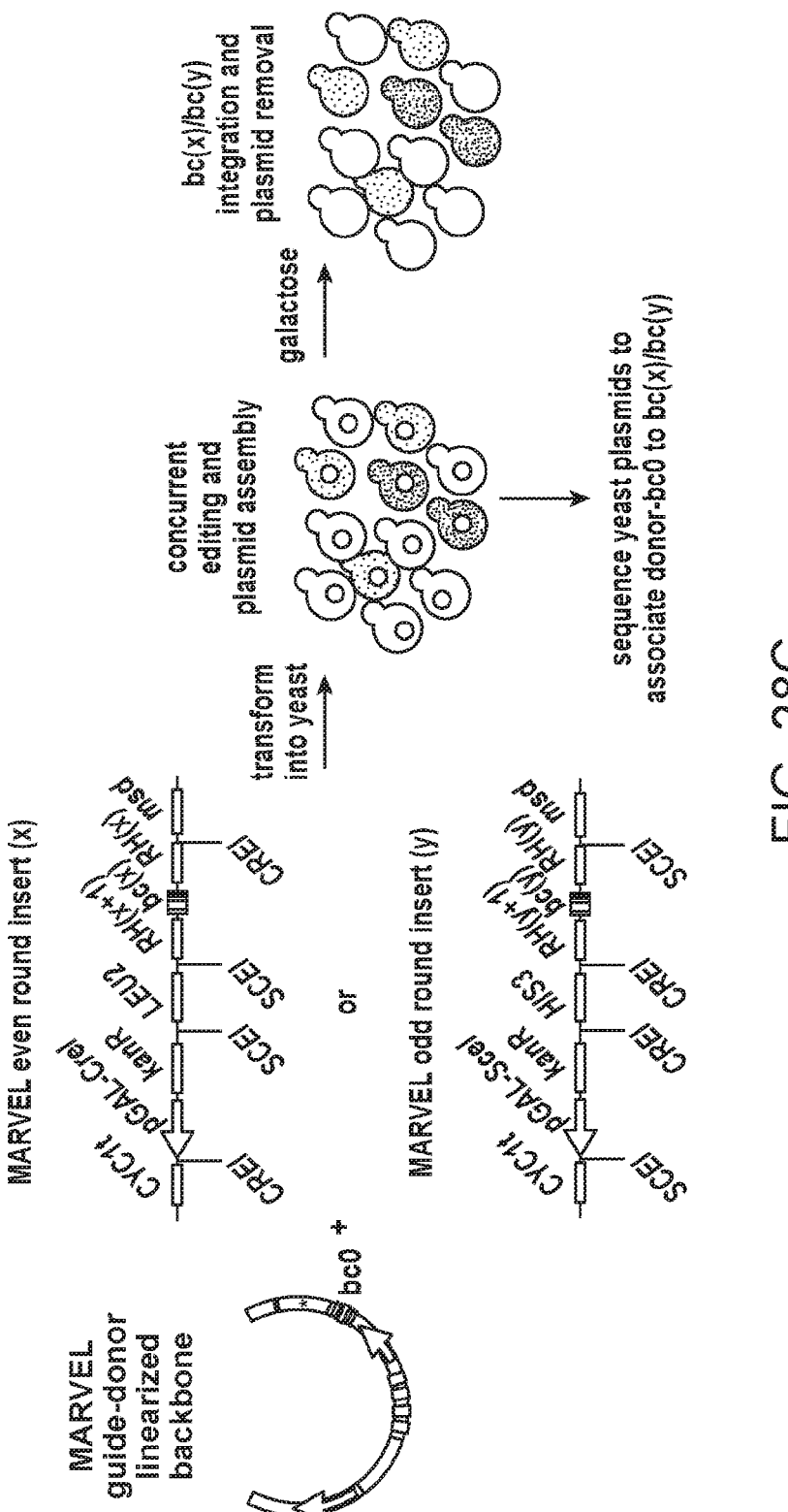

Example 12. A Strategy for Concurrent Editing with In Vivo Assembly of MARVEL Plasmids In this example, FIGS. 28A-28C present a strategy for concurrent editing with in vivo assembly of MARVEL plasmids. Guide-donor oligonucleotides are cloned into the plasmid backbone with the addition of a barcode sequence, labeled bc0, adjacent to the donor. This approach is compatible with multiple methods of donor DNA enhancement, including donor recruitment by LexA-FHA and ssDNA donor amplification by retron. BspQI cleavage enables cloning in the MARVEL round 1 insert, which harbors SCEI sites for round 1 barcode integration and CREI sites to enable a subsequent round 2 barcode integration. FIG. 28B shows that round 1 plasmids can be parsed first in yeast or bacteria to create a library where each guide-donor is sequence perfect and present at equal abundance. SCEI sites are cleaved by the meganuclease SceI in vitro to create a library of linearized guide-donor backbones. The main function of this step is to introduce long homology arms (~200 bp of CYC1t sequence on one side, and ~45 bp of msd retron sequence on the other side). FIG. 28C shows the linearized backbone generated by SceI cleavage can be transformed directly into yeast along with the appropriate round of MARVEL insert. The linearization of the plasmid not only eliminates the need for additional step 2 cloning in bacteria, but also enhances editing efficiency. Yeast assemble the plasmid libraries concurrent with editing, and the donor-bc0 sequences can be mapped onto the new barcodes by sequencing the yeast pools. Galactose induction integrates the barcodes and removes the plasmids. Odd round selection is accomplished with 5FC-HIS, and even round selection by 5FC-LEU.

What is claimed is:

1. A method for producing a plurality of genetically engineered cells, the method comprising:

(a-1) contacting a plurality of cells with a first gene editing agent and a first plurality of recombinant polynucleotides, each recombinant polynucleotide in the first plurality comprising a first unique polynucleotide barcode sequence, thereby forming a first plurality of gene edited and barcoded cells, each gene edited and barcoded cell comprising the first unique polynucleotide barcode inserted into a barcode locus, and a first unique genetic modification; and (b-1) contacting the first plurality of gene edited and barcoded cells with a second gene editing agent and a second plurality of recombinant polynucleotides, each recombinant polynucleotide in the second plurality comprising a second unique polynucleotide barcode sequence, thereby forming a second plurality of gene edited and barcoded cells, each gene edited and barcoded cell comprising the second unique polynucleotide barcode inserted into a barcode locus and a second unique genetic modification, or (a-2) contacting a plurality of cells with a first gene editing agent thereby producing a first plurality of gene edited cells each comprising a first unique genetic modification;

(b-2) transfecting into the first plurality of gene edited cells a first plurality of recombinant polynucleotides, each recombinant polynucleotide in the first plurality comprising a first unique polynucleotide barcode sequence, thereby forming a first plurality of gene edited and barcoded cells, each gene edited and barcoded cell comprising the first unique polynucleotide barcode inserted into a barcode locus and the first unique genetic modification;

(c) contacting said first plurality of gene edited and barcoded cells with a second gene editing agent thereby producing a second plurality of gene edited cells each comprising a second unique genetic modification; and (d) transfecting into the second plurality of gene edited cells a second plurality of recombinant polynucleotides, each recombinant polynucleotide in the second plurality comprising a second unique polynucleotide barcode sequence, thereby forming a second plurality of gene edited and barcoded cells, such that the second unique polynucleotide barcode is inserted into a barcode locus of each of said second plurality of gene edited and barcoded cells, each gene edited and barcoded cell comprising the second unique polynucleotide barcode inserted into a barcode locus and the second unique genetic modification, thereby producing a plurality of genetically engineered cells;

wherein the method provides linking of unique barcodes sequentially integrated adjacent to one another at specific time points to enable lineage tracking and/or enables higher order combinatorial genetic modifications to be constructed and tracked with either a single barcode or short barcode array, and wherein multiple individual barcodes combine to generate a larger single barcode, where order of barcodes represents order of addition of genome edits, enabling sequencing-based approaches to identify and count barcode permutations or combinations.

2. The method of claim 1, further comprising repeating step (b-1) or steps (c) and (d) one or more times, wherein each repeat of step (b-1) or steps (c) and (d) employs a plurality of recombinant polynucleotides, each recombinant polynucleotide comprising a unique polynucleotide barcode sequence.

3. The method of claim 1, wherein i) the first unique polynucleotide barcode of step (a-1) or step (b-2) is associated with the first unique genetic modification in each of said first plurality of gene edited and barcoded cells;

ii) the second unique polynucleotide barcode of step (a-2) or step (d) is associated with the second unique genetic modification in each of said second plurality of gene edited and barcoded cells;

iii) the barcode locus and at least a portion of the genome that includes a genomic sequence comprising the first unique genetic modification of each of said first plurality of gene edited and barcoded cells are sequenced, such that the first unique polynucleotide barcode is associated with the first unique genetic modification in a database;

iv) the barcode locus and at least a portion of the genome that includes a genomic sequence comprising the second unique genetic modification of each of said second plurality of gene edited and barcoded cells are sequenced, such that the second unique polynucleotide barcode is associated with the second unique genetic modification in a database;

v) each unique polynucleotide barcode is added adjacent to a most recently integrated unique polynucleotide barcode in the barcode locus;

vi) each unique polynucleotide barcode is added upstream of a most recently integrated unique polynucleotide barcode in the barcode locus;

vii) each unique polynucleotide barcode is added downstream of a most recently integrated unique polynucleotide barcode in the barcode locus;

viii) each unique polynucleotide barcode is flanked on the recombinant polynucleotide by a right homology arm and/or a left homology arm;

ix) each first unique polynucleotide barcode is flanked on each recombinant polynucleotide of the first plurality of polynucleotides by a first right homology arm, a second right homology arm, and a left homology arm, such that the first right homology arm and the left homology arm are homologous to a sequence at the barcode locus; and/or x) each unique polynucleotide is inserted in the barcode locus by homologous recombination or non-homologous end joining, or using an integrase.

4. The method of claim 1, wherein i) each recombinant polynucleotide further comprises a marker polynucleotide and/or a donor polynucleotide; and/or ii) each recombinant polynucleotide is provided by a vector.

5. The method of claim 1, wherein i) at least one of the first gene editing agent and the second gene editing agent is a meganuclease, zinc finger nuclease (ZFN), transcription activator-like effector-based nuclease (TALEN), clustered regularly interspaced short palindromic repeats (CRISPR) system, RNA-guided nuclease, RNA-guided nickase, a chemical agent, a recombinase, an integrase, or a transposase;

ii) the first gene editing agent and the second gene editing agent are the same;

iii) the first gene editing agent and the second gene editing agent are different; and/or iv) at least one of the first gene editing agent and the second gene editing agent is a meganuclease, an RNA-guided nuclease, or an RNA-guided nickase.

6. The method of claim 1, further comprising i) sequencing from a sample of cells at least a portion of the chromosome that includes a genomic sequence comprising the second unique genetic modification from the second plurality of gene edited and barcoded cells;

ii) inserting a new unique polynucleotide barcode in the barcode locus of each cell, wherein the barcode locus already comprises at least two unique polynucleotide barcodes prior to insertion of the new unique polynucleotide barcode, and sequencing the barcode locus such that the new unique polynucleotide barcode is associated with the at least two unique polynucleotide barcodes;

iii) contacting said second plurality of gene edited and barcoded cells with a second nucleic acid sequence encoding a guide RNA capable of hybridizing with the recombinant polynucleotide, wherein the guide RNA forms a complex with a nuclease in each cell such that the guide RNA-nuclease complex cleaves the recombinant polynucleotide or the barcode locus.

7. The method of claim 1, wherein i) the barcode locus is a chromosomal barcode locus;

ii) the genetic modification is a designed genetic modification; and/or iii) the vector is removed from the cell.

8. A plurality of gene edited and barcoded cells made by the method of claim 1.

9. A method for producing a plurality of barcoded cells, comprising:

(a) contacting a plurality of cells with a first plurality of recombinant polynucleotides, each recombinant polynucleotide comprising a unique polynucleotide barcode sequence, such that a first unique polynucleotide barcode is inserted into a barcode locus of each of said first plurality of cells, thereby forming a first plurality of barcoded cells; and (b) contacting the first plurality of barcoded cells with a second plurality of recombinant polynucleotides, each recombinant polynucleotide comprising a unique polynucleotide barcode sequence, such that a second unique polynucleotide barcode is inserted into the barcode locus of each of said first plurality of gene edited and barcoded cells, thereby forming a second plurality of gene edited and barcoded cells;

thereby producing a plurality of barcoded cells.

10. The method of claim 9, further comprising repeating step (b) one or more times.

11. The method of claim 9, wherein each unique polynucleotide barcode i) is associated with a genetic modification in each cell;

ii) is added adjacent to a most recently integrated unique polynucleotide barcode in the barcode locus;

iii) is added upstream of a most recently integrated unique polynucleotide barcode in the barcode locus;

iv) is added downstream of a most recently integrated unique polynucleotide barcode in the barcode locus;

v) is flanked on the recombinant polynucleotide by a right homology arm and/or a left homology arm;

vi) is inserted into the barcode locus by homologous recombination.

12. The method of claim 9, wherein each recombinant polynucleotide further comprises a marker polynucleotide.

13. The method of claim 12, further comprising (i) inserting a new unique polynucleotide barcode in the barcode locus of each cell, wherein the barcode locus already comprises at least two unique polynucleotide barcodes prior to insertion of the new unique polynucleotide barcode, (ii) sequencing the barcode locus such that the new unique polynucleotide barcode is associated with the at least two unique polynucleotide barcodes.

14. The method of claim 13, further comprising repeating steps (a) and/or (b), thereby producing a plurality of sequentially barcoded cells.

15. The method of claim 9, wherein the barcode locus is a chromosomal barcode locus or a plasmid barcode locus.

16. A plurality of barcoded cells made by the method of claim 9.

17. The method of claim 2, wherein each repeat of step (b-1) or steps (c) and (d) employs a plurality of recombinant polynucleotides, each recombinant polynucleotide comprising a unique polynucleotide barcode sequence.

18. The method of claim 17, wherein each repeat of step (b-1) and steps (c) and (d) employs a different plurality of recombinant polynucleotides, each recombinant polynucleotide in the different plurality comprising a unique polynucleotide barcode sequence.

19. The method of claim 1, wherein multiple individual barcodes combine to generate a larger single barcode, where the order of barcodes represents the order of addition of the genome edits, enabling sequencing-based approaches to identify and count barcode permutations or combinations.

* * * * *

SEQUENCE LISTING

<160> NUMBER OF SEQ ID NOS: 7

<210> SEQ ID NO 1
<211> LENGTH: 157
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (46)..(53)
<223> OTHER INFORMATION: N is any nucleotide
<220> FEATURE:
<221> NAME/KEY: misc_feature
<222> LOCATION: (54)..(54)
<223> OTHER INFORMATION: N is A, G, or T
<220> FEATURE:
<221> NAME/KEY: misc_feature
<222> LOCATION: (55)..(55)
<223> OTHER INFORMATION: N is any nucleotide
<220> FEATURE:
<221> NAME/KEY: misc_feature
<222> LOCATION: (101)..(108)
<223> OTHER INFORMATION: N is any nucleotide
<220> FEATURE:
<221> NAME/KEY: misc_feature
<222> LOCATION: (109)..(109)
<223> OTHER INFORMATION: N is A, G, or T
<220> FEATURE:
<221> NAME/KEY: misc_feature
<222> LOCATION: (110)..(110)
<223> OTHER INFORMATION: N is any nucleotide

<400> SEQUENCE: 1
aacccacgat tgaaagccgt acgtcaccac tggacgtgcc tcgtgnnnnn nnnnnctccg        60
aacaggctgt cggtgttaat tgtcgacagc tgcctgctag nnnnnnnnnn tggaggcaac       120
agttactaaa cgggtcactt gaccgcagtc agccgca                                157

<210> SEQ ID NO 2
<211> LENGTH: 157
<212> TYPE: DNA
<213> ORGANISM: Artificial sequence
<220> FEATURE:
<223> OTHER INFORMATION: Synthetic polynucleotide

<400> SEQUENCE: 2
aacccacgat tgaaagccgt acgtcacgac tggacgtgcc tcgtgatata gtagactccg        60
aacaggctgt cggtgttaat tgtcgacagc tgcctgctag gccgacaaac tggaggcaac       120
agttactaaa cgggtcactt gaccgcagtc agccgca                                157

<210> SEQ ID NO 3
<211> LENGTH: 156
<212> TYPE: DNA
<213> ORGANISM: Artificial sequence
<220> FEATURE:
<223> OTHER INFORMATION: Synthetic polynucleotide

<400> SEQUENCE: 3
aacccacgat tgaaagccgt acgtcacgac tggacgtgcc tcgtgatata gtagactccg        60
aacaggctgt cggtgttaat tgtcgacagc tgcctgctag atcaccttat ggaggcaaca       120
gttactaaac gggtcacttg accgcagtca gccgca                                 156

<210> SEQ ID NO 4
<211> LENGTH: 29
<212> TYPE: DNA
<213> ORGANISM: Artificial sequence -continued

```
<220> FEATURE:
<223> OTHER INFORMATION: Synthetic polynucleotide

<400> SEQUENCE: 4
gtttcctagg gataacaggg taatggaaa                                    29

<210> SEQ ID NO 5
<211> LENGTH: 29
<212> TYPE: DNA
<213> ORGANISM: Artificial sequence
<220> FEATURE:
<223> OTHER INFORMATION: Synthetic polynucleotide

<400> SEQUENCE: 5
caaaggatcc ctattgtccc attaccttt                                    29

<210> SEQ ID NO 6
<211> LENGTH: 28
<212> TYPE: DNA
<213> ORGANISM: Artificial sequence
<220> FEATURE:
<223> OTHER INFORMATION: Synthetic polynucleotide

<400> SEQUENCE: 6
tttccattac cctgttatcc ctaggaaa                                     28

<210> SEQ ID NO 7
<211> LENGTH: 28
<212> TYPE: DNA
<213> ORGANISM: Artificial sequence
<220> FEATURE:
<223> OTHER INFORMATION: Synthetic polynucleotide

<400> SEQUENCE: 7
aaaggtaatg ggacaatagg gatccttt                                     28
```